(12) United States Patent
Xiao

(10) Patent No.: US 11,384,380 B2
(45) Date of Patent: Jul. 12, 2022

(54) COMPOSITIONS AND METHODS FOR DETECTING N⁶-METHYLADENINE IN THE MAMMALIAN GENOME

(71) Applicant: YALE UNIVERSITY, New Haven, CT (US)

(72) Inventor: Andrew Xiao, Fairfield, CT (US)

(73) Assignee: Yale University, New Haven, CT (US)

( * ) Notice: Subject to any disclaimer, the term of this patent is extended or adjusted under 35 U.S.C. 154(b) by 636 days.

(21) Appl. No.: 16/085,071

(22) PCT Filed: Mar. 16, 2017

(86) PCT No.: PCT/US2017/022747
§ 371 (c)(1),
(2) Date: Sep. 14, 2018

(87) PCT Pub. No.: WO2017/161138
PCT Pub. Date: Sep. 21, 2017

(65) Prior Publication Data
US 2019/0078132 A1    Mar. 14, 2019

Related U.S. Application Data

(60) Provisional application No. 62/309,093, filed on Jun. 16, 2016.

(51) Int. Cl.
| | | |
|---|---|---|
| *C12Q 1/02* | (2006.01) | |
| *A61K 31/7088* | (2006.01) | |
| *C12N 15/113* | (2010.01) | |
| *C12Q 1/68* | (2018.01) | |
| *C12N 15/10* | (2006.01) | |
| *C12Q 1/6804* | (2018.01) | |
| *C12Q 1/6827* | (2018.01) | |
| *C12Q 1/6869* | (2018.01) | |
| *C12Q 1/6886* | (2018.01) | |

(52) U.S. Cl.
CPC .......... *C12Q 1/025* (2013.01); *A61K 31/7088* (2013.01); *C12N 15/1003* (2013.01); *C12N 15/113* (2013.01); *C12Q 1/68* (2013.01); *C12Q 1/6804* (2013.01); *C12Q 1/6827* (2013.01); *C12Q 1/6869* (2013.01); *C12Q 1/6886* (2013.01); *C12Q 2600/106* (2013.01); *C12Q 2600/112* (2013.01); *C12Q 2600/136* (2013.01)

(58) Field of Classification Search
CPC .............................. C12Q 1/68; C12N 15/1003
See application file for complete search history.

(56) References Cited

U.S. PATENT DOCUMENTS

| | | | | |
|---|---|---|---|---|
| 8,563,304 | B2 * | 10/2013 | Young | A61K 35/30 435/325 |
| 10,317,409 | B2 * | 6/2019 | Kim | G01N 33/57496 |
| 2009/0192112 | A1 | 7/2009 | Simeone | |
| 2010/0055688 | A1 | 3/2010 | Chinnaiyan | |
| 2010/0179213 | A1 | 7/2010 | Patrawala | |
| 2012/0289408 | A1 | 11/2012 | Travers | |
| 2013/0022974 | A1 | 1/2013 | Chinnaiyan | |
| 2014/0045915 | A1 | 2/2014 | Skog | |
| 2014/0315736 | A1 * | 10/2014 | Nagele | G01N 33/6896 506/9 |
| 2014/0343865 | A1 * | 11/2014 | Brown | G01N 33/5011 702/19 |
| 2015/0011403 | A1 * | 1/2015 | Lo | C12Q 1/6886 506/2 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Fu et al., N6-Methyldeoxyadenosine Marks Active Transcription Start Sites in Chlamydomonas. Cell 161 :879-892 (May 2015) (Year: 2015).*
Douvlataniotis et al. No evidence for DNA N6-methyladenine in mammals. Science Advances 6: eaay3335 (Year: 2020).*
Tsugita et al. Eur. J. Biochem. 124: 585 (Year: 1982).*
Sun et al., N6-Methyladenine Functions as a Potential Epigenetic Mark in Eukaryotes, BioEssays vol. 37, pp. 1155-1162 (2015).
Wu et al., DNA Methylation on N6-Adenine in Mammalian Embryonic Stem Cells, Nature, vol. 532, pp. 329-333 (2016).
Zhou et al., DNA N6-Methyladenine Demethylase ALKBH1 Enhances Osteogenic. Differentiation of Human MSCs, Bone Research, vol. 4, pp. 1-9, (2016).
Luo et al., DNA N6-Methyladenine: a New Epigenetic Mark in Eukaryotes?, Nature Reviews Molecular Cell Biology, vol. 16, pp. 705-710, (2015).
Zdzalik et al., Protozoan ALKBH8 Oxygenases Display both DNA Repair and tRNA Modification Activities, PLoS ONE, vol. 9, No. 6, pp. 1-13, (2014).
Abrusán et al., Analysis of transposon interruptions suggests selection for L1 elements on the X chromosome. PLoS Genet. 4, e1000172 (2008).
Achwal et al., Immunochemical evidence for the presence of 5mC, 6mA and 7mG in human, *Drosophila* and mealybug DNA. FEBS Lett. 158, 353-8 (1983).
Bailey et al., Molecular evidence for a relationship between LINE-1 elements and X chromosome inactivation: the Lyon repeat hypothesis, Proc. Natl. Acad. Sci. U. S. A. 97, 6634-9 (2000).
Baillie, J. K. et al. Somatic retrotransposition alters the genetic landscape of the human brain, Nature 479, 534-7 (2011).
Banaszynski et al., Histone variants in metazoan development. Dev. Cell 19, 662-74 (2010).
Bell and Felsenfeld, Methylation of a CTCF-dependent boundary controls imprinted expression of the Igf2 gene, Nature 405, 482-5 (2000).

(Continued)

*Primary Examiner* — Ethan C Whisenant
(74) *Attorney, Agent, or Firm* — Riverside Law LLP

(57) ABSTRACT

The invention provides compositions and methods for identifying DNA methylation. In one embodiment, the invention provides a method for detecting N⁶-methyladenine.

11 Claims, 36 Drawing Sheets

Specification includes a Sequence Listing.

(56) References Cited

OTHER PUBLICATIONS

Bourc'his and Bestor, Meiotic catastrophe and retrotransposon reactivation in male germ cells lacking Dnmt3L, Nature 431, 96-99 (2004).
Buganim et al., The Developmental Potential of iPSCs Is Greatly Influenced by Reprogramming Factor Selection. Cell Stem Cell 15, 295-309 (2014).
Byrum et al., Purification of a specific native genomic locus for proteomic analysis, Nucleic Acids Res., 41:e195 (2013).
Castro-Diaz et al., Evolutionarily dynamic L1 regulation in embryonic stem cells. Genes Dev. 28, 1397-409 (2014).
Chow et al., LINE-1 activity in facultative heterochromatin formation during X chromosome inactivation. Cell 141, 956-69 (2010).
Davis et al., Entering the era of bacterial epigenomics with single molecule real time DNA sequencing. Curr. Opin. Microbiol. 16, 192-8 (2013).
Delatte et al. ,Transcriptome-wide distribution and function of RNA hydroxymethylcytosine. Science. 351:282-285 (2016).
Erickson et al., Retrofitting the genome: L1 extinction follows endogenous retroviral expansion in a group of muroid rodents. J. Virol. 85, 12315-23 (2011).
Fadloun et al., Chromatin signatures and retrotransposon profiling in mouse embryos reveal regulation of LINE-1 by RNA. Nat. Struct. Mol. Biol. 20, 332-8 (2013).
Fang et al., Genome-wide mapping of methylated adenine residues in pathogenic *Escherichia coli* using single-molecule real-time sequencing. Nature Biotechnol. 30:1232-1239 (2012).
Flusberg et al., Direct detection of DNA methylation during single-molecule, real-time sequencing. Nat. Methods 7, 461-5 (2010).
Fu et al. Human AlkB homolog ABH8 Is a tRNA methyltransferase required for wobble uridine modification and DNA damage survival. Mol. Cell. Biol. 30, 2449-59 (2010).
Fu et al., N6-Methyldeoxyadenosine Marks Active Transcription Start Sites in Chlamydomonas. Cell 161, 879-92 (2015).
Gartler and Riggs, Mammalian X-chromosome inactivation. Annu. Rev. Genet. 17, 155-90 (1983).
Goodier and Kazazian, Retrotransposons revisited: the restraint and rehabilitation of parasites. Cell 135, 23-35 (2008).
Goodier et al., A novel active L1 retrotransposon subfamily in the mouse. Genome Res. 11, 1677-85 (2001).
Greer et al., DNA Methylation on N6-Adenine in C. elegans. Cell 161, 868-878 (2015).
Harris et al., Comparison of sequencing-based methods to profile DNA methylation and identification of monoallelic epigenetic modifications. Nat. Biotechnol. 28, 1097-105 (2010).
Heyn and Esteller, An Adenine Code for DNA: A Second Life for N6-Methyladenine. Cell 161, 710-713 (2015).
Jia et al., N6-methyladenosine in nuclear RNA is a major substrate of the obesity-associated FTO. Nat. Chem. Biol. 7, 885-7 (2011).
Jin and Felsenfeld, Nucleosome stability mediated by histone variants H3.3 and H2A.Z. Genes Dev. 21, 1519-29 (2007).
Kanellopoulou et al., Dicer-deficient mouse embryonic stem cells are defective in differentiation and centromeric silencing. Genes Dev. 19, 489-501 (2005).
Koziol et al., Identification of methylated deoxyadenosines in vertebrates reveals diversity in DNA modifications. Nature Struct Mol Biol. 23:24-30 (2016).
Langmead et al., Ultrafast and memory-efficient alignment of short DNA sequences to the human genome. Genome Biol. 10:R25 (2009).
Liu et al., A possible role of Reproductive Homeobox 6 in primordial germ cell differentiation. Int J Dev Biol. 55:909-916 (2011).

Lu et al., Distribution of DNA adducts caused by inhaled formaldehyde is consistent with induction of nasal carcinoma but not leukemia. Toxicol Sci. 116:441-451 (2010).
Luger et al., Crystal structure of the nucleosome core particle at 2.8 A resolution. Nature 389, 251-60 (1997).
Lyon, X-chromosome inactivation: a repeat hypothesis. Cytogenet Cell Genet. 80:133-137 (1998).
Malik and Henikoff, Phylogenomics of the nucleosome. Nat. Struct. Biol. 10, 882-91 (2003).
Moran et al., High frequency retrotransposition in cultured mammalian cells. Cell 87, 917-27 (1996).
Müller et al., ALKBH1 is dispensable for abasic site cleavage during base excision repair and class switch recombination. PLoS One 8, e67403 (2013).
Nordstrand et al. Mice lacking Alkbh1 display sex-ratio distortion and unilateral eye defects. PLoS One 5, e13827 (2010).
Orkin and Hochedlinger, Chromatin connections to pluripotency and cellular reprogramming. Cell 145, 835-50 (2011).
Ougland et al., ALKBH1 is a histone H2A dioxygenase involved in neural differentiation. Stem Cells 30, 2672-82 (2012).
Ratel et al., Undetectable levels of N6-methyl adenine in mouse DNA: Cloning and analysis of PRED28, a gene coding for a putative mammalian DNA adenine methyltransferase. FEBS Lett. 580, 3179-84 (2006).
Ratel et al., N6-methyladenine: the other methylated base of DNA. Bioessays 28, 309-15 (2006).
Schübeler, Function and information content of DNA methylation. Nature 517, 321-326 (2015).
Sedgwick, Repairing DNA-methylation damage. Nat. Rev. Mol. Cell Biol. 5, 148-57 (2004).
Shen et al., Mechanism and function of oxidative reversal of DNA and RNA methylation. Annu. Rev. Biochem. 83, 585-614 (2014).
Smith and Meissner, DNA methylation: roles in mammalian development. Nat. Rev. Genet. 14, 204-20 (2013).
Song and Smith, Identifying dispersed epigenomic domains from ChIP-seq data. Bioinformatics. 2011;27:870-871 (2011).
Songe-Møller et al., Mammalian ALKBH8 possesses tRNA methyltransferase activity required for the biogenesis of multiple wobble uridine modifications implicated in translational decoding. Mol. Cell. Biol. 30, 1814-27 (2010).
Tackett et al., I-DIRT, a general method for distinguishing between specific and nonspecific protein interactions. J Proteome Res. 4:1752-1756 (2005).
Tomomori-Sato et al., Immunoaffinity purification of protein complexes from mammalian cells. Methods Mol Biol. 977:273-287 (2013).
Trapnell et al., TopHat: discovering splice junctions with RNA-Seq. Bioinformatics, 25:1105-1111 (2009).
Trapnell et al., Differential gene and transcript expression analysis of RNA-seq experiemtns with TopHat and Cufflinks, Nat Protoc. 7:562-78 (2013).
Venolia and Gartler, Comparison of transformation efficiency of human active and inactive X-chromosomal DNA. Nature 302, 82-3 (1983).
Wu et al., Histone Variant H2A.X Deposition Pattern Serves as a Functional Epigenetic Mark for Distinguishing the Developmental Potentials of iPSCs. Cell Stem Cell 15, 281-294 (2014).
Zang et al., A clustering approach for identification of enriched domains from histone modification ChIP-seq data. Bioinformatics. 2009;25:1952-1958 (2009).
Zhang et al., N6-Methyladenine DNA Modification in *Drosophila*. Cell 161, 893-906 (2015).
Zheng et al., ALKBH5 is a mammalian RNA demethylase that impacts RNA metabolism and mouse fertility. Mol. Cell 49, 18-29 (2013).

* cited by examiner

A. Overlap with known H2A.X-deposition regions in ESCs

B.

| SMRT sequence coverage (WT) | # of As (sequenced) | Mod bases QV | # of N6-mA Sites (coverage and QV criterion) |
|---|---|---|---|
| > 10 X | 4697753 | >= 20 | 595 |
| > 20 X | 707163 | >= 20 | 1866 |
| > 25 X | 272592 | >= 20 | 1108 |
| > 30 X | 113837 | >= 20 | 709 |
| > 30 X | 113837 | >= 20 | 398 |

```
                            SEQUENCE LISTING

<160> NUMBER OF SEQ ID NOS: 82

<210> SEQ ID NO 1
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 1
accgagtgcc tctggcatcc cggg                                              24

<210> SEQ ID NO 2
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 2 aaacccggg atgccagagg cact                                               24

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
aggcagattt ctgagttcaa gg                                                22
```

<210> SEQ ID NO 4
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 4
tttagtcatg tgcttgtcca gg                                    22

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 5
tcccactctt ccaccttcga tgc                                   23

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 6
gggtctggga tggaaattgt gagg                                  24

<210> SEQ ID NO 7
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 7
gcaggagcac gagtggaaag caac                                  24

<210> SEQ ID NO 8
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 8
caaggcctcg aagcgacaga tg                                    22

<210> SEQ ID NO 9
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 9
aggctttgga gacagtgagg tgc                                   23

<210> SEQ ID NO 10
<211> LENGTH: 23
<212> TYPE: DNA
<213> ORGANISM: Artificial Sequence
<220> FEATURE:
<223> OTHER INFORMATION: Chemically Synthesized

```
<400> SEQUENCE: 10
taccctcaaa ctcctggtcc ttc                                              23

<210> SEQ ID NO 11
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 11
cgtgctcttt aacccagacc t                                                21

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 12
tccatgctga ctgcaccaat                                                  20

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13
ctggctcaac tgcggtacag                                                  20

<210> SEQ ID NO 14
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 14
accaattctg cacatcacat tca                                              23

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 15
gggggaaatg tccgaaggaa a                                                21

<210> SEQ ID NO 16
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 16
cctgcactac aaatctccca ac                                               22

<210> SEQ ID NO 17
```

```
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 17
ctggttagcc tcagggaagc                                              20

<210> SEQ ID NO 18
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 18
gccacctctc gaaggttctg                                              20

<210> SEQ ID NO 19
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 19
cgatgaccga ggaacaggtc                                              20

<210> SEQ ID NO 20
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 20
gcctgccacc tctcgaaaat                                              20

<210> SEQ ID NO 21
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 21
aaggcggaca ggaacatcag                                              20

<210> SEQ ID NO 22
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 22
cagcatgaat acagtggagt ctc                                          23

<210> SEQ ID NO 23
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 23
```
ggacacaatg aaagcatttc taagag                                          26

<210> SEQ ID NO 24
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 24
gggtgttagc agagaagaac g                                               21

<210> SEQ ID NO 25
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 25
gttctgtgac tcctgaaaat gca                                             23

<210> SEQ ID NO 26
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 26
gagtgcctga aactgggctt a                                               21

<210> SEQ ID NO 27
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 27
cactcccacc ccacctagt                                                  19

<210> SEQ ID NO 28
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 28
taactcttta gcagtgctct cctgt                                           25

<210> SEQ ID NO 29
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 29
agcttctgga acaggcagaa                                                 20

<210> SEQ ID NO 30
<211> LENGTH: 20
<212> TYPE: DNA

<213> ORGANISM: Artificial Sequence
<220> FEATURE:
<223> OTHER INFORMATION: Chemically Synthesized

<400> SEQUENCE: 30
cactgtgttg ctttggcagt                                              20

<210> SEQ ID NO 31
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 31
ggtgtggtgg cgcacacc                                                18

<210> SEQ ID NO 32
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 32
cctggctgtc ctggagctc                                               19

<210> SEQ ID NO 33
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 33
ctgccttcag acacaccaga ag                                           22

<210> SEQ ID NO 34
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 34
gatggaagag gttttgccaa g                                            21

<210> SEQ ID NO 35
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 35
gtccctagga agccaagtga a                                            21

<210> SEQ ID NO 36
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 36
ttggctctgc ggttctgaaa                                              20

<210> SEQ ID NO 37
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 37
tttaaaccgc catgcactcg                                              20

<210> SEQ ID NO 38
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 38
cacggaagag tagccctcgg                                              20

<210> SEQ ID NO 39
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 39
acaccccaat ctcgatatgt ttga                                         24

<210> SEQ ID NO 40
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 40
attgcacagg tagtgtcccg                                              20

<210> SEQ ID NO 41
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 41
ctcaggggta ggggcatca                                               19

<210> SEQ ID NO 42
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 42
cctccttgcc tcttggtagc                                              20

<210> SEQ ID NO 43
<211> LENGTH: 20
<212> TYPE: DNA
<213> ORGANISM: Artificial Sequence
<220> FEATURE:

<223> OTHER INFORMATION: Chemically Synthesized

<400> SEQUENCE: 43
ctacccggat ggcaaagtca                                          20

<210> SEQ ID NO 44
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 44
tccgtaaatt tggcacttgc at                                       22

<210> SEQ ID NO 45
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 45
gcacatgcaa acacacatga                                          20

<210> SEQ ID NO 46
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 46
acttggacgg gaactgacac                                          20

<210> SEQ ID NO 47
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 47
aagactcctg gaaggtggag ag                                       22

<210> SEQ ID NO 48
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 48
catcctcctg ccgttcttgg t                                        21

<210> SEQ ID NO 49
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 49
aggagcacta cactgacctg a                                        21

```
<210> SEQ ID NO 50
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 50
ggttggtctc tccaagcatc a                                              21

<210> SEQ ID NO 51
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 51
tgggcctaca agtgctatct g                                              21

<210> SEQ ID NO 52
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 52
ttctcaaaag tgagtcaccc ac                                             22

<210> SEQ ID NO 53
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 53
ttcggaacaa attagtcagg tgc                                            23

<210> SEQ ID NO 54
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 54
agtgcattac ctctttcatg gtg                                            23

<210> SEQ ID NO 55
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 55
ggagacctta ccacttgaag atg                                            23

<210> SEQ ID NO 56
<211> LENGTH: 22
<212> TYPE: DNA
<213> ORGANISM: Artificial Sequence
<220> FEATURE:
<223> OTHER INFORMATION: Chemically Synthesized
```

<400> SEQUENCE: 56
gcccggaacc tatctatcct ct                                             22

<210> SEQ ID NO 57
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 57
aaggggtgaa ccttcagcg                                                 19

<210> SEQ ID NO 58
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 58
gcccaccaag atttgggtct c                                              21

<210> SEQ ID NO 59
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 59
cacagcctac agggcattg                                                 20

<210> SEQ ID NO 60
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 60
ttggcagcga tttcaagagt c                                              21

<210> SEQ ID NO 61
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 61
tctgggtatg tggtacactg at                                             22

<210> SEQ ID NO 62
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 62
aggggttcgt gctagagtct c                                              21

<210> SEQ ID NO 63
<211> LENGTH: 20

```
<212> TYPE: DNA
<213> ORGANISM: Artificial Sequence
<220> FEATURE:
<223> OTHER INFORMATION: Chemically Synthesized

<400> SEQUENCE: 63
gcagccctct caaccagttc                                              20

<210> SEQ ID NO 64
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 64
ttctttccga gctacccta a                                             21

<210> SEQ ID NO 65
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 65
atgtctactg tccacgaaat cct                                          23

<210> SEQ ID NO 66
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 66
cgaagttggt gtagggtttg act                                          23

<210> SEQ ID NO 67
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 67
ggactcgccg cctatgttc                                               19

<210> SEQ ID NO 68
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 68
cgttaagcat gtactcgcat ttg                                          23

<210> SEQ ID NO 69
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 69
```
catccacttc taccccacct t                                              21

<210> SEQ ID NO 70
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 70
agctccctgt caggtcctt                                                 19

<210> SEQ ID NO 71
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 71
agcaactggt ttgtgaggtg tccggtgac                                      29

<210> SEQ ID NO 72
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 72
ctccccaatc ccaccctcta gccttgac                                       28

<210> SEQ ID NO 73
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 73
cagactggga gggagggaaa                                                20

<210> SEQ ID NO 74
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 74
gaggtgcagc cgtggttaaa                                                20

<210> SEQ ID NO 75
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 75
cttgcgtgcg cattcagtat                                                20

<210> SEQ ID NO 76
<211> LENGTH: 20
<212> TYPE: DNA
<213> ORGANISM: Artificial Sequence

```
<220> FEATURE:
<223> OTHER INFORMATION: Chemically Synthesized

<400> SEQUENCE: 76
tgcttcgcgc tcatcagtag                                               20

<210> SEQ ID NO 77
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 77
actgcggtac atagggaagc                                               20

<210> SEQ ID NO 78
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 78
tgtgatccac tcaccagagg                                               20

<210> SEQ ID NO 79
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 79
gctgttgccc cttcccctcc                                               20

<210> SEQ ID NO 80
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 80
cctgcgggcg tgggttgag                                                19

<210> SEQ ID NO 81
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 81
tatccacatg accgacagcg                                               20

<210> SEQ ID NO 82
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 82
ccccaaatcg ggacagactc                                               20
```

COMPOSITIONS AND METHODS FOR DETECTING N⁶-METHYLADENINE IN THE MAMMALIAN GENOME

CROSS-REFERENCE TO RELATED APPLICATIONS

This application is a U.S. national phase application filed under 35 U.S.C. § 371 claiming benefit to PCT International Patent Application No. PCT/US2017/022747, filed on Mar. 16, 2017, which claims priority to U.S. Provisional Application No. 62/309,093, filed Mar. 16, 2016, each of which disclosures is incorporated herein by reference in its entirety.

STATEMENT REGARDING FEDERALLY SPONSORED RESEARCH OR DEVELOPMENT

This invention was made with government support under Grant No. 1R01GM114205-01, awarded by National Institutes of Health. The Government has certain rights in the invention.

BACKGROUND OF THE INVENTION

DNA methylation is a crucial component of epigenetic regulation that controls many important aspects of mammalian biology, such as imprinting, X chromosome inactivation and tumorigenesis (Venolia and Gartler, 1983, Nature 302: 82-3; Bell and Felsenfeld, 2000, Nature 405:482-5; Smith and Meissner, 2013, Nat Rev Genet 14:204-20; Schubeler, 2015, Nature 517:321-6). The prevailing dogma states that DNA methylation exclusively occurs on the fifth position of cytosine (5mC) in mammals, whereas the other modifications are absent, such as $N^6$-methyladenine (N6-mA) which is predominantly present in prokaryotes and a limited number of eukaryotes (Heyn and Esteller, 2015, Cell 161:710-3). Several reports have very recently expanded the list of organisms with N6-mA to three additional eukaryotes: insects (*D. melanogaster*) (Zhang et al., 2015, Cell 161:893-906), nematodes (*C. elegans*) (Greer et al., 2015, Cell 161:868-78) and green algae (*C. reinhardtii*) (Fu et al., 2015, Cell 161:879-92). Despite this progress, the central issue regarding additional DNA modifications in mammals remains unsolved. A single report in 1980's showed indirect evidence of N6-mA in mammalian genomes (Achwal et al., 1983, FEBS Lett 158:353-8); subsequent studies, however, were unable to confirm the presence of N6-mA in mammalian genomes (Ratel et al., 2006, FEBS Lett 580:3179-84). It was therefore determined that the abundance of N6-mA must be extremely low in mammalian genomes, if at all existent (Heyn and Esteller, 2015, Cell 161:710-3; Ratel et al., 2006, Bioessays 28:309-15) and that N6-mA might have been excluded from mammalian genomes during evolution. SMRT (Single Molecular Real-Time) sequencing, which can distinguish modified bases via differential DNA polymerase kinetics during synthesis, has recently been applied to identify DNA modifications in a variety of organisms (Davis et al., 2013, Curr Opin Microbiol 16:192-8). Although this approach has greatly facilitated the identification of N6-mA in various eukaryotes, high sequencing coverage is needed for precise calling of a modified base, which presents a unique hurdle for adapting SMRT sequencing to interrogating the large genomes of mammals (2.8 Gb of *Mus musculus*, for example).

DNA methylation (5mC) is primarily involved in gene silencing in mammalian cells, while N6-mA is implicated in gene activation in insects (*D. melanogaster*) (Zhang et al., 2015, Cell 161:893-906); and N6-mA also collaborates with H3K4 methylation in worms (*C. elegans*) (Greer et al., 2015, Cell 161:868-78). In addition to repressing the expression of genes, a major function of 5mC in mammals is to control retrotransposons, which comprise nearly half of the mammalian genome (Goodier and Kazazian, 2008, Cell 135:23-35). For example, the long interspersed element 1 (LINE1 or L1), a non-LTR family retrotransposon, is repressed by 5mC and small RNAs, especially in the germline (Goodier and Kazazian, 2008, Cell 135:23-35; Bourc'his and Estor, 2004, Nature 431:96-9; Kanellopoulou, 2005, Genes Dev 19:489-501). Several thousands of full-length LINE1s (6-7 Kb), which contain their own promoters at the 5'UTR, can transcribe autonomously, while the majority of the LINE1s, which lost the 5' UTR and other regions proximal to the 5' end, such as the open reading frame 1 (ORF1), are transcriptionally incompetent (Goodier and Kazazian, 2008, Cell 135:23-35). Although generally considered "junk DNAn," LINE1s, especially, the full-length ones, have been long proposed to play a role in the regulation of high-order chromatin structure and long-range gene silencing. Mary Lyon (Lyon, 1998, Cytogenet Cell Genet 80:133-7) first proposed that LINE1 may serve as the "way stations" (Gartler and Riggs, 1983, Annu Rev Genet 17:155-90) to facilitate heterochromatinization on the inactive X chromosomes in female cells because LINE1s, especially the young (emerged in the mouse genome less than 1.5 million years ago (Goodier and Kazazian, 2008, Cell 135:23-35; Goodier et al., 2001, Genome Res 11:1677-85; Castro-Diaz et al., 2014, Genes Dev 28:1397-409)) full-length L1s are specifically enriched on the X-chromosome over the autosomes (Abrusán et al., 2008, PLoS Genet 4:e1000172; Bailey et al., 2000, PNAS 97:6634-9). Subsequent bioinformatics analysis and experimental evidence both indicate that young full-length L1s may be involved in the propagation of heterochromatin during X-inactivation (Abrusán et al., 2008, PLoS Genet 4:e1000172; Bailey et al., 2000, PNAS 97:6634-9; Chow et al., 2010, Cell 141:956-69). However, it is still debatable whether young full-length L1s plays any direct roles in epigenetic silencing.

Accumulating evidence has demonstrated the vital role of histone proteins in regulating DNA functions. Histone octamers form the core complex that stabilizes nucleosome structures via an intricate web of interactions with DNA (Baillie et al., 2011, Nature 479:534-7); the primary sequences of histones are highly conserved in evolution, as alteration may destabilize histone-DNA interactions (Luger et al., 1997, Nature 389:251-60). On the other hand, incorporation of histone variant proteins, which carry significantly different primary sequences from the major histone isoforms, is another important aspect of epigenetic regulation (Banaszynski et al., 2010, Dev Cell 19:662-74; Malik and Henikoff, 2003, Nat Struct Biol 10:882-91). These variants, which usually account for a very small fraction of the total histone pool, are deposited in critical genomic regions and play important roles in cell fate decisions and development (Banaszynski et al., 2010, Dev Cell 19:662-74; Malik and Henikoff, 2003, Nat Struct Biol 10:882-91). For example, recent work has demonstrated an unexpected role of H2A.X, a H2A variant, in determining the cell fate transition of embryonic stem cells (ESCs) and the quality of induced pluripotent stem cells (iPSCs) (Wu et al., 2014, Cell Stem Cell 15:281-94; Buganim et al., 2014, Cell Stem Cell 15:295-309). It has been shown that the local structure of histone variant-containing nucleosomes may be different from the canonical ones, consistent with the significant differences in protein (histone) primary sequences (Jin and Felsenfeld, 2007, Genes Dev 21:1519-29). By the same token, it is conceivable that the altered nucleosome structures may be employed in accommodating variations in DNA structures, such as chemical modifications.

Therefore, there is a long-felt need in the art for methods to detect DNA modifications in mammalian cells. The present invention fulfills this need.

SUMMARY OF THE INVENTION

In one aspect, the invention provides a method of detecting a modified nucleic acid in a sample. In one embodiment, the method comprises isolating DNA from a sample to obtain isolated DNA; sequencing the isolated DNA; and analyzing the isolated DNA sequence to detect the nucleic acid modification.

In one embodiment, isolating DNA from a sample further comprises subjecting the sample to chromatin-immunoprecipitation (ChIP) to obtain the isolated DNA. In one embodiment, the isolated DNA is from a genomic region. In one embodiment, the genomic region is an H2A.X deposition region. In one embodiment, isolating DNA from a sample further comprises subjecting the sample to DNA-immunoprecipitation (DIP) to obtain the isolated DNA.

In one embodiment, sequencing the isolated DNA further comprises subjecting the isolated DNA to singular molecular real time (SNRT) sequencing. In one embodiment, the method further comprises circularizing the isolated DNA. In one embodiment, sequencing the isolated DNA further comprises subjecting the isolated DNA to next generation sequencing.

In one embodiment, the nucleic acid modification is $N^6$-methyladenine (N6-mA).

In one embodiment, the sample is a biological sample. In one embodiment, the biological sample is a stem cell. In one embodiment, the stem cell is one selected from the group consisting of an embryonic stem cell and an induced pluripotent stem cell.

In another aspect, the invention provides a method for diagnosing cancer in a subject in need thereof. In one embodiment, the method comprises determining the level of N6-mA in a biological sample of the subject; measuring the level of N6-mA of a comparator control; and diagnosing the subject with cancer when the level of N6-mA in the biological sample is different than the level of N6-mA of the comparator control.

In one embodiment, the level of N6-mA in the biological sample is elevated when compared with the comparator control. In one embodiment, the level of N6-mA in the biological sample is reduced when compared with the comparator control.

In one embodiment, the comparator control is at least one selected from the group consisting of: a positive comparator control, a negative comparator control, a historical control, a historical norm, or the level of a reference molecule in the biological sample. In one embodiment, the subject is human.

In one aspect, the invention provides method for modulating the level of N6-mA in a sample. In one embodiment, the method comprises administering a modulator of ALKBH1 to the sample.

In one embodiment, the modulator is at least one selected from the group consisting of a chemical compound, a protein, a peptide, a peptidomemetic, an antibody, a ribozyme, a small molecule chemical compound, a nucleic acid, a vector, an antisense nucleic acid molecule.

In one embodiment, the modulator decreases the level or activity of ALKBH1. In one embodiment, the modulator increases the level or activity of ALKBH1. In one embodiment, the level of N6-mA is increased. In one embodiment, the level of N6-mA is decreased.

In another aspect, the invention provides a composition comprising a modulator of N6-mA. In one embodiment, the composition comprises an agent selected from the group consisting of an inhibitor of ALKBH1 and an activator of ALKBH1.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the schematics of SMRT-ChIP. FIG. 1B depicts sequencing tracks of N6-mA in ESCs. FIG. 1C depicts LC-Mass Spectrometry analysis of N6-mA (m/z 266.1 to m/z 150.1). and stable isotope labeled N6-mA (m/z 271.1 to m/z 155.1), internal standard.

FIG. 1D depicts quantification of the LC-MS/MS results. P<0.01, t-test; Error bars, ±the S.E.M. of three biological replicates.

FIG. 2, comprising FIG. 2A depicts mass spectrometry analysis of N6-mA in Alkbh1 KO ESCs (P value determined by t-tests). FIG. 2B depicts dot blotting of N6-mA in Alkbh1 KO or WT ESCs (in triplicates). FIG. 2C depicts in vitro demethylation reaction with recombinant ALKBH1 proteins monitored by dot blotting. FIG. 2D depicts quantification of demethylation activity in three independent demethylase assays (P value <5.0E-05, t-test). FIG. 2E depicts in vitro demethylation reaction monitored by Mass Spectrometry (P value <0.01, t-test). Error bars, S.D. for three biological replicates.

FIG. 3, comprising FIG. 3A depicts RNA-seq analysis of Alkbh1 KO ESCs vs WT controls. blue: top downregulated genes, red: upregulated genes (false positives). FIG. 3B depicts downregulated genes were most enriched on X chromosome (P<0.01, Binomial test) and Chr13 to a lesser extent (P<0.05, Binomial test). FIG. 3C depicts qRT-PCR analysis of downregulated genes (*, p<0.05, t-test). FIG. 3D depicts RT-qPCR of transposon expression (*, p<0.01, t-test). L1Md-Gf-X: a young full-length L1 on Chr-X. L1Md-Gf-17: a young full-length L1 on Chr17. Error bars: ±the S.E.M. of three technical replicates.

FIG. 4, comprising FIG. 4A depicts enrichment of N6-mA on full-length L1s (P value determined by t-test). FIG. 4B depicts relative enrichment of N6-mA peaks on each chromosome (P=1.4E-322, Binomial test) and relative enrichment of young full-length L1s on each chromosome. FIG. 4C depicts normalized frequency of full-length L1s was plotted as a function of their genomic distance to downregulated genes (red, N6-mA enriched, median: 424 kb; gray, non-enriched, median: 1.6 Mb). FIG. 4D depicts the Dax1 gene locus.

FIG. 5, comprising FIG. 5A depicts aggregation of 5mC. FIG. 5B depicts aggregation of H3K9Me3 signals. FIG. 5C depicts normalized frequency of decommissioned enhancers was plotted as a function of their genomic distance to full-length L1s red, N6-mA enriched, median: 484 Kb; gray, non-enriched, median: 2 Mb. FIG. 5D depicts RT-qPCR analysis of the Gm8817 and Rhox6 gene (on the X-chromosome) during EB differentiation. * P<0.05, t-test; Error bars, ±the S.E.M. of three biological replicates. FIG. 5E depicts schematics of Alkbh1 and N6-mA functions.

FIG. 6, comprising FIG. 6A depicts a majority of N6-mA peaks identified by SMRT-ChIP is located in H2A.X deposition region in ESCs determined by native ChIP. FIG. 6B depicts the number of SMRT-ChIP N6 mA sites at different coverage and QV cut-off. FIG. 6C depicts a DNA motif of H2A.X deposition region determine with standard ChIP-Seq and sequence motifs for N6-mA peaks at H2A.X deposition regions determined with SMRT-ChIP. FIG. 6D depicts the distribution of N6-mA peaks at H2A.X deposition regions. (P value determined by Binomial test).

FIG. 7, comprising FIG. 7A depicts the experimental workflow for determining N6-mA level with LC-MS/MS. [N5]-N6-mA was used as Internal Standard. FIG. 7B depicts results showing N6-mA levels are ultralow in adult tissues. FIG. 7C depicts results showing no detection of DNA alkylation adducts, such as N1-mA, N3-mA or N3-mC in mouse ES cells or Alkbh1 KO cells by MS. FIG. 7D depicts LC-MS/MS analysis of N1-mA or N6-mA digested from synthetic oligonucleotides and ES cell DNA samples. FIG. 7E depicts ESI-QTOF-MS/MS spectra of analytical standard of N6-mA nucleosides and N6-mA containing HPLC fraction from ES cells.

FIG. 8, comprising FIG. 8A depicts Schematics of CRSPR/Cas9 approach. Alkbh1 KO alleles do not contain the Xma1 site at Exon3. The PCR-DNA digestion approach showed the homozygosity of the KO alleles, which are resistant to Xma1 digestion. Western blotting didn't detect any ALKBH1 proteins in the KO cells. FIG. 8B depicts dot blotting results demonstrating three additional Alkbh1 KO ESC clones show similar levels of N6-mA upregulation. FIG. 8C depicts experiments validating the specificity of anti-N6-mA antibodies with synthetic oligonucleotides. FIG. 8D depicts experiments validating of anti-N6-mA antibodies with DNA samples of different N6 mA/dA ratio. 125 ng of genomic DNA (MEFs) which don't contain any endogenous N6-mA were spiked with N6-mA containing oligonucleotides at indicated concentration. FIG. 8E depicts tandem mass spectrometric analysis showing the lack of H2AK118/119 methylation in WT or Alkbh1 KO ESCs. Spectral counts for H2A peptides containing K118/119 revealed that H2AK118/119 is predominately non-methylated at similar levels between wild-type and Alkbh1 KO ESCs. Spectral counts are reported as an average with standard deviation from biological triplicate analyses. K118/119: no methylation; K118/119me1: K118/119 monomethylation. FIG. 8F depicts MS analysis showing that the co-purified factors with recombinant ALKBH1 proteins are mainly heat shock proteins. FIG. 8G depicts experimental results demonstrating ALKBH1 proteins don't have noticeable activities towards to dual- or hemi-methylated double-stranded oligonucleotide substrates. FIG. 8H depicts experimental results demonstrating ALKBH1 activities are dependent on Fe and α-KG. Error bars: standard deviation of triplicates. FIG. 8I depicts ectopic expression of WT, but not mutant Alkbh1 (D233A) at the catalytic motif, can rescue the aberrant increase of N6-mA level in Alkbh1 KO ESCs. The WT and mutant Alkbh1 were expressed at similar levels. FIG. 8J depicts quantification of three independent rescue experiments. (P value as labeled, determined by t-test; Error bars: S.D. for three biological replicates). FIG. 8K depicts the demethylation activity of N6-mA by recombinant D233A mutant protein is much reduced in comparison with the WT counterpart. FIG. 8L depicts experimental results demonstrating no significant activities were detected with increasing concentrations of recombinant D233A mutant proteins in demethylation reaction. Error bars: standard deviation of triplicates.

FIG. 9, comprising FIG. 9A depicts RT-qPCR validation of the RNA-Seq analysis. Unchanged genes (gene names labeled in black) identified by RNA-Seq were unaltered in RT-qPCR analysis. Highly repressed (red), or modestly repressed (green) genes identified by RNA-Seq also showed expected levels of repression in RT-qPCR analyses. Of note, the genes (blue) identified as upregulated in RNA-Seq; however, they don't show differential expression (no significance) in RT-qPCR analysis, which further confirmed the suppression function of ALKBH1. Error bars: standard deviation of triplicates. FIG. 9B depicts MA plot of RNA-Seq analyzed by DESeq2, which shows the similar pattern to that of CuffDiff2. FIG. 9C depicts gene ontology analysis demonstrated that lineage specifying factors involved in embryonic development are greatly downregulated by Alkbh1 deficiency. FIG. 9D depicts RNA-Seq transcripts of the representative subfamilies in three major retrotransposon superfamilies (LINE, SINE and LTR) in Alkbh1 KO ESCs.

FIG. 10, comprising FIG. 10A through FIG. 10H depicts the validation of N6-mA DIP-Seq approach. FIG. 10A depicts "spike-in" experiments for determining the threshold and linear response range of N6-mA DIP. Genomic DNAs were spiked with N6-mA containing oligonucleotides at indicated concentration (X-axis). After N6-mA DIP, the relative enrichment of N6-mA over input control was determined by a RT-qPCR approach. Blue line: linear regression based on data points between 20 ppm-130 ppm. The threshold (the red line) is the background signals detected by RT-qPCR in which unmodified (control) oligonucleotides were spiked in.

FIG. 11, comprising FIG. 11a depicts aggregation plot shows that signal intensity of N6-mA at young full-length L1 is enriched at the 5' UTR and ORF1. FIG. 11B depicts qPCR analysis of N6-mA DIP samples confirmed the enrichment at the 5'UTR and ORF1 regions of L1 that are retained in the young full-length L1s, but not the 3'UTR or Nanog promoter.

FIG. 12, comprising FIG. 12A depicts violin diagram of the density distribution of the distance between L1 and down-regulated genes in Alkbh1 KO cells. FIG. 12B depicts the distances between ESC-expressing genes in Alkbh1 KO ES cells and young full-length L1s plotted for indicated chromosomes. FIG. 12C depicts the distances between down-regulated genes in Alkbh1 KO ES cells and young full-length L1s plotted for indicated chromosomes.

FIG. 13, comprising FIG. 13A depicts normalized 5mC levels on gene bodies or promoters in WT or Alkbh1 KO ESCs. FIG. 13B depicts histone marks (H2A.X or H3K27Me3) or 5mC levels on young full-length L1s, SINE or LTR transposons. FIG. 13C depicts Representative sequencing tracks of decommissioned enhancers. Note that H3K27Ac and H3K4me1 levels at this locus are greatly downregulated in Alkbh1 KO ESCs. FIG. 13D depicts a violin diagram shows the density distribution of the distance between L1 and decommissioned enhancers in Alkbh1 KO cells. FIG. 13E depicts the ChIP-qPCR approach demonstrating that H3K4me3 levels are decreased at the transcription start sites (TSS) of LINE-1 or Dax1, an X-chromosome gene, while unchanged at the control gene TSS. (* P<0.01, t-test; Error bars, ±the S.E.M. of three technical triplicates).

FIG. 14, comprising FIG. 14A depicts results demonstrating at day 9, Nanog expression is reduced significantly in WT-ESC derived EBs as expected, while its level in Alkbh1 KO ESC-derived EBs is still high. FIG. 14B depicts results demonstrating Lefty-1 and Lefty-2 are repressed at Day 1 or 9 in Alkbh1 KO ESC-derived EBs. FIG. 14C depicts results demonstrating activation of Cdx2, is insufficient in Alkbh1 KO ESC-derived EBs. FIG. 14D depicts results demonstrating expressions of other endoderm markers, Foxa2, Gata4, Gata6, are significantly higher in Alkbh1 KO ESC-derived EBs than WT ESC-derived EBs. FIG. 14E depicts results demonstrating ectoderm markers, Fgf5 and Pax6 are transiently (day 1) overexpressed in Alkbh1 KO ESC-derived EBs.

DETAILED DESCRIPTION

Figures 1A, 1B, 1C, 1D:
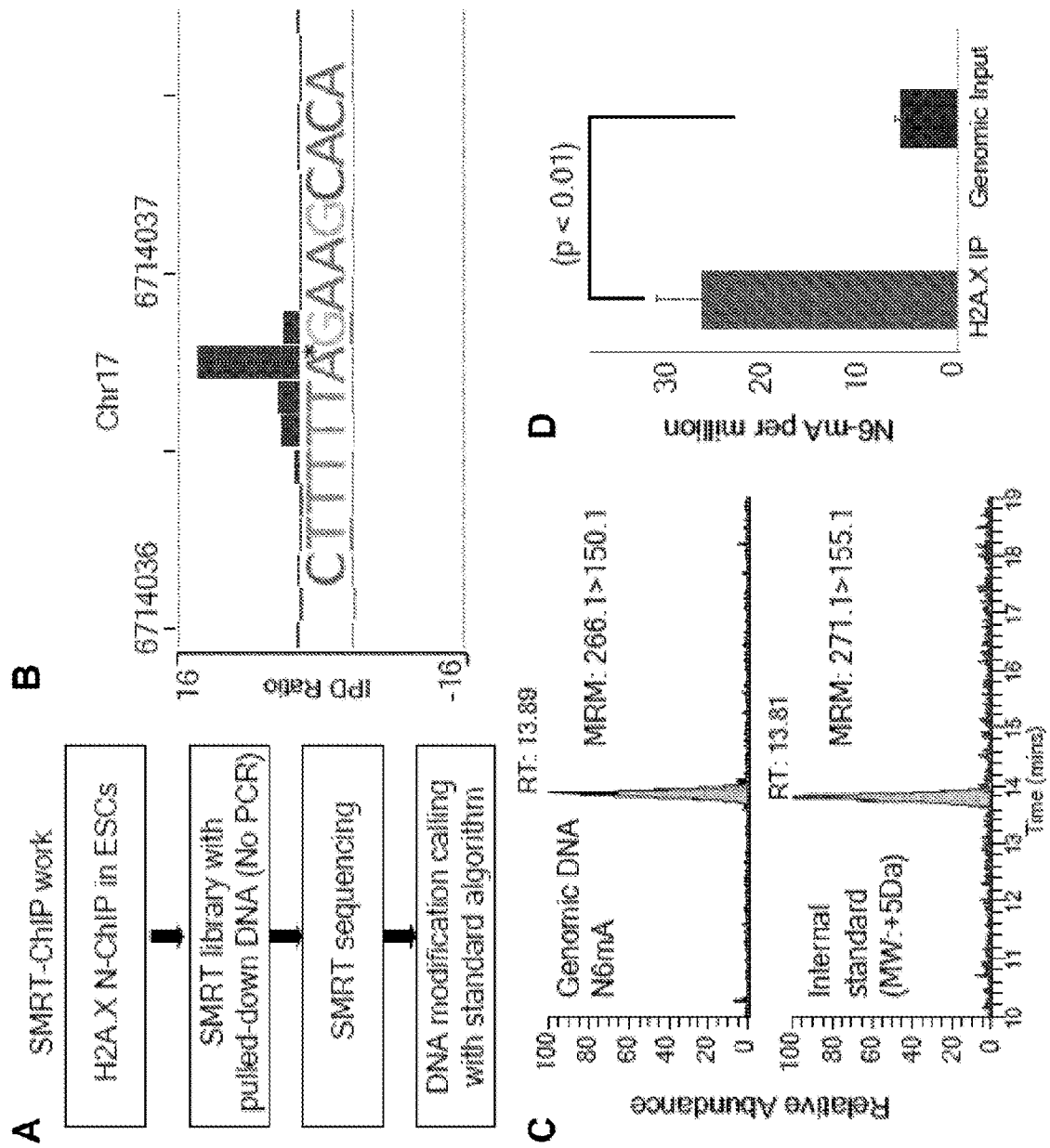
FIG. 1A through 1D, depicts results of experiments demonstrating SMRT-ChIP approach identified N6-mA in mammalian genomes.

The present invention is based, in part, on the discovery that $N^6$-methyladenine (N6-mA) is present in mammalian genomes. For example, it is demonstrated herein that N6-mA constitutes a crucial component of the epigenetic regulation repertoire in mammalian genomes.

The invention is also based, in part, on the identification of Alkbh1 as a major specific demethylase for $N^6$-methyladenine, which is a close homologue to the bacteria DNA demethylase Alkb, but is not able to hydroxylate 5-methylcytosine or demethylate the damage-induced DNA alkylations. For example, it is demonstrated herein that an increase of N6-mA levels in Alkbh1 deficient cells leads to gene silencing.

The invention is also partly based on the discovery that N6-mA, which is undetectable in normal adult tissues, is a novel biomarker for cancer detection in humans.

In some embodiments, the present invention provides methods and kits for identifying N6-mA in a DNA sample. In other embodiments, the invention provides methods and compositions for modulating the levels of N6-mA. In yet another embodiment, the invention provides a method for diagnosing or prognosing cancer in a subject in need thereof using N6-mA as a biomarker.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

The terms "biomarker" and "marker" are used herein interchangeably. They refer to a substance that is a distinctive indicator of a biological process, biological event and/or pathologic condition.

The phrase "body sample" or "biological sample" is used herein in its broadest sense. A sample may be of any biological tissue or fluid from which biomarkers of the present invention may be assayed. Examples of such samples include but are not limited to blood, saliva, buccal smear, feces, lymph, urine, gynecological fluids, biopsies, amniotic fluid and smears. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological or body samples may also include sections of tissues such as frozen sections taken for histological purposes. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

In the context of the present invention, the term "control," when used to characterize a subject, refers, by way of non-limiting examples, to a subject that is healthy, to a patient that otherwise has not been diagnosed with a disease. The term "control sample" refers to one, or more than one, sample that has been obtained from a healthy subject or from a non-disease tissue such as normal colon.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

"Differentially increased levels" refers to biomarker methylation levels which are at least 1%, 2%, 3%, 4%, 5%, 10% higher or more, for example, 5%, 10%, 20%, 30%, 40%, or 50%, 60%, 70%, 80%, 90% higher or more, and/or 0.5 fold, 1.1 fold, 1.2 fold, 1.4 fold, 1.6 fold, 1.8 fold higher or more, as compared with a control.

"Differentially decreased levels" refers to biomarker methylation levels which are at least at least 1%, 2%, 3%, 4%, 5%, 10% lower or less, for example, 5%, 10%, 20%, 30%, 40%, or 50%, 60%, 70%, 80%, 90% lower or less, and/or 0.9 fold, 0.8 fold, 0.6 fold, 0.4 fold, 0.2 fold, 0.1 fold or less, as compared with a control.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease, or disorder, the frequency with which such a sign or symptom is experienced by a patient, or both, is reduced.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

As used herein "endogenous" refers to any material from or produced inside the organism, cell, tissue or system.

The term "expression" as used herein is defined as the transcription and/or translation of a particular nucleotide sequence driven by its promoter.

The "level" of one or more biomarkers means the absolute or relative amount or concentration of the biomarker in the sample. The term "level" also refers to the absolute or relative amount of methylation of the biomarker in the sample.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand that are located 5' to a reference point on the DNA are referred to as "upstream sequences"; sequences on the DNA strand which are 3' to a reference point on the DNA are referred to as "downstream sequences."

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

A "reference level" of a biomarker means a level of the biomarker, for example level of methylation of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

By the term "specifically binds," as used herein, is meant a molecule, such as an antibody, which recognizes and binds to another molecule or feature, but does not substantially recognize or bind other molecules or features in a sample.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

"Standard control value" as used herein refers to a predetermined methylation level of a biomarker. The standard control value is suitable for the use of a method of the present invention, in order for comparing the amount of methylation of a biomarker of interest that is present in a sample. An established sample serving as a standard control provides an average amount methylation of a biomarker of interest that is typical for an average, healthy person of reasonably matched background, e.g., gender, age, ethnicity, and medical history. A standard control value may vary depending on the biomarker of interest and the nature of the sample.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "subject" refers to a human or another mammal (e.g., primate, dog, cat, goat, horse, pig, mouse, rat, rabbit, and the like). In many embodiments of the present invention, the subject is a human being. In such embodiments, the subject is often referred to as an "individual" or a "patient." The terms "individual" and "patient" do not denote a particular age.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based, in part, on the discovery of the presence of N6-mA in the mammalian genome, the demethylase for N6-mA, and the role of N6-mA in epigenetic regulation in human embryonic stem cells, iPS cells and cancer cells. The present invention is also based on the development of a novel technology to detect DNA modification in mammalian cells.

Accordingly, the invention provides a method for the detection of N6-mA. In one embodiment, N6-mA is identified in a genomic region using SMRT-ChIP (Single Molecular Real-Time sequencing of Chromatin Immunoprecipitation-enriched DNA). In another embodiment, a genomic region having N6-mA is identified using DIP-Seq (DNA Immunoprecipitation—Next generation sequencing) wherein DNA is immunoprecipitated using a N6-mA antibody.

The invention also provides a kit for detecting N6-mA, the kit comprising a reagent to isolate DNA and a reagent to sequence the DNA.

The invention is also based on the discovery that ALKBH1 is the demethylase for N6-mA. Thus, the invention provides methods and compositions for modulating the level of $N^6$-methyladenine.

In one embodiment, the invention is a composition comprising a modulator for modulating the level or frequency of N6-mA. In one embodiment, the modulator is an activator that increases the level or activity of ALKBH1. In another embodiment, the modulator is an inhibitor that decreases level or activity of ALKBH1 expression. In various embodiments the modulator is at least one selected from the group consisting of a chemical compound, a protein, a peptide, a peptidomemetic, an antibody, a ribozyme, a small molecule chemical compound, a nucleic acid, a vector, an antisense nucleic acid molecule.

In one embodiment, the method comprises administering a modulator of ALKBH1. In various embodiments the modulator is at least one selected from the group consisting of a chemical compound, a protein, a peptide, a peptidomemetic, an antibody, a ribozyme, a small molecule chemical compound, a nucleic acid, a vector, an antisense nucleic acid molecule. In one embodiment, the modulator is an activator that increases the level or activity of ALKBH1. In another embodiment, the modulator is an inhibitor that decreases level or activity of ALKBH1 expression.

The invention is also based in part on the discovery that N6-mA is novel biomarker for cancer detection in humans. Thus, the invention provides methods of detecting, diagnosing and prognosing the outcome, of cancer in a subject in need thereof.

In one embodiment, the method comprises determining the level of N6-mA in a biological sample from the subject; comparing the level of N6-mA in the biological sample with a comparator control; and diagnosing or prognosing the subject with cancer when the level of N6-mA in the biological sample is different than the level of N6-mA of the comparator control.

Detection Methods

In one aspect, the invention provides methods of detecting N6-mA. In another aspect, the invention provides methods of measuring the level of N6-mA. In another aspect, the invention provides methods of determining the location of N6-mA. In one embodiment, N6-mA is identified in a genomic region using SMRT-ChIP (Single Molecular Real-Time sequencing of Chromatin Immunoprecipitation-enriched DNA).

In one embodiment, the locations of N6-mA are identified in a genomic region. In one embodiment, the method comprises isolating DNA from a biological sample to obtain a DNA sample; sequencing the DNA sample; and analyzing the DNA sequence to identify a nucleic acid modification. In another embodiment, isolating DNA from a sample further comprises subjecting the sample to chromatin-immunoprecipitation (ChIP) to isolate the DNA sample, wherein the DNA sample is in a genomic region. In some embodiments, the genomic region is an H2A.X deposition region. In another embodiment, the ChIP is performed using an antibody against a histone protein, including, but not limited to, H1, H2A, H2B, H3, H4 and H2A.X.

In one embodiment, sequencing the DNA sample further comprises subjecting the DNA sample to singular molecular real time (SMRT) sequencing. SMRT sequencing systems are applied to the detection of modified nucleic acid templates through analysis of the sequence and/or kinetic data derived from such systems. In particular, modifications in a template nucleic acid strand alter the enzymatic activity of a nucleic acid polymerase in various ways, e.g., by increasing the time for a bound nucleotide to be incorporated and/or increasing the time between incorporation events. In certain embodiments, polymerase activity is detected using a single molecule nucleic acid sequencing technology. In certain embodiments, polymerase activity is detected using a nucleic acid sequencing technology that detects incorporation of nucleotides into a nascent strand in real time. In preferred embodiments, a single molecule nucleic acid sequencing technology is capable of real-time detection of nucleotide incorporation events. Such sequencing technologies are known in the art and include, e.g., the SMRT sequencing and nanopore sequencing technologies. For more information on nanopore sequencing, see, e.g., U.S. Pat. No. 5,795,782; Kasianowicz, et al. (1996) Proc Natl Acad Sci USA 93(24):13770-3; Ashkenas, et al. (2005) Angew Chem Int Ed Engl 44(9):1401-4; Howorka, et al. (2001) Nat Biotechnology 19(7):636-9; and Astier, et al. (2006) J Am Chem Soc 128(5):1705-10, all of which are incorporated herein by reference in their entireties for all purposes.

In yet another embodiment, the method further comprises circularizing the DNA sample. Topologically circular DNA samples allow each base to be read many times by a single sequencing polymerase. Thus, the coverage requirement for modification detection can be achieved both by sequencing different fragments pulled down from the same genomic regions and by sequencing the same fragment with many passes.

In another embodiment, a genomic region having N6-mA is identified using DIP-Seq (DNA Immunoprecipitation—Next generation sequencing). In one embodiment, the method comprises isolating DNA from a sample to obtain a DNA sample; sequencing the DNA sample; and analyzing the DNA sequence to identify a nucleic acid modification. In another embodiment, isolating DNA from a sample further comprises subjecting the sample to DIP to isolate the DNA sample. In one embodiment, the DIP is performed using an antibody against N6-mA. In another embodiment, sequencing the DNA sample further comprises subjecting the DNA sample to next generation sequencing.

In one embodiment, the sample includes, but is not limited to a biological sample, an isolated cell and recombinant nucleic acid sample. In some embodiments, the biological sample includes, but is not limited to, a cancer cell and a stem cell. In another embodiment, the stem cell includes, but is not limited to, an embryonic stem cell (EPC), and an induced pluripotent stem cell (iPSC). In some embodiments, the biological sample includes a cancer cell, such as but is not limited to, a primary cancer cell, a cancer stem cell, or a metastatic cancer cell. Non-limiting examples of cancer cells include acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, wilms tumor.

In one aspect, the invention includes isolating a stem cell from a subject. Therefore, the invention also provides methods of isolating, culturing and expansion of stem cells. In one embodiment the stem cells include, but are not limited to, EPCs, iPSCs, and their progenitor derivatives.

Stem cells of the invention and their progeny can be sterile, and maintained in a sterile environment. Such stem cells, pluralities, populations, and cultures thereof can also be included in a medium.

Kits

In one aspect, the invention provides a kit for detecting N6-mA. In another aspect, the invention provides a kit for measuring the level of N6-mA. In another aspect, the invention provides a kit for determining the location of N6-mA. In one embodiment, the kit of the invention comprises at least one reagent for isolating DNA and at least one reagent for sequencing the DNA.

In one embodiment, the at least one reagent for isolating a DNA sample comprises an antibody against a target, such as, but not limited to, N6-mA, H1, H2A, H2B, H3, H4 and H2A.X. In another embodiment, the at least one reagent for sequencing the DNA includes, but is not limited to, a polymerase, dNTPs, and labeled dNTPs.

In one embodiment, the kit comprises instructions for carrying out and evaluating the described methods of N6-mA methylation analysis.

In a further embodiment, said kit may further comprise standard reagents for performing a N6-mA position-specific methylation analysis.

Biomarker

The present invention provides DNA methylation biomarkers associated with cancer. In one embodiment, N6-mA is a biomarker associated with cancer. Accordingly, a DNA methylation marker associated with cancer is considered a biomarker in the context of the present invention. In one embodiment, the level or frequency of N6-mA is increased in a cancer cell, as compared with a comparator control. In another embodiment, the location of N6-mA is altered in a cancer cell compared, as compared with a comparator control. In one embodiment, N6-mA is overexpressed in ovarian cancer. In another embodiment, the cancer is resistant to chemotherapy. Accordingly, the invention provides methods for identifying one or more biomarkers that can be used to aid in the detection of cancer, diagnosis of cancer, prediction of cancer, prognosis of cancer, and the selection of a particular treatment for cancer.

In some embodiments, the methods of the invention are performed by obtaining a set of measured values for one or more biomarkers from a test biological sample, obtaining a set of measured values for one or more biomarkers from a control or reference biological sample, comparing the measured values for each biomarker between the test and control or reference sample, and identifying biomarkers which are substantially or significantly different in value between the test sample and the control or reference sample.

The process of comparing a measured value and a reference value can be carried out in any convenient manner appropriate to the type of measured value and reference value for the biomarker of the invention. For example, "measuring" can be performed using quantitative or qualitative measurement techniques, and the mode of comparing a measured value and a reference value can vary depending on the measurement technology employed. For example, when a qualitative colorimetric assay is used to measure biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration). In other examples, measured values are qualitative. As with qualitative measurements, the comparison can be made by inspecting the numerical data, or by inspecting representations of the data (e.g., inspecting graphical representations such as bar or line graphs).

A measured value is generally considered to be substantially equal to a reference value if it is about 95-105% of the value of the reference value. A measured value is considered less than a reference value if the measured value is less than about 95% of the reference value. A measured value is considered greater than a reference value if the measured value is at least more than about 5% greater than the reference value.

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a desired biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples.

Methods for screening for the biomarker of the invention are described elsewhere herein. The method for screening the biomarker can find genes that are differentially methylated in cancer as well as at various dysplasic stages of the tissue which progresses to cancer. The screening can be used for cancer screening, risk-assessment, prognosis, disease identification, the diagnosis of disease stages, and can aid in the selection of therapeutic targets and therapies.

The identification of genes that are methylated in cancer and abnormalities at various stages of cancer makes it possible to diagnose cancer at an early stage in an accurate and effective manner and allows methylation assessment of multiple genes and the identification of new targets for therapeutic intervention. Furthermore, the methylation data according to the present invention may be combined with other methylation biomarkers, such as 5mC, or non-methylation related biomarker detection methods for cancer detection and diagnosis.

According to the method of the present invention, the progression of cancer at various stages or phases can be determined by determining the N6-mA methylation status (e.g., level, frequency, location, etc.) of one or more nucleic acid biomarkers obtained from a sample. By comparing the methylation status of a nucleic acid isolated from a sample at each stage of cancer with the methylation status of one or more nucleic acids isolated from a sample in which there is no cell proliferative disorder of tissue, a specific stage of cancer in the sample can be detected. In one embodiment, the methylation status may be hypermethylation. In another embodiment, the methylation status may be hypomethylation.

In another embodiment, methylation of a gene or genes is decreased relative to a control sample from a subject that does not have cancer (e.g., a population average of samples, a control sample, a prior sample from the same patient, etc.). In another embodiment, methylation of a gene or genes is increased relative to a control sample from a subject that does not have cancer (e.g., a population average of samples, a control sample, a prior sample from the same patient, etc.). Accordingly, the invention in some instances provides a combination of markers for cancer, wherein some of the markers include decreased methylation of a gene or genes and other markers include increased methylation of a gene or genes.

In one embodiment of the present invention, nucleic acid may be methylated in the regulatory region of a gene. In another embodiment, a gene which is involved in cell transformation can be diagnosed at an early stage by detecting methylation outside of the regulatory region of the gene, because—in some instances—methylation proceeds inwards from the outside of the gene.

In yet another embodiment of the present invention, cells that are likely to form cancer can be diagnosed at an early stage using the methylation marker genes. When genes confirmed to be methylated in cancer cells are methylated in cells that appear normal clinically or morphologically, this indicates that the normally appearing cells are more likely to progress to cancer. Thus, cancer can be diagnosed at an early stage by detecting the methylation of cancer-specific genes in cells that appear normal.

The use of the methylation marker gene of the present invention allows for detection of a cellular proliferative disorder (dysplasia) of cells or tissues in a sample. The detection method comprises bringing a sample comprising at least one nucleic acid isolated from a subject into contact with at least one agent capable of determining the methylation state of the nucleic acid. The method comprises detecting the methylation of at least one region in at least one nucleic acid, wherein the methylation of the nucleic acid differs from the methylation state of the same region of a nucleic acid present in a sample in which there is no abnormal growth (dysplastic progression) of cells.

In yet another embodiment of the present invention, the likelihood of progression of tissue to cancer can be assessed by examining the methylation status (e.g., level, frequency, location, etc.) of a gene or genes which is specifically contains N6-mA in cancer, and determining the methylation status of tissue that is likely to progress to cancer.

In some embodiments, the cancer is a cancer cell, such as but is not limited to, a primary cancer cell, a cancer stem cell, or a metastatic cancer cell. Non-limiting examples of cancer cells include acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, wilms tumor.

Diagnostic

In one embodiment, the present invention provides a method to detect and identify already known and newly discovered diagnostically, prognostically and therapeutically relevant cancers, as well as methods that can predict which treatments and therapies are more likely to be effective. The basis of these methods resides in the measurement of N6-mA methylation status (e.g., level, frequency, location, etc.). The methods and compositions of the invention thus provide tools useful in choosing a therapy for cancer patients, methods of determining the efficacy of a therapy in a cancer patient, and methods of determining the prognosis for a cancer patient.

One aspect of the present invention relates to a method of diagnosing a condition associated with an aberrant N6-mA methylation of DNA in a sample from a subject by measuring the N6-mA methylation status (e.g., level, frequency, location, etc.) in a test sample in comparison to that of a normal or standard sample, wherein the difference between the methylation status (e.g., level, frequency, location, etc.) of the test sample as compared with that of the normal/standard sample indicates the likelihood of cancer in the test sample.

In some embodiments, the cancer is a cancer cell, such as but is not limited to, a primary cancer cell, a cancer stem cell, or a metastatic cancer cell. Non-limiting examples of cancer cells include acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, wilms tumor.

Aberrant methylation can be any change in the status frequency, location, of methylation. A methylation level that is increased is referred as hypermethylation and a methylation level that is decreased is referred to as hypomethylation. In some embodiments, the aberrant methylation is hypermethylation. In other embodiments, the aberrant methylation is hypomethylation.

The methylation of DNA can be detected via methods known in the art and those described elsewhere herein. In one embodiment, the level can be measured via SMRT-ChIP In another preferred embodiment, the methylation levels of a plurality DNA can be measured through DIP-Seq.

In another embodiment, the methods of present invention are directed to a method of diagnosing cancer in a test subject or a test sample through determining the N6-mA methylation level of DNA from the test subject or test sample in relative to the N6-mA methylation level of the DNA from a normal subject or sample.

Although improved diagnostic and prognostic accuracy and sensitivity may be achieved by using a combination of markers, such as N6-mA methylation and 5mC methylation, practical considerations may dictate use of one or more biomarkers and smaller combinations thereof. Any combination of markers may be used which comprises one or more of the markers described herein.

The methylation status (e.g., level, frequency, location, etc.) of the differentially methylated DNA regions can provide a variety of information about cancer. It can be used to predict the course of cancer in the individual or to predict the susceptibility to cancer or to stage the progression of the cancer in the individual. It can help to predict the likelihood of overall survival or predict the likelihood of reoccurrence of cancer. It can help to determine the effectiveness of a particular treatment or therapy administered to the individual.

Following the diagnosis of a subject according to the methods of the invention, it is possible to predict whether standard chemotherapy can be used to treat the patient or whether a more aggressive or alternative therapy is needed. By way of non-limiting example, patients with high N6-mA DNA methylation levels identified by the present invention may have poor outcomes based on standard care. Accordingly, the method comprises identifying nucleic acid altered methylation status (e.g., level, frequency, location, etc.) of one or more genes, where the methylation status indicates the possibility for poor survival using only standard chemotherapy.

The prognostic methods can be used to identify patients with aggressive cancer. Such patients can be offered additional appropriate therapeutic or preventative options, including personalized medicine based on their genome, transplants, surgical procedures, chemotherapy, radiation, biological response modifiers, or other therapies. Such patients may also receive recommendations for further diagnostic or monitoring procedures, including but not limited to increased frequency of checkups.

The biomarkers of the invention can be used among other things for the determination of a subject's susceptibility to a disease or disorder, determination as to whether a subject is presently affected by a disease or disorder, prognosis of a subject affected by a disease or disorder (e.g., identification of cancerous states, stages of cancer, or responsiveness of cancer to therapy), and use of therametrics (e.g., monitoring a subject's condition to provide information as to the effect or efficacy of therapy).

The diagnostic methods of the invention also provide for optimizing therapy, by classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

Compositions and Methods for Modulating N6-mA

The invention is based in part on the discovery that ALKBH1 is the demethylase for N6-mA. Thus, the invention provides methods and compositions for modulating level of N6-mA in a sample. In various embodiments, the sample includes a cancer cell. In some embodiments, the cancer cell, is a primary cancer cell, a cancer stem cell, or a metastatic cancer cell. Non-limiting examples of cancer cells include acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, wilms tumor.

In one embodiment, the method comprises administering a modulator of ALKBH1. In one embodiment the modulator is at least one selected from the group consisting of a chemical compound, a protein, a peptide, a peptidomemetic, an antibody, a ribozyme, a small molecule chemical compound, a nucleic acid, a vector, an antisense nucleic acid molecule. In one embodiment, the modulator is an activator that increases the level of activity of ALKBH1. In another embodiment, the modulator is an inhibitor that decreases the level or activity of ALKBH1.

Inhibitors

In one embodiment, the present invention provides methods and compositions for increasing the level or frequency of $N^6$-methyladenine. In one embodiment, the composition or method increases the level of N6-mA by inhibiting the level, activity, or both of ALKBH1, the N6-mA demethylase.

In one embodiment, the composition of the invention comprises an inhibitor of ALKBH1. In another embodiment, the method of the invention comprises administering an inhibitor of ALKBH1. An inhibitor of ALKBH1 is any compound, molecule, or agent that reduces, inhibits, or prevents the level or activity of ALKBH1. For example, an inhibitor of ALKBH1 is any compound, molecule, or agent that reduces ALKBH1 expression, level, activity, or both. In various embodiments, an inhibitor of ALKBH1 comprises a nucleic acid, a peptide, a small molecule, a siRNA, a ribozyme, an antisense nucleic acid, an antagonist, an aptamer, a peptidomimetic, or any combination thereof.

Nucleic Acid Inhibitors

In some aspects, the invention includes an isolated nucleic acid or an isolated oligonucleotide. In some instances the inhibitor is an siRNA or antisense molecule, which inhibits ALKBH1. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In one embodiment, siRNA is used to decrease the level of ALKBH1. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, PA (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of ALKBH1 using RNAi technology.

In another aspect, the invention includes a vector comprising an siRNA or antisense polynucleotide. Preferably, the siRNA or antisense polynucleotide is capable of inhibiting the expression of a target polypeptide, wherein the target polypeptide is ALKBH1. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In some embodiments, oligonucleotides useful for inhibiting the expression of ALKBH1 are about 5 to about 25 nucleotides in length, about 10 to about 30 nucleotides in length, or about 20 to about 25 nucleotides in length. In certain embodiments, oligonucleotides targeting ALKBH1mRNA are about 8 to about 18 nucleotides in length, in other embodiments about 12 to about 16 nucleotides in length, and in other embodiments about 7-8 nucleotides in length.

Oligonucleotides can comprise a sequence that is at least partially complementary to a target mRNA sequence, for example, at least about 75%, 80%, 85%, 90%, 95%, 96%, 97%, 98%, or 99% complementary to a target mRNA sequence. In some embodiments, the oligonucleotide can be substantially complementary to a target mRNA sequence, that is at least about 90%, 95%, 96%, 97%, 98%, or 99% complementary to a target polynucleotide sequence. In one embodiment, the oligonucleotide comprises a sequence that is 100% complementary to a target mRNA sequence. In some embodiments, the target is ALKBH1 mRNA.

Small Molecule Inhibitors

In various embodiments, the inhibitor is a small molecule that inhibits the level or activity of ALKBH1. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to reduce skin pigmentation.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Polypeptide Inhibitors

In other related aspects, the invention includes an isolated peptide inhibitor that inhibits ALKBH1. For example, in one embodiment, the peptide inhibitor of the invention inhibits ALKBH1 directly by binding to ALKBH1 thereby preventing or inhibiting the activity of ALKBH1.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

The invention also includes an inhibitor of ALKBH1 comprising an antibody, or antibody fragment, that specifically binds with ALKBH1.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain $F_V$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Activators

In one embodiment, the present invention provides methods and compositions for decreasing the level or frequency of N6-mA. In one embodiment, the composition or method decreases the level of N6-mA by activating the level, activity, or both of ALKBH1, the N6-mA demethylase.

In one embodiment, the composition of the invention comprises an activator of ALKBH1. In another embodiment, the method of the invention comprises administering an activator of ALKBH1. An activator of ALKBH1 is any compound, molecule, or agent that increases or activates the level or activity of ALKBH1. It will be understood by one skilled in the art, based upon the disclosure provided herein, that an increase in the level of ALKBH1 encompasses the increase in ALKBH1 expression, including transcription, translation, or both. The skilled artisan will also appreciate, once armed with the teachings of the present invention, that an increase in the level of ALKBH1 includes an increase in ALKBH1 activity (e.g., enzymatic activity, substrate binding activity, etc.). Thus, increasing the level or activity of ALKBH1 includes, but is not limited to, increasing the amount of ALKBH1 polypeptide, and increasing transcription, translation, or both, of a nucleic acid encoding ALKBH1; and it also includes increasing any activity of a ALKBH1 polypeptide as well.

For example, an inhibitor of ALKBH1 is any compound, molecule, or agent that reduces ALKBH1 expression, level, activity, or both. In various embodiments, an inhibitor of ALKBH1 comprises a nucleic acid, a peptide, a small molecule, a siRNA, a ribozyme, an antisense nucleic acid, an antagonist, an aptamer, a peptidomimetic, or any combination thereof.

The increased level or increased activity of ALKBH1 can be assessed using a wide variety of methods, including those disclosed herein, as well as methods well-known in the art or to be developed in the future. That is, the skilled artisan would appreciate, based upon the disclosure provided herein, that increasing the level or activity of ALKBH1 can be readily assessed using methods that assess the level of a nucleic acid encoding ALKBH1 (e.g., mRNA), the level of ALKBH1 polypeptide, and/or the level of ALKBH1 activity in a sample.

One of skill in the art will realize that in addition to activating ALKBH1 directly, diminishing the amount or activity of a molecule that itself diminishes the amount or activity of ALKBH1 can serve to increase the amount or activity of ALKBH1. Thus, an activator of ALKBH1 can include, but should not be construed as being limited to, a chemical compound, a protein, a peptidomemetic, an antibody, a ribozyme, and an antisense nucleic acid molecule. One of skill in the art would readily appreciate, based on the disclosure provided herein, that an ALKBH1 activator encompasses a chemical compound that increases the level, enzymatic activity, or substrate binding activity of ALKBH1. Additionally, an ALKBH1 activator encompasses a chemically modified compound, and derivatives, as is well known to one of skill in the chemical arts.

The ALKBH1 activator compositions and methods of the invention that increase the level or activity (e.g., enzymatic activity, substrate binding activity, etc.) of ALKBH1 include activating antibodies. The activating antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the activating antibody of the invention is an antibody that specifically binds to ALKBH1.

Further, one of skill in the art would, when equipped with this disclosure and the methods exemplified herein, appreciate that a ALKBH1 activator includes such activators as discovered in the future, as can be identified by well-known criteria in the art of pharmacology, such as the physiological results of activation of ALKBH1 as described in detail herein and/or as known in the art. Therefore, the present invention is not limited in any way to any particular ALKBH1 activator as exemplified or disclosed herein; rather, the invention encompasses those activators that would be understood by the routineer to be useful as are known in the art and as are discovered in the future.

Further methods of identifying and producing an ALKBH1 activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, a ALKBH1 activator can be synthesized chemically. Further, the routineer would appreciate, based upon the teachings provided herein, that a ALKBH1 activator can be obtained from a recombinant organism. Compositions and methods for chemically synthesizing ALKBH1 activators and for obtaining them from natural sources are well known in the art and are described in the art.

One of skill in the art will appreciate that an activator can be administered as a small molecule chemical, a protein, an antibody, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of ALKBH1. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of ALKBH1 can serve to increase the amount or activity of ALKBH1. Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity of ALKBH1, thereby increasing the amount or activity of ALKBH1. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of ALKBH1 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28:4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: DNA Methylation on $N^6$-Adenine in Mammalian Embryonic Stem Cells The data presented herein demonstrates a SMRT-ChIP approach (Single Molecular Real-Time sequencing of Chromatin Immunoprecipitation-enriched DNA) to interrogate DNA modifications enriched at H2A.X deposition regions in mouse ESCs. Also demonstrated herein is the discovery of N6-mA in mouse ESCs, together with its demethylase and a novel function in evolution, silencing of young full-length LINE1s, which is correlated with the silencing of nearby enhancers and genes in the mammalian genome.

The materials and methods employed in this example are now described.

Mouse ES Cell Culture

Mouse TT2 ES cells were cultured on gelatin coating plates with recombinant LIF. ESCs were grown in DMEM supplemented with 15% fetal bovine serum, 1% non-essential amino acids, 2 mM L-Glutamine, 1000 units of mLIF (EMD Millipore), 0.1 mM β-mercaptoethanol (Sigma) and antibiotics.

Generation of Alkbh1 Knockout ES Cell Lines with CRISPR-Cas9

Figures 8A, 8B, 8C:
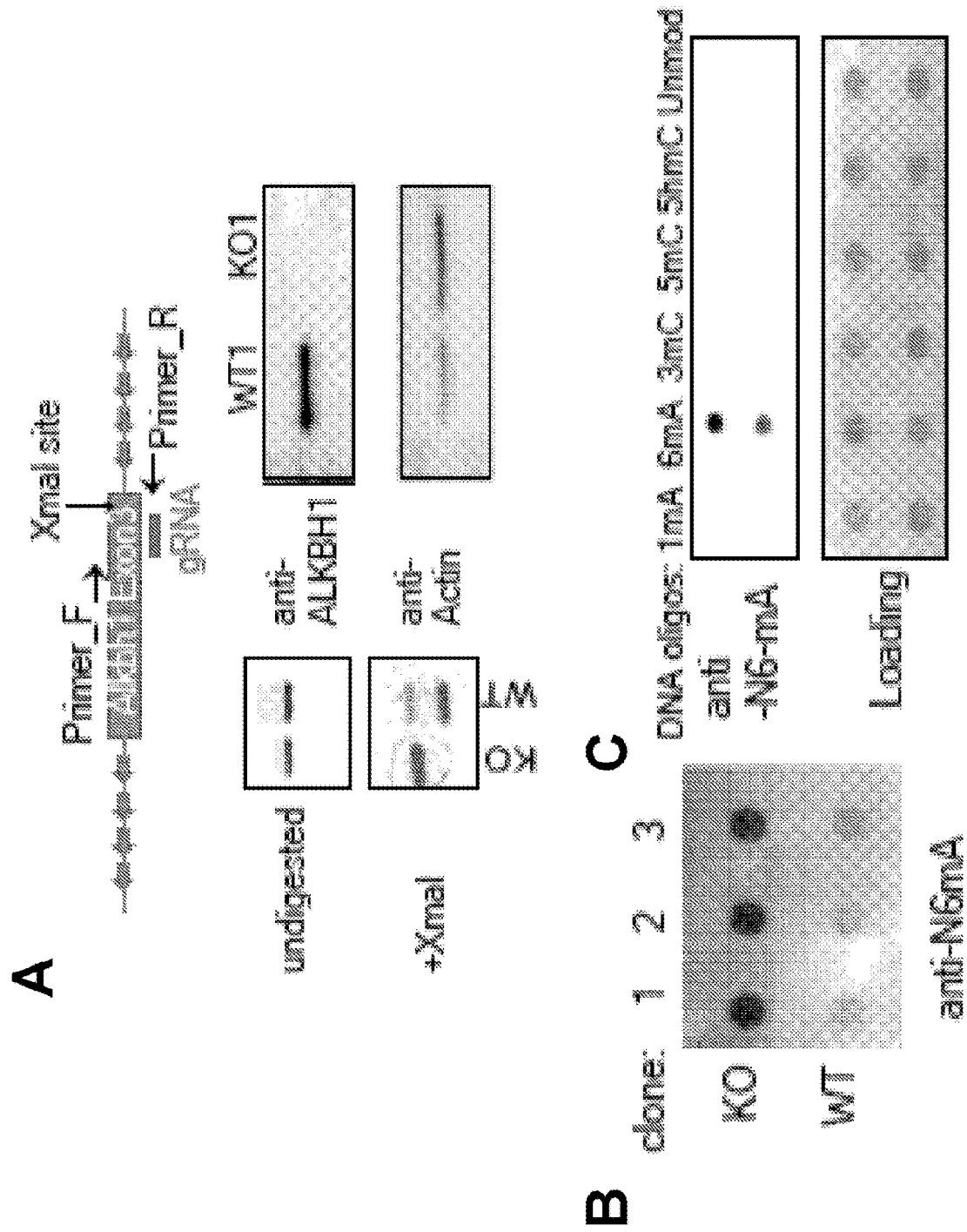
FIG. 8A through FIG. 8L, depicts results of experiments demonstrating Alkbh1 is a specific N6-mA demethylase in vivo and in vitro.

A Doxycycline (Dox)-inducible Cas9-EGFP ES cell line was established with TT2 ESC. Guide RNA oligos (5'-accgAGTGCCTCTGGCATCCCGGG-3' (SEQ ID NO:1), 5'-aaacCCCGGGATGCCAGAGGCACT-3'(SEQ ID NO:2)) were annealed and cloned into a pLKO.1 based construct (Addgene: 52628). Guide RNA virus was made in 293FT cells and infected inducible Cas9 ES cells. ES cells were first selected with Puromycin (1 µg/ml) for two days, and Dox (0.5 µg/ml) was added to induce Cas9-EGFP expression for 24 hours. ES cells were then seeded at low density to obtain single-derived colonies. Then, 72 ES cell colonies were randomly picked up and screened by PCR-enzyme digestion that is illustrated in FIG. 8A. PCR screening primers flanking guide RNA sequence are designed as following: 5'-AGGCAGATTTCTGAGTTCAAGG-3' (SEQ ID NO:3) and 5'-TTTAGTCATGTGCTTGTCCAGG-3' (SEQ ID NO:4).

PCR products were digested by XmaI overnight at 37 degree and separated on 2% agarose gel. A total 8 mutants from which PCR products show resistance to XmaI digestion were subjected to DNA sequencing. Clones that harbor deletion and coding frame shift (premature termination mutation) were expanded and used in this study.

Expression ALKBH1 Protein in 293FT Cells and Generation of ALKBH1 Mutation Proteins Human Alkbh1-Flag DNA sequence was inserted into pCW lenti-virus based vector (puromycin or Hygromycin resistance). The amino acid of D233 was mutated to A by QuickChange Site-Directed Mutagenesis (QuikChange II XL Site-Directed Mutagenesis Kit, #200521, Agilent) according to the manual. For Alkbh1 rescue experiment, wild-type and D233A mutated Alkbh1 constructs were introduced to Alkbh1 KO ES cells, pCW-Hygromycin was chosen as control. After infections, the cells were selected with Hygromycin at 200 µg/ml for 4 days, and then the cells were expanded to isolate genomic DNA for N6 mA dot blotting or other tests.

The 293FT cells were transfected with pCW-hAlkbh1 and pCW-hAlkbh1-D233A mutant plasmids along with package plasmids of pMD2.G and pSPAX2. Culture medium was changed 10 hours after transfection. The Viruses was collected and concentrated 24 and 48 hours after transfection according to manufacturer's manual (Lenti-X™ Concentrator, Clontech). To establish stable expression of hAlkbh1 and hAlkbh1-D233A cell lines, 293FT cells were infected the corresponding virus, and then select with puromycin at 1 µg/ml for 4 days. The stable cell lines of hAlkbh1-293FT and D233A-293FT were expanded to purify the proteins according to the previous reported method with some modifications (Tomomori-Sato et al., 2013, Methods Mol Biol 977:273-87). Briefly, M2 FLAG antibody was added to the nuclear extract and incubated overnight, and then Dynabeads M-280 (sheep anti-mouse IgG, from Life technology) was added to the above solution and incubated for 3-4 hours. Subsequently, the beads were separated from the solution and wash clean with washing buffer (Tomomori-Sato et al., 2013, Methods Mol Biol 977:273-87). Finally, the beads were eluted with 3×FLAG peptides, followed by standard chromatography purification to 95% purity. Proteins were analyzed by MS.

ALKBH1 Demethylase Assays

Demethylation assays were performed in 50 µL volume, which contained 50 pmol DNA oligos and 500 ng recombinant ALKBH1 (or D233A mutant) protein. The reaction mixture also consisted of 50 µM KCL, 1 mM $MgCl_2$, 50 µM HEPES (pH=7.0), 2 mM ascorbic acid, 1 mMf α-KG, and 1 mM $(NH_4)_2Fe(SO_4)_2 \cdot 6H_2O$. Reactions performed at 37 degree for 1 hour and then stopped with EDTA followed by heating 95 degree for 5 minutes. Then the reaction product was subjected to dot blotting. Substrate sequences are listed in Table 1.

Dot Blotting

First, DNA samples were denatured at 95 degree for 5 minutes, cooled down on ice, neutralized with 10% vol of 6.6 M ammonium acetate. Samples were spotted on the membrane (Amersham Hybond-N+, GE) and air dry for 5 minutes, then UV-crosslink (2× auto-crosslink, 1800 UV Stratalinker, STRATAGENE). Membranes were blocked in blocking buffer (5% milk, 1% BSA, PBST) for 2 hours at room temperature, incubated with 6 mA antibodies (202-003, Synaptic Systems, 1:1000) over night at 4 degree. After 5-times wash, membranes were incubated with HRP linked secondary anti-rabbit IgG antibody (1:5000, Cell Signaling 7074S) for 30 minutes at room temperature. Signals were detected with ECL Plus Western Blotting Reagent Pack (GE Healthcare).

Single Molecule Real-Time Sequencing (SMRT) Library Construction of Genomic DNA Samples and PCR Control DNA samples were purified by standard N-ChIP protocol. 5 µg anti-H2A.X antibodies were used per 10 million cells. DNA (250 ng) from ChIP pull-down were converted to SMRTbell™ templates using the PacBio® RS DNA Template Preparation Kit 1.0 (PacBio catalog #100-259-100) following manufacturer's instructions. Control samples were amplified by PCR (18 cycles). In brief, samples were end-repaired and ligated to blunt adaptors. Exonuclease incubation was carried out in order to remove all unligated adapters. Samples were extracted twice (0.6×AMPure beads) and the final "SMRTbells" were eluted in 10 µl EB. Final quantification was carried out on an Agilent 2100 Bioanalyzer with 1 µl of library. The amount of primer and polymerase required for the binding reaction was determined using the SMRTbell concentration (ng/µl) and insert size previously determined using the manufacturer-provided calculator. Primers were annealed and polymerase was bound using the DNA/Polymerase Binding Kit P4 (PacBio catalog #100-236-500) and sequenced using DNA Sequencing reagent 2.0 (PacBio catalog #100-216-400). Sequencing was performed on PacBio RS II sequencer using SMRT Cell 8Pac V3 (PacBio catalog #100-171-800). In all sequencing runs, a 240 min movie was captured for each SMRT Cell loaded with a single binding complex.

Detection of Modified Nucleotides with SMRT Sequencing Data

Base modification was detected using SMRT Analysis 2.3.0 (Pacific Biosciences), which uses previously published methods for identifying modified bases based on inter-pulse duration ratios in the sequencing data (Flusberg et al., 2010, Nat Methods 7:461-5). All calculations used the *Mus musculus* mm10 genome as a reference. For the detection of modified bases in individual samples, the RS_Modification_Detection.1 protocol was used with the default parameters. Modifications were only called if the computed modification QV was better than 20, corresponding to p<0.01 (vs. in silico model, Welch's t-test). The in silico model consider the IPDs from the eight nucleotides 5' through the three nucleotides 3' of the site in question. Only the sites with a sequencing coverage higher than 25 fold were used for subsequent analyses. To assess the significance of the overlap between N6 mA sites by SMRT-ChIP and peaks from DIP-Seq, intersection with DIP-seq peaks was analyzed for each of the N6 mA site called by SMRT-ChIP. To assess if the overlap is higher than expected by random chance, a permutation based approach was used, in which the original mapping is randomly shuffled between "As" that meet coverage cutoff and their corresponding QV scores, and estimated the expected overlap by random chance. As preparation for PacBio RS II sequencing, these relatively short DNA fragments (200-1000 bps on average) were made topologically circular, allowing each base to be read many times by a single sequencing polymerase. Thus, the coverage requirement for modification detection was achieved both by sequencing different fragments pulled down from the same genomic regions and by sequencing the same fragment with many passes. Of note, the SMRT-ChIP approach did not identify more N6-mA sites in Alkbh1 KO cells than WT cells. Although the exact reason remain to be identified, this analysis showed that much fewer Adenines are sequenced at a comparable coverage in Alkbh1 KO cells than WT cells (FIGS. 6B and 10C), presumably due to the difficulty of using native ChIP approach to isolate H2A.X-deposition regions from Alkbh1 KO cells because of heterochromatinization.

N6 mA-DNA-IP Sequencing and Analysis

Genomic DNA from WT or KO ES cells was purified with DNeasy kit (QIAGEN, 69504). For each sample, 5 μg DNA was sonicated to 200-500 bp with Bioruptor. Then, adaptors were ligated to genomic DNA fragments following the Illumina protocol. The ligated DNA fragments were denatured at 95 degree for 5 minutes. Then, the single-stranded DNA fragments were immunoprecipitated with 6 mA antibodies (5 μg for each reaction, 202-003, Synaptic Systems) over night at 4 degree. N6-Me-dA enriched DNA fragments were purified according to the Active Motif hMeDIP protocol. IP DNA and input DNA were PCR amplified with Illumina indexing primers. The same volume WT and KO DNA samples were subjected to multiplexed library construction and sequencing with Illumina HiSeq2000. After sequencing and filter, high quality raw reads were aligned to mouse genome (UCSC, mm10) with bowtie (2.2.4, default) (Langmead et al., 2009, Genome Biol 10:R25). By default, bowtie searches for multiple alignments and only reports the best match; for repeat sequences, such as transposons, bowtie reports the best matched locus or random one from the best-matched loci. After alignment, N6-mA enriched regions were called with SICER (version 1.1, FDR<1.0E-15, input DNA as control) (Zhang et al., 2009, Bioinformatics 25:1952-8). Higher FDR cut-off could not further reduce N6-mA peak number. MACS2 was also used for peak calling, which generated similar results as SICER. Part of the data analysis was done by in-house customized scripts in R, Python or Perl. Genomic DNA samples from mouse fibroblast cells (where the endogenous N6-mA level is undetectable) were spiked with increasing amount of N6-mA-containing, or unmodified (control), oligonucleotides, and the N6-mA levels were determined by qPCR approach after DIP and library construction.

5mC-DNA-IP Sequencing

5mC-DNA-IP was performed according to the manufacture's protocol (Active Motif 5mC MeDIP kit). The 5mC data processed with MEDIPS in Bioconductor, and in-house scripts in R, Python or Perl.

ChIP-Sequencing and Data Analysis Pipeline

Native Chromatin immunoprecipitation (N-ChIP) assay was performed as previously described. 10 million of ES cells were used for each ChIP and massive parallel sequencing (ChIP-Seq) experiment. Cell fractionation and chromatin pellet isolation were performed as described. Chromatin pellets were briefly digested with Micrococcal nuclease (New England BioLabs) and the mononucleosomes were monitored by electrophoresis. Co-purified DNA molecules were isolated and quantified (100-200 ng for sequencing). Co-purified DNA and whole cell extraction (WCE) input genomic DNA were subject to library construction, cluster generation and next-generation sequencing (Illumina HiSeq 2000).

The output sequencing reads were filtered and pre-analyzed with Illumina standard workflow. After filtration, the qualified tags (in fastq format) were aligned to the mouse genome (UCSC, mm10) with bowtie (2.2.4, default) (Langmead et al., 2009, Genome Biol 10:R25). Then, these aligned reads were used for peak calling with the SICER algorithm (input control was used as control in peak calling).

Bioinformatics Analysis of Epigenetics ChIP Sequencing Data

H3K4Me1 and H3K27Ac ChIP-Seq data were aligned to mouse genome (mm10) and peaks were called with SICER. H3K4Me1 and H3K27Ac enriched regions were defined as enhancers. Then, RSEG (Song and Smith, 2011, Bioinformatics 27:870-1) (mode 3) was to call the H3K27Ac differentiated regions. Decommissioned enhancers in KO cells are determined by H3K27Ac downregulation (compared to WT cells).

Detection of H3K4Me3 in KO Cells with ChIP-qPCR

Native ChIP-qPCR assay was used to validate H4K4Me3 at levels on gene promoters (FIG. 13). All procedures were similar to what has been described in ChIP-Seq experiments, except that the co-purified DNA molecules were diluted and subject to qPCR. (Histone H3K4Me3 antibodies: Abeam Ab8580). Real-time PCR was performed with SybrGreen Reagent (Qiagen, QuantiTect SYBR Green PCR Kit, Cat: 204143) and quantified by a CFX96 system (BioRAD, Inc).

RNA-Seq and Confirmation by RT-qPCR Approaches

Figure 9A:
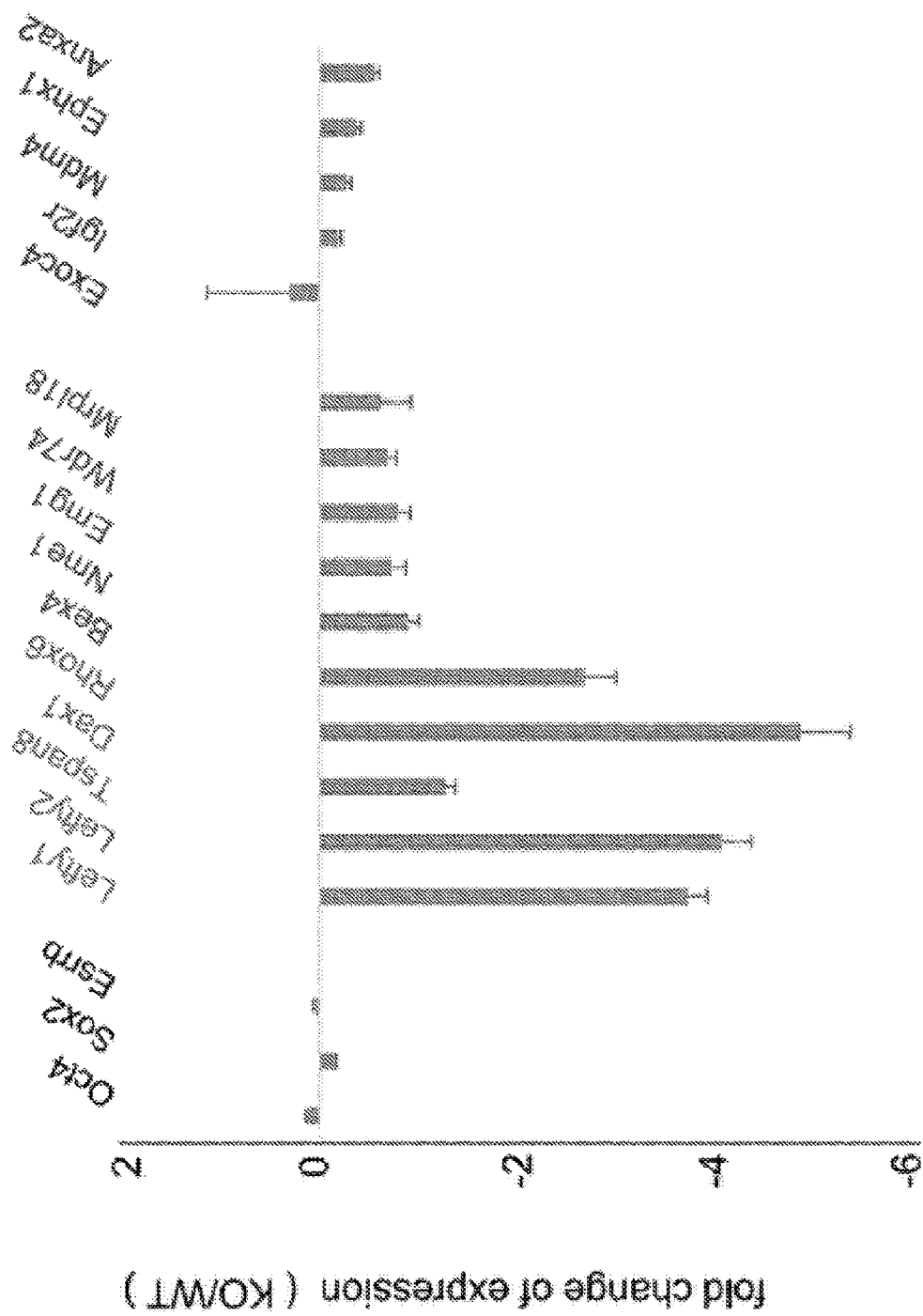
FIG. 9A through FIG. 9D, depicts RNA-Seq analysis in Alkbh1 KO ESCs.
Figures 9B, 9C:
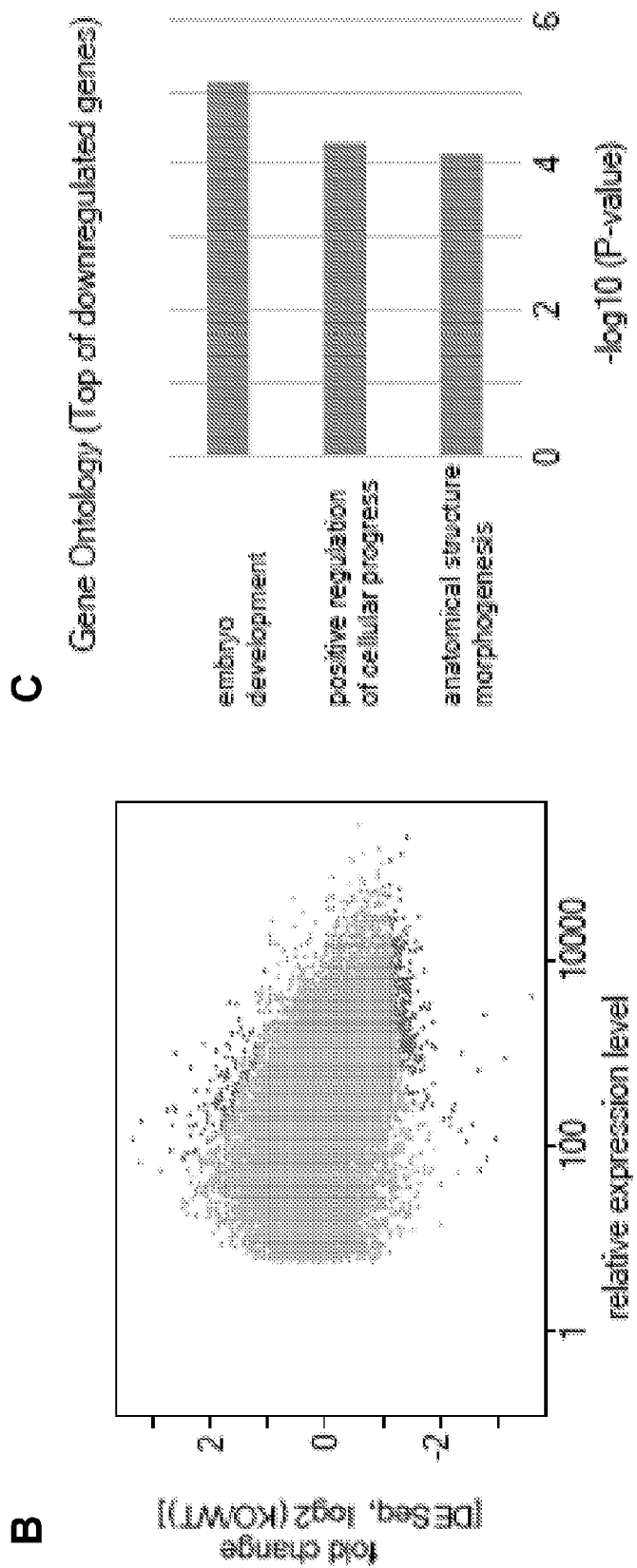

RNA was extracted with miRNeasy kit (QIAGEN, 217004) and standard RNA protocol. The quality of RNA samples was measured using the Agilent Bioanalyzer. Then, RNA was prepared for sequencing using standard Illumina "TruSeq" single-end stranded or "Pair-End" mRNA-Seq library preparation protocols. 50 bp of single-end and 100 bp of pair-end sequencing were performed on an Illumina HiSeq 2000 instrument at Yale Stem Cell Center Genomics Core. RNA-Seq reads were aligned to mm9 with splicing sites library with Tophat (Trapnell et al., 2009, Bioinformatics 25:1105-11; 2.0.4, default parameters). The gene model and FPKM were obtained from Cufflink2. The differentially expressed genes were identified by Cuffdiff (Trapnell et al., 2012, Nat Protoc 7:562-78; 2.0.0, default parameters). To make sure the normalization is appropriate, the data were also analyzed with DESeq2 (default parameters), which generated similar results (FIG. 9B). For transposons analysis, unique best alignment reads were used (alignment with bowtie (0.12.9), -m 1; or BWA) and calculated RPKM for each subfamily. For qPCR, the cDNA libraries were generated with First-strand synthesis kit (Invitrogen). Real-time PCR was performed with SybrGreen Reagent (Qiagen, QuantiTect SYBR Green PCR Kit, Cat: 204143) and quantified by a CFX96 system (BioRAD, Inc). For FIG. 3D, the specific loci L1Md elements primers were designed and optimized based on published reference (Chow et al., 2010, Cell 141:956-69).

EB Differentiation

For EB differentiation experiment, feeder free cultured ES cells were treated with 0.5% trypsin-EDTA free solution and resuspended with culture medium and counted. Then, cells were seeded at 200000 cell/ml to Petri dish with EB differentiation medium (ESC medium without LIF and beta-ME). Medium was changed every 2 days.

Histone Mass Spectrometry

Histones were isolated in biological triplicate from wild-type and Alkbh1 KO cells by acid-extraction and resolved/visualized by SDS-PAGE/Coomassie-staining. The low molecular weight region of the gel corresponding to core histones was excised and de-stained. The excised gel region containing the histones was treated with d6-acetic anhydride to convert unmodified lysine resides to heavy acetylated lysines (45 Da mass addition) as reported in Tackett et al., 2005. Following d6-acetic anhydride treatment, the gel region was subjected to in-gel trypsin digestion. Histone peptides were analyzed with a Thermo Velos Orbitrap mass spectrometer coupled to a Waters nanoACQUITY LC system as detailed in Byrum et al., 2013. Tandem mass spectrometric data was searched with Mascot for the following possible modifications: heavy lysine acetylation, lysine acetylation, lysine monomethylation, lysine dimethylation and lysine trimethylation. For each biological replicate, histone H2A was identified with 100% sequence coverage across K118/119 that revealed predominately no detectable lysine methylation LC-MS-MS Method for the Determination of $N^6$-Me-dA DNA was digested with DNA Degradase Plus (Zymo Research) by following manufacturer's instruction with small modification. Briefly, the digestion reaction was carried out at 37° C. for 70 min in a 25 µl final volume containing 5 units of DNA Degradase Plus and 5 fMol of Internal Standard. Following digestion, reaction mixture was diluted to 110 µl and the digested DNA solution was filtered with a Pall NanoSep 3 kDa filter (Port Washington, N.Y.) at 8000 rpm for 15 min. After centrifugal filtration, the digested DNA solution was injected onto an Agilent 1200 HPLC fraction collection system equipped with a diode-array detector (Agilent Technologies, Santa Clara, Calif.). Analytes were separated by reversed-phase liquid chromatography using an Atlantis $C_{18}$ T3 (150×4.6 mm, 3 µm) column. The column temperature was kept at 30° C. For the purification of N6-mA, the mobile phases were water with 0.1% acetic acid (A) and acetonitrile with 0.1% acetic acid (B). The flow rate was 1.0 ml/min with a starting condition of 2% B, which was held for 5 min, followed by a linear gradient of 4% B at 20 min, 10% B at 30 min, followed by 6 min at 80% B, then re-equilibration at the starting conditions for 20 min. dA and 6-Me-dA eluted with retention times of 14.7 and 27.0 min, respectively. The amount of dA in samples was quantitated by the UV peak area ($\lambda$=254 nm) at the corresponding retention time using a calibration curve ranging from 0.2 to 5 nMol dA on column. For the simultaneous purification of N3-Me-dC, N1-Me-dA, N3-Me-dA, N6-Me-dA and dA, the mobile phases were water with 5 mM ammonium acetate (A) and acetonitrile (B). The flow rate was 0.45 ml/min and the gradient elution program was set at following conditions: 0 min, 1% B; 2 min, 1% B; 40 min, 4% B; 60 min, 30% B; 65 min, 30% B; 65.5 min, 1% B, and 75 min, 1% B. N3-Me-dC, N1-Me-dA, N3-Me-dA, N6-Me-dA and dA eluted with retention times of 24.8, 25.0, 22.0, 60.2 and 54.2 min, respectively. The amount of dA in samples was quantitated by the UV peak area ($\lambda$=254 nm) at the corresponding retention time using a calibration curve ranging from 0.9 to 7.2 nMol dA on column. HPLC fractions containing target analyte were dried in a SpeedVac and reconstituted in 22 µl of D.I. water prior to LC-MS/MS analysis.

LC-MS-MS analysis of N3-Me-dC, N1-Me-dA, N3-Me-dA and N6-Me-dA was performed on Ultra Performance Liquid Chromatography system from Waters Corporation (Milford, Mass.) coupled to TSQ Quantum Ultra triple-stage quadrupole mass spectrometer (Thermo Scientific, San Jose, Calif.). 20 µl of sample was introduced into mass spectrometry through a 100 mm×2.1 mm HSS T3 column (Waters) at flow rate of 0.15 ml/min. Mobile phases were comprised of water with 0.1% formic acid (A) or acetonitrile (B). Elution gradient condition was set as following: 0 min, 1% B; 3 min, 1% B; 15 min, 7.5% B; 15.5 min, 1% B; 20 min, 1% B. Ionization was operated in positive mode and analytes were detected in selected reaction monitoring (SRM) mode. Specifically, 6-Me-dA and its internal standard were detected by monitoring transition ions of m/z 266.1 to m/z 150.1 and m/z 271.1 to m/z 155.1, respectively. Similarly, N3-Me-dC, N1-Me-dA and N3-Me-dA was detected by monitoring transition ions of m/z 242.1 to m/z 126.1, m/z 266.1 to m/z 150.1 and m/z 266.1 to m/z 150.1, respectively. Mass spectrometry conditions were set as following: source voltage, 3000 V; temperature of ion transfer tube, 280° C.; skimmer offset, 0; scan speed, 75 ms; scan width, 0.7 m/z; Q1 and Q3 peak width, 0.7 m/z; collision energy, 17 eV; collision gas (argon), 1.5 arbitrary units. For quantification of N6-Me-dA, the linear calibration curves ranging from 1.5 to 750 fMol, were obtained using the ratio of integrated peak area of the analytical standard over that of the internal standard. The linear calibration curves for analysis of N3-Me-dC, N1-Me-dA and N3-Me-dA were obtained using integrated peak area of the analytical standard. N3-Me-dA is not commercial available and was prepared from the reaction between 3-methyladenine and deoxythymidine in the presence of Nucleoside Deoxyribosyltransferase II. The chemical identity of purified N3-Me-dA was confirmed by using an Agilent 1200 series Diode Array Detector (DAD) HPLC system coupled with Agilent quadrupole-time-of-flight (QTOF)-MS (Agilent Technologies, Santa Clara, Calif.). Electrospray ionization (ESI)-MS-MS spectrum of N3-Me-dA was obtained by in source fragmentation. One product ion was observed from MS/MS spectra of the protonated precursor ion of $N^3$-Me-dA, resulting from the loss of the deoxyribosyl group. The accurate masses for parent and fragment ion are m/z 266.1253 and m/z 150.0774, with mass error 0.4 ppm and 3.8 ppm, respectively. The method sensitivity for N3-Me-dC, N1-Me-dA, N3-Me-dA and N6-Me-dA was detected at 1.0 fmol, 1.6 fmol, 1.0 fmol and 1.6 fmol, respectively. In order to confirm the chemical identity of the N6-Me-dA isolated from HLPC purification, HPLC fractions containing N6-Me-dA was analyzed by HPLC-QTOF-MS/MS. The chemical identity of $N^6$-Me-dA in HPLC fractions was characterized on an Agilent 1200 series Diode Array Detector (DAD) HPLC system coupled with Agilent quadrupole-time-of-flight (QTOF)-MS (Agilent Technologies, Santa Clara, Calif.). HPLC separation was carried out on a C18 reverse phase column (Waters Atlantis T3, 3 µm, 150 mm×2.1 mm) with a flow rate at 0.15 ml/min and mobile phase A (0.05% acetic acid in water) and B (acetonitrile). The gradient elution program was set at following conditions: 0 min, 1% B; 2 min, 1% B; 15 min, 30% B; 15.5 min, 1% B; and 25 min, 1% B. $N^6$-Me-dA was eluted with retention times of 12.7 min. The electrospray ion source in positive mode with the following conditions were used: gas temperature, 200° C.; drying gas flow, 12 Umin; nebulizer, 35 psi; Vcap, 4000 V; fragmentor, 175 V; skimmer, 67 V. Electrospray ionization (ESI)-MS-MS spectrum of N6-Me-dA isolated from genomic DNA was obtained by in source fragmentation. One product ion was observed from MS/MS spectra of the protonated precursor ion of N6-Me-dA, resulting from the loss of the deoxyribosyl group. The accurate masses for parent and fragment ion are m/z 266.1245 and m/z 150.0775, with mass error 3.0 ppm and 3.1 ppm, respectively. The same MS/MS fragmentation spectra was obtained from analytical standard of N6-Me-dA.

For in vitro demethylation assay, sample was treated with EDTA to remove $Fe^{2+}$. The mixture was transferred to Amicon Ultra Centrifugal Filter (EMD Millipore Corporation, 10K MWCO), followed by spin at 11000 rpm and 4° C. for 14 min. The concentrated sample was wash three times by adding 500 µl DI-H2O, followed spin at 11000 rpm and 4° C. for 14 min. The washed sample was digested with DNA Degradase Plus (Zymo Research) by following manufacturer's instruction with small modification. Briefly, the digestion reaction was carried out at 37° C. for 60 min in 60 µl final volume containing 0.17 units/µl of DNA Degradase Plus and 50 fmol of Internal Standard of N6-Me-dA. Following digestion, reaction mixture was filtered with a Pall NanoSep 3 kDa filter (Port Washington, N.Y.) at 10000 rcf and room temperature for 10 min to remove enzyme. The LC-MS/MS conditions for the quantification of dA and N6-Me-dA were set the same as those for quantification of N6-Me-dA in in vivo samples. The linear calibration curves for quantification of dA and N6-Me-dA was obtained using the ratio of integrated peak area of the analytical standard over that of the internal standard of $N^6$-Me-dA.

TABLE 1

| \_ | Primers used in RT-qPCR and ChIP-PCR | |
|---|---|---|
| RT-qPCR primers | | |
| GAPDH | Forward | TCCCACTCTTCCACCTTCGATGC (SEQ ID NO: 5) |
| | Reverse | GGGTCTGGGATGGAAATTGTGAGG (SEQ ID NO: 6) |
| Oct4 | Forward | GCAGGAGCACGAGTGGAAAGCAAC (SEQ ID NO: 7) |
| | Reverse | CAAGGCCTCGAAGCGACAGATG (SEQ ID NO: 8) |
| Nanog | Forward | AGGCTTTGGAGACAGTGAGGTGC (SEQ ID NO: 9) |
| | Reverse | TACCCTCAAACTCCTGGTCCTTC (SEQ ID NO: 10) |
| Dax2 | Forward | CGTGCTCTTTAACCCAGACCT (SEQ ID NO: 11) |
| | Reverse | TCCATGCTGACTGCACCAAT (SEQ ID NO: 12) |
| Rho6 | Forward | CTGGCTCAACTGCGGTACAG (SEQ ID NO: 13) |
| | Reverse | ACCAATTCTGCACATCACATTCA (SEQ ID NO: 14) |
| Bex4 | Forward | GGGGGAAATGTCCGAAGGAAA (SEQ ID NO: 15) |
| | Reverse | CCTGCACTACAAATCTCCCAAC (SEQ ID NO: 16) |
| Lefty1 | Forward | CTGGTTAGCCTCAGGGAAGC (SEQ ID NO: 17) |
| | Reverse | GCCACCTCTCGAAGGTTCTG (SEQ ID NO: 18) |
| Lefty2 | Forward | CGATGACCGAGGAACAGGTC (SEQ ID NO: 19) |
| | Reverse | GCCTGCCACCTCTCGAAAAT (SEQ ID NO: 20) |
| Gm8817 | Forward | AAGGCGGACAGGAACATCAG (SEQ ID NO: 21) |
| | Reverse | CAGCATGAATACAGTGGAGTCTC (SEQ ID NO: 22) |
| L1_chrX | Forward | GGACACAATGAAAGCATTTCTAAGAG (SEQ ID NO: 23) |
| | Reverse | GGGTGTTAGCAGAGAAGAACG (SEQ ID NO: 24) |
| L1_chr17 | Forward | GTTCTGTGACTCCTGAAAATGCA (SEQ ID NO: 25) |
| | Reverse | GAGTGCCTGAAACTGGGCTTA (SEQ ID NO: 26) |
| L1_ORF1 | Forward | CACTCCCACCCCACCTAGT (SEQ ID NO: 27) |
| | Reverse | TAACTCTTTAGCAGTGCTCTCCTGT (SEQ ID NO: 28) |
| L1_5UTR | Forward | AGCTTCTGGAACAGGCAGAA (SEQ ID NO: 29) |
| | Reverse | CACTGTGTTGCTTTGGCAGT (SEQ ID NO: 30) |
| SINE_B1 | Forward | GGTGTGGTGGCGCACACC (SEQ ID NO: 31) |

TABLE 1-continued

| \_ | Primers used in RT-qPCR and ChIP-PCR | |
|---|---|---|
| | Reverse | CCTGGCTGTCCTGGAGCTC (SEQ ID NO: 32) |
| SINE_B2 | Forward | CTGCCTTCAGACACACCAGAAG (SEQ ID NO: 33) |
| | Reverse | GATGGAAGAGGTTTTGCCAAG (SEQ ID NO: 34) |
| Cdx2 | Forward | GTCCCTAGGAAGCCAAGTGAA (SEQ ID NO: 35) |
| | Reverse | TTGGCTCTGCGGTTCTGAAA (SEQ ID NO: 36) |
| FoxA2 | Forward | TTTAAACCGCCATGCACTCG (SEQ ID NO: 37) |
| | Reverse | CACGGAAGAGTAGCCCTCGG (SEQ ID NO: 38) |
| Gata4 | Forward | ACACCCCAATCTCGATATGTTTGA (SEQ ID NO: 39) |
| | Reverse | ATTGCACAGGTAGTGTCCCG (SEQ ID NO: 40) |
| Gata6 | Forward | CTCAGGGGTAGGGGCATCA (SEQ ID NO: 41) |
| | Reverse | CCTCCTTGCCTCTTGGTAGC (SEQ ID NO: 42) |
| Fgf5 | Forward | CTACCCGGATGGCAAAGTCA (SEQ ID NO: 43) |
| | Reverse | TCCGTAAATTTGGCACTTGCAT (SEQ ID NO: 44) |
| Pax6 | Forward | GCACATGCAAACACACATGA (SEQ ID NO: 45) |
| | Reverse | ACTTGGACGGGAACTGACAC (SEQ ID NO: 46) |
| T | Forward | AAGACTCCTGGAAGGTGGAGAG (SEQ ID NO: 47) |
| | Reverse | CATCCTCCTGCCGTTCTTGGT (SEQ ID NO: 48) |
| Nme1 | Forward | AGGAGCACTACACTGACCTGA (SEQ ID NO: 49) |
| | Reverse | GGTTGGTCTCTCCAAGCATCA (SEQ ID NO: 50) |
| Igf2r | Forward | TGGGCCTACAAGTGCTATCTG (SEQ ID NO: 51) |
| | Reverse | TTCTCAAAAGTGAGTCACCCAC (SEQ ID NO: 52) |
| Mdm4 | Forward | TTCGGAACAAATTAGTCAGGTGC (SEQ ID NO: 53) |
| | Reverse | AGTGCATTACCTCTTTCATGGTG (SEQ ID NO: 54) |
| Ephx1 | Forward | GGAGACCTTACCACTTGAAGATG (SEQ ID NO: 55) |
| | Reverse | GCCCGGAACCTATCTATCCTCT (SEQ ID NO: 56) |
| Wdr74 | Forward | AAGGGGTGAACCTTCAGCG (SEQ ID NO: 57) |
| | Reverse | GCCCACCAAGATTTGGGTCTC (SEQ ID NO: 58) |
| Exoc4 | Forward | CACAGCCTACAGGGGCATTG (SEQ ID NO: 59) |
| | Reverse | TTGGCAGCGATTTCAAGAGTC (SEQ ID NO: 60) |
| Tspan8 | Forward | TCTGGGTATGTGGTACACTGAT (SEQ ID NO: 61) |
| | Reverse | AGGGGTTCGTGCTAGAGTCTC (SEQ ID NO: 62) |

TABLE 1-continued

Primers used in RT-qPCR and ChIP-PCR

| | | |
|---|---|---|
| Mrpl18 | Forward | GCAGCCCTCTCAACCAGTTC (SEQ ID NO: 63) |
| | Reverse | TTCTTTCCGAGCTACCCCTAA (SEQ ID NO: 64) |
| Anxa2 | Forward | ATGTCTACTGTCCACGAAATCCT (SEQ ID NO: 65) |
| | Reverse | CGAAGTTGGTGTAGGGTTTGACT (SEQ ID NO: 66) |
| Esrrb | Forward | GGACTCGCCGCCTATGTTC (SEQ ID NO: 67) |
| | Reverse | CGTTAAGCATGTACTCGCATTTG (SEQ ID NO: 68) |
| Sox2 | Forward | CATCCACTTCTACCCCACCTT (SEQ ID NO: 69) |
| | Reverse | AGCTCCCTGTCAGGTCCTT (SEQ ID NO: 70) |

ChIP-qPCR primers

| | | |
|---|---|---|
| Oct4 | Forward | AGCAACTGGTTTGTGAGGTGTCCGGTGAC (SEQ ID NO: 71) |
| | Reverse | CTCCCCAATCCCACCCTCTAGCCTTGAC (SEQ ID NO: 72) |
| Nanog | Forward | CAGACTGGGAGGGAGGGAAA (SEQ ID NO: 73) |
| | Reverse | GAGGTGCAGCCGTGGTTAAA (SEQ ID NO: 74) |
| Dax1 | Forward | CTTGCGTGCGCATTCAGTAT (SEQ ID NO: 75) |
| | Reverse | TGCTTCGCGCTCATCAGTAG (SEQ ID NO: 76) |
| L1-Promoter | Forward | ACTGCGGTACATAGGGAAGC (SEQ ID NO: 77) |
| | Reverse | TGTGATCCACTCACCAGAGG (SEQ ID NO: 78) |
| Gata6 | Forward | gctgttgccccttcccctcc (SEQ ID NO: 79) |
| | Reverse | cctgcgggcgtgggttgag (SEQ ID NO: 80) |
| Hoxa3 | Forward | TATCCACATGACCGACAGCG (SEQ ID NO: 81) |
| | Reverse | CCCCAAATCGGGACAGACTC (SEQ ID NO: 82) |

The Results of the Experiments are Now Described.

Identification of N6-mA in Mouse Embryonic Stem Cells

Since SMRT sequencing usually requires high sequencing coverage to recognize modified DNA bases (Fang et al., 2012, Nat Biotechnol 30:1232-9; Davis et al., 2013, Curr Opin Microbiol 16:192-8), it is difficult to interrogate the large mammalian genomes (2.8 Gb of *Mus musculus*, for example) with this approach (Davis et al., 2013, Curr Opin Microbiol 16:192-8). Therefore, SMRT-ChIP approach was developed to interrogate specific genomic regions of interest (FIG. 1A). Since H2A.X deposition is strongly associated with cell fate transitions in mammals (Wu et al., 2014, Cell Stem cell 14:281-94), H2A.X deposition regions in ESCs were examined in the current study. DNA molecules residing in H2A.X-deposition regions in mouse ESCs were subject to SMRT sequencing directly without PCR amplification. In total, 90% of SMRT-ChIP reads are overlapped with H2A.X deposition regions identified by traditional ChIP-Seq in the previous work (Wu et al., 2014, Cell Stem cell 14:281-94) (FIG. 6A).

Figures 6A, 6B:
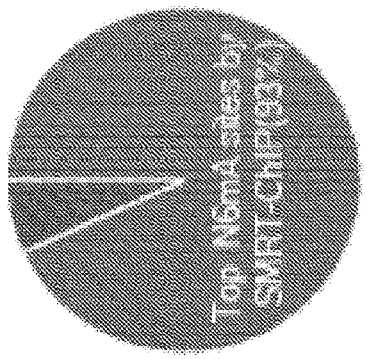
FIG. 6A through FIG. 6D, depicts results of experiments demonstrating low N6-mA levels in adult tissues and the lack of DNA alkylation adducts in ESCs.
Figures 6C, 6D:
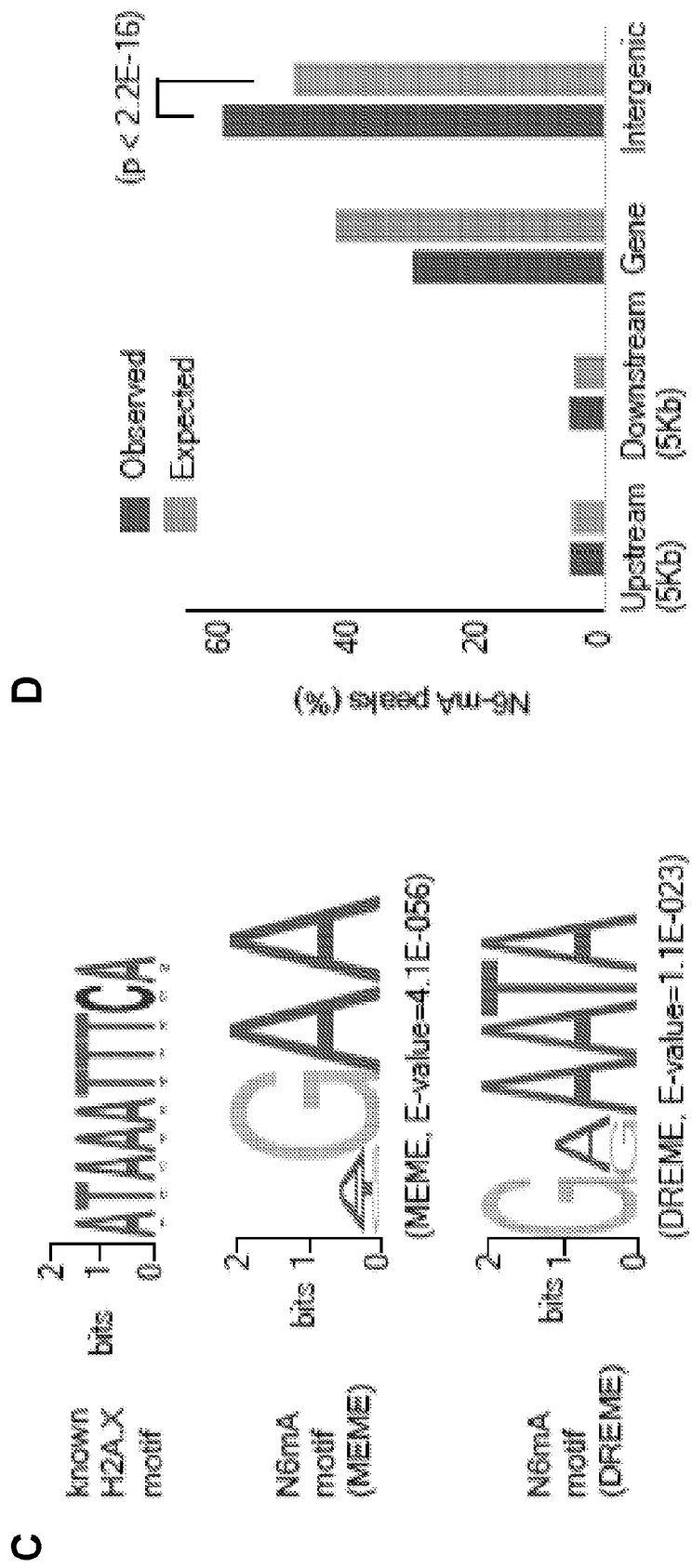

This approach identified N6-mA sites in H2A.X deposition regions with high confidence (398 sites at sequence coverage >30X, QV score ≥30 to 1108 sites at sequence coverage >25X, QV score ≥20; see FIG. 6B). A representative N6-mA site is shown in FIG. 1B. Several specific DNA motifs, which are different from H2A.X deposition motifs (FIG. 6C), were significantly associated with these putative N6-mA sites, indicating that its distribution in the genome is controlled by yet unknown factors or pathways (FIG. 6C). These N6-mA sites are enriched at intergenic, but not gene-rich regions (P<2.2E-16, FIG. 6D).

Next, the presence of N6-mA was confirmed with mass spectrometry (MS). To this end, DNA molecules from the whole genome or H2A.X-deposition regions were subject to an established and highly sensitive (LOQ: 1.6 fmol) mass spectrometry (LC-MS/MS) approach (Lu et al., 2010, Toicol Sci 115:441-51), which leverages stable isotope-labeled [$^{15}N_5$]-N6-mA as internal standard for sample enrichment and quantification (FIGS. 1C, 1D and 7A). This approach unequivocally identified N6-mA in ESCs (FIG. 1C); and estimated a frequency of 25-30 parts per million (ppm) of deoxy-adenine (dA) in the H2A.X deposition regions for the N6-mA modification (FIG. 1D), a 4-fold enrichment over the whole genomic input DNA samples (6-7 ppm). Additionally, very low levels of N6-mA were found in other differentiated mouse cells and adult tissues (FIG. 7B).

Figures 7A, 7B, 7C:
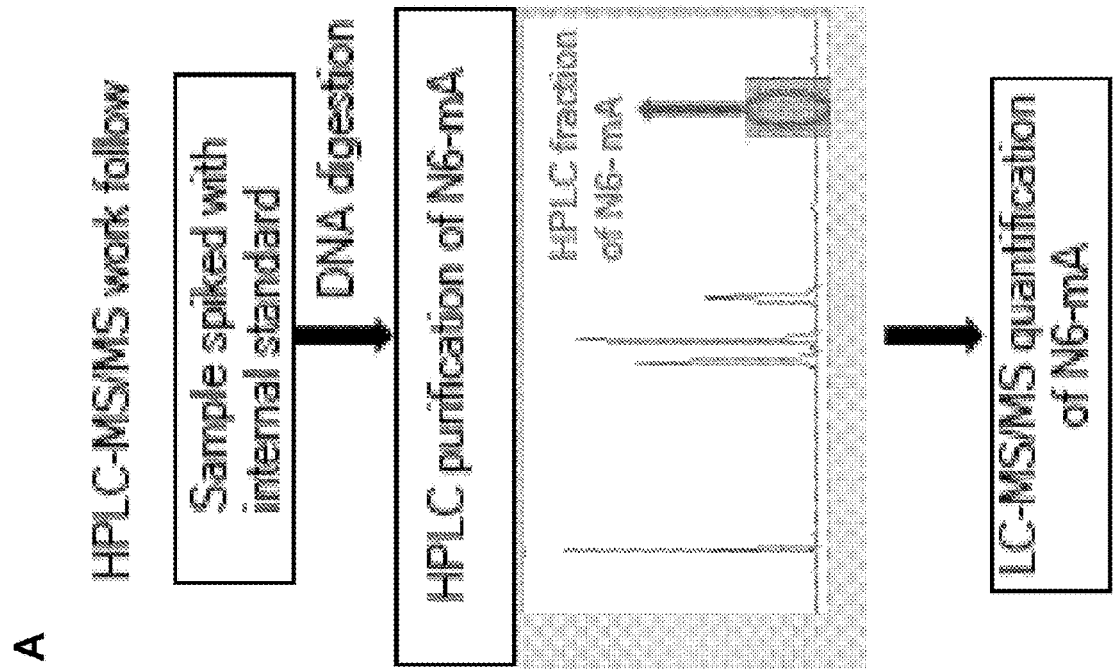
FIG. 7A through FIG. 7E, depicts results of experiments demonstrating the LC-MS/MS data of N6 mA.
Figure 7D:
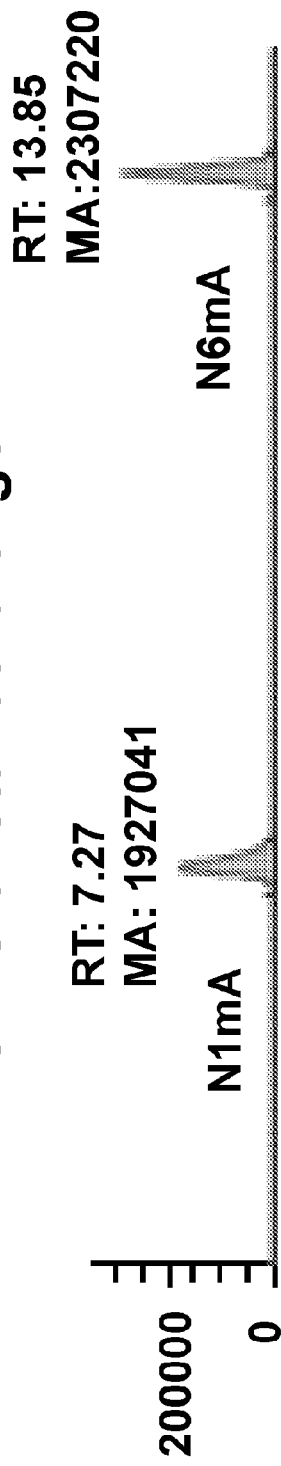
Figure 7D:
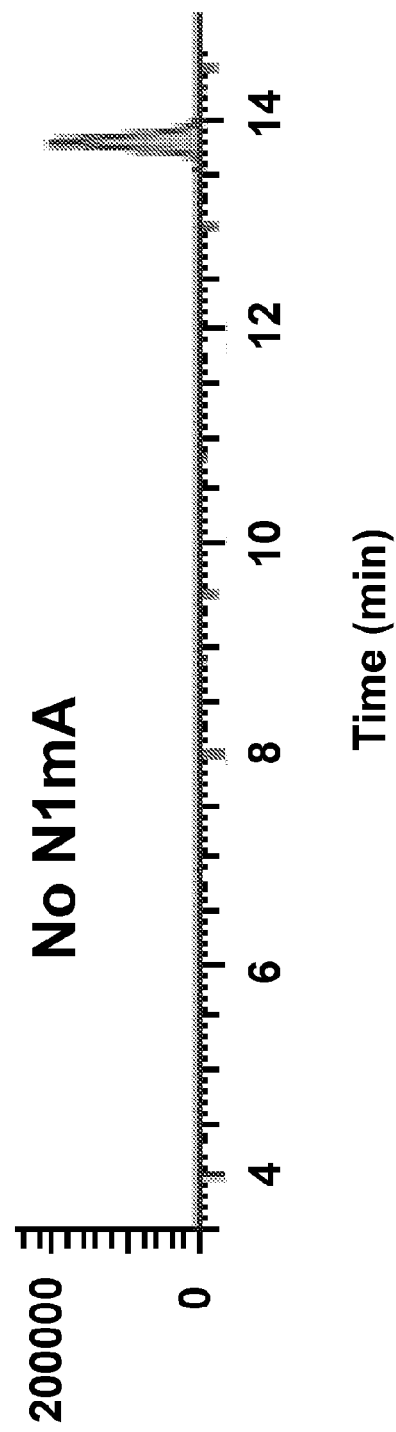
Figure 7E:
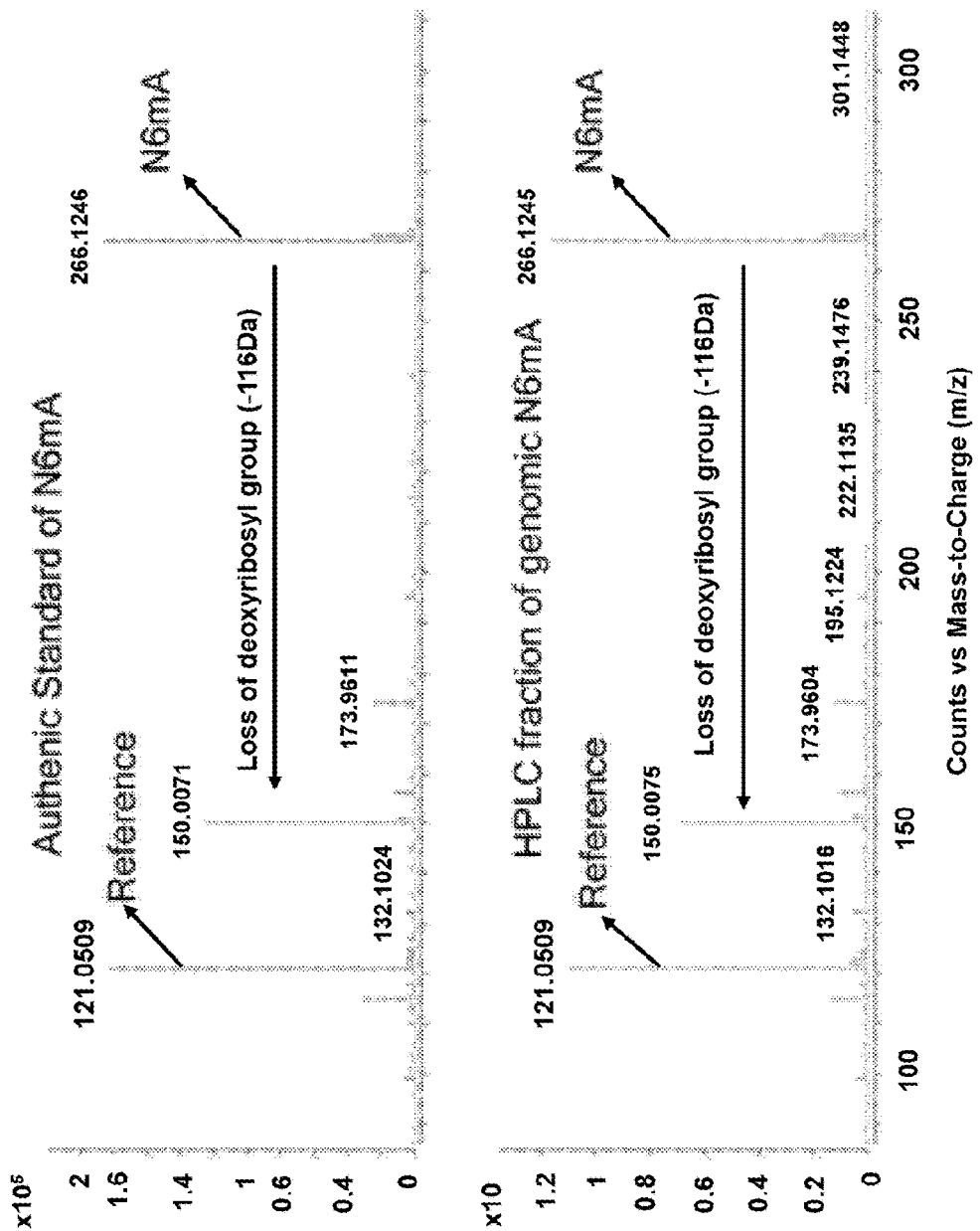

Importantly, none of the other known alkylation adducts, such as 1-methyladenine (N1-mA), 3-methyladenine (N3-mA) or 1-methylcytosine (N3-mC) (Sedgwick, 2004, Nat Rev Mol Cell Biol 5:148-57), were detected from H2A.X-deposition-region or whole genomic DNA samples (FIG. 7C). Of note, although it was reported that N1-mA shares similar kinetic profiles to N6-mA in SMRT sequencing (Flusberg et al., 2010, Nat Methods 7:461-5), this MS approach, which can distinguish N6-mA from N1-mA, ruled out this plausible explanation of the SMRT-ChIP data (FIGS. 7D and 7E).

Alkbh1 is a Major Demethylase for N6-mA in ESCs

Next the N6-mA demethylase was identified. The mammalian Alkbh family genes, which contain the conserved $Fe^{++}$ ion and 2-oxo-glutarate-dependent, dioxygenase domain, are promising candidates (Sedgwick, 2004, Nat Rev Mol Cell Biol 5:148-57; Shen et al., 2014, Annu Rev Biochem 83:585-614). Among these genes, Alkbh2 and 3 can efficiently remove 1 mA or 3mC from DNA or RNA, but not N6-mA (Shen et al., 2014, Annu Rev Biochem 83:585-614). Alkbh1 is arguably the most intriguing member in this gene family: it shares the strongest similarity to bacteria demethylase Alkb and yet only has negligible demethylation activities on 3-mC in comparison to Alkh2 and Alkbh3 (Sedgwick, 2004, Nat Rev Mol Cell Biol 5:148-57; Shen et al., 2014, Annu Rev Biochem 83:585-614). Additionally, Alkbh1 deficiency in mice results in 80% reduction of the litter size due to embryonic lethality among other phenotypes, indicating that Alkbh1 plays a critical role in early development (Müller et al., 2013, PLoS One 8:e67403; Nordstrand et al., 2010, PLoS One 5:e13827).

Figures 2A, 2B, 2C, 2D, 2E:
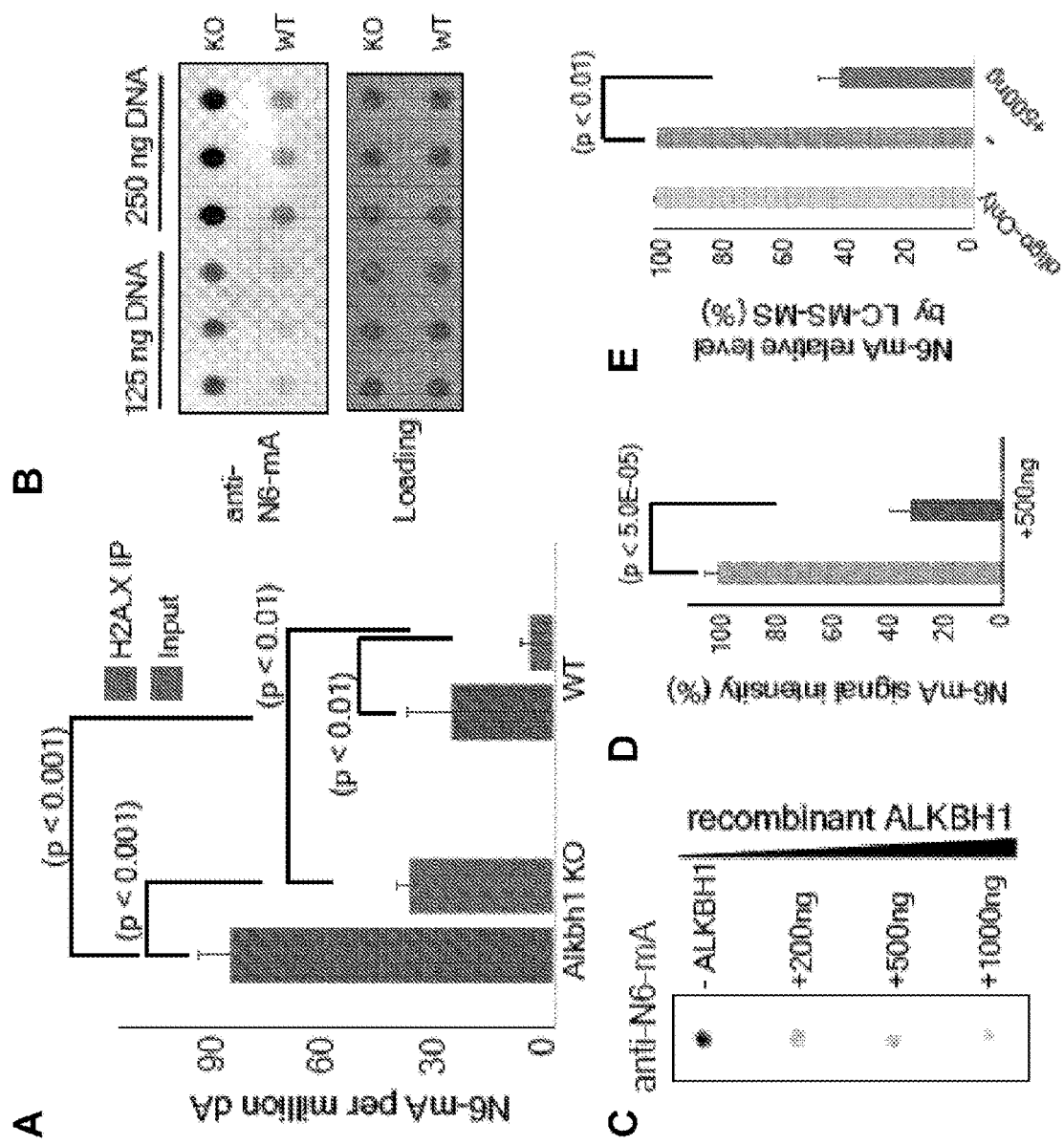
FIG. 2A through FIG. 2E, depicts results of experiments demonstrating Alkbh1 is a demethylase for N6-mA in ESCs.
Figures 8D, 8E, 8F, 8G:
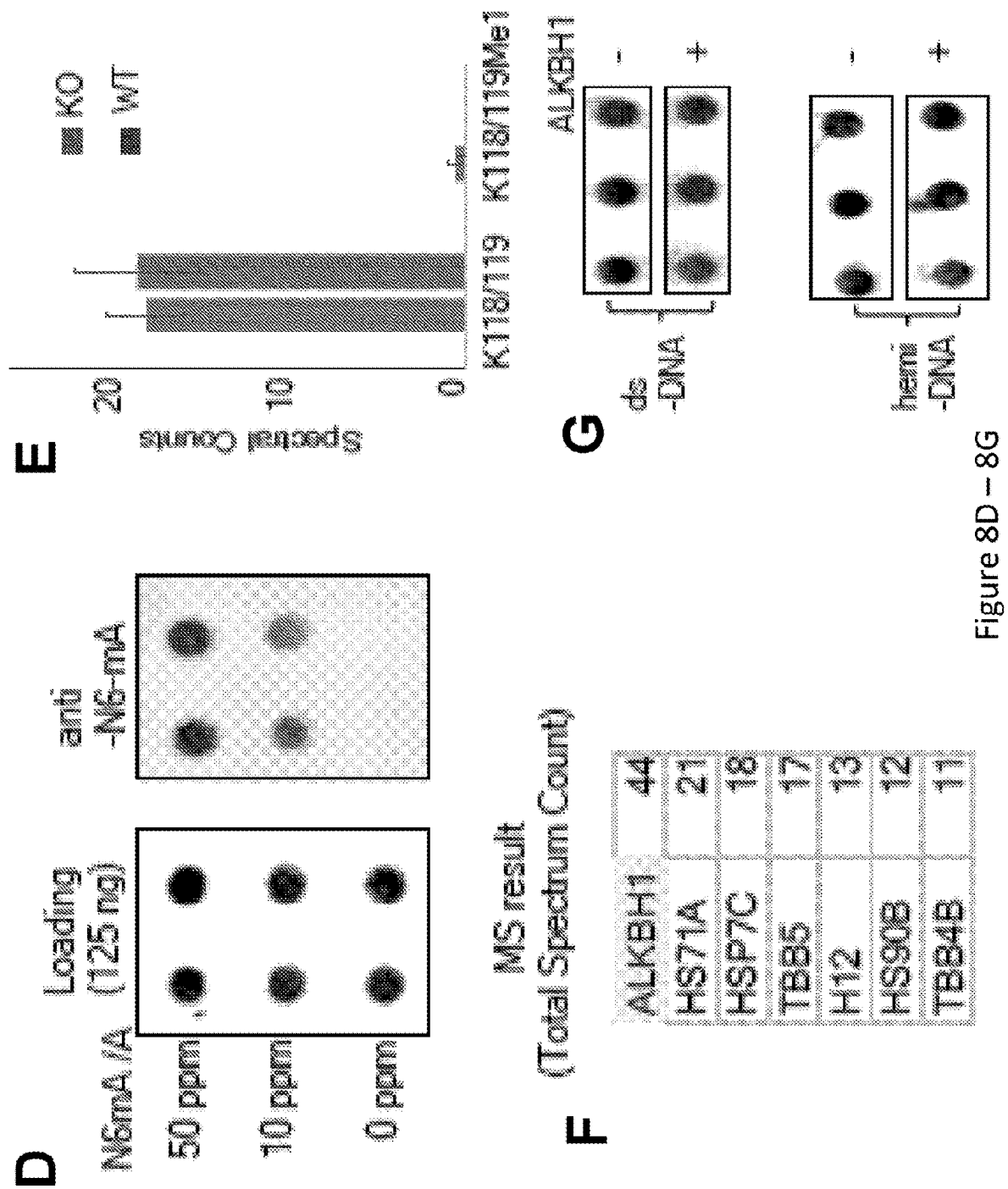

Given these considerations, Alkbh1 homozygous knock out ESC lines were generated (referred to as Alkbh1 KO ESCs hereafter) via CRISPR/Cas9 technology (FIG. 8A). MS analysis demonstrated that N6-mA levels in whole genomic input DNA or H2A.X deposition regions are both significantly increased (3-4 fold) in multiple Alkbh1 KO ESC clones (FIG. 2A). Similar elevated N6-mA levels in Alkbh1 KO ESCs are confirmed by immunoblotting experiments with specific antibodies against N6-mA (FIGS. 2B, and 8B-8D). A previous work suggested that Alkbh1 may regulate histone H2A K118 or K119 methylation in ESCs (Ougland et al., 2012, Stem cells 30:2672-82). The possibility of Alkbh1 being a histone demethylase was ruled out since H2AK118/119 is predominately non-methylated at similar levels between wild-type and Alkbh1 KO ESCs (FIG. 8E).

Figures 8H, 8I:
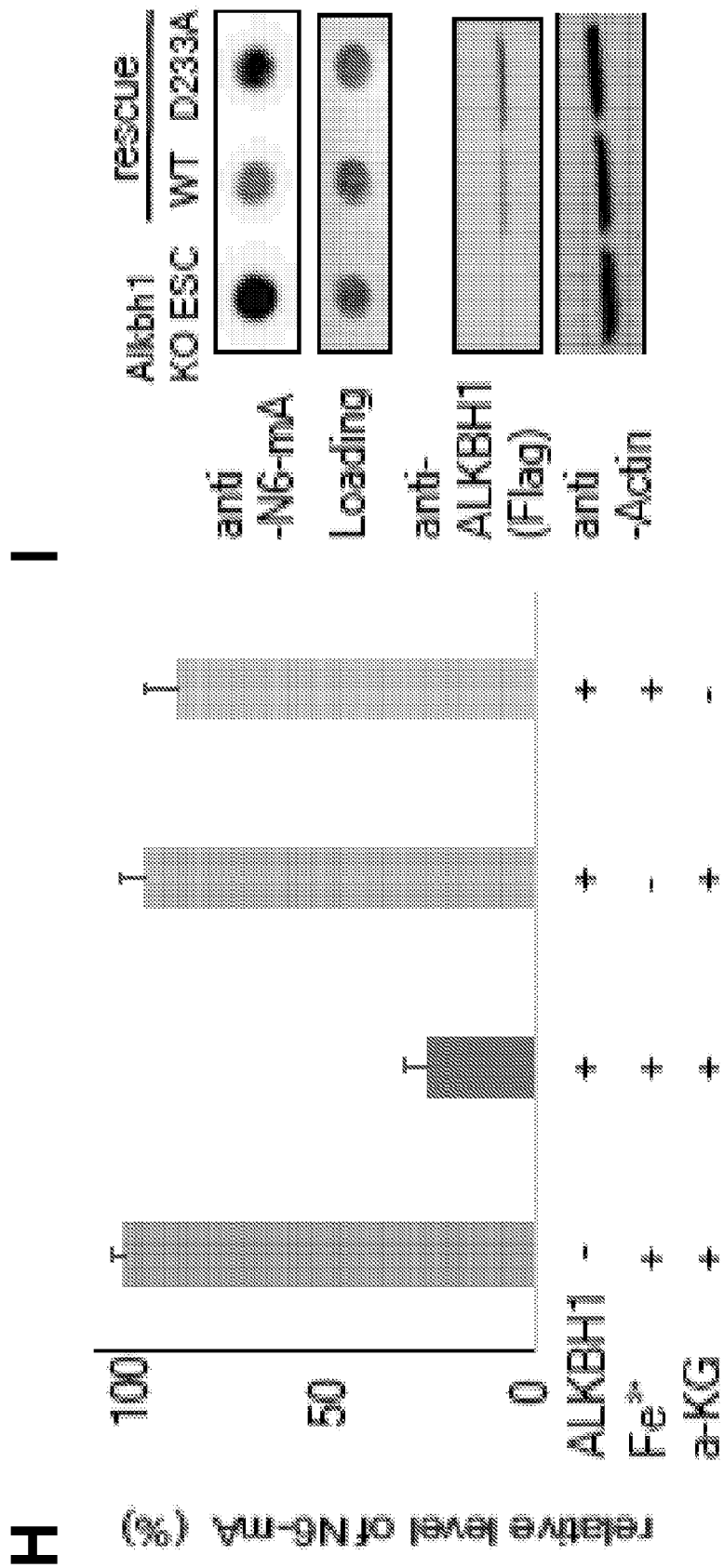

Next the catalytic activities of recombinant ALKBH1 proteins were investigated with in vitro demethylation assays. The recombinant ALKBH1 proteins were generated with >95% purity (FIG. 8F). The recombinant ALKBH1 can efficiently reduce N6-mA level from single-stranded synthetic oligonucleotide substrates (FIGS. 2C-2E), while its activities towards dual- or hemi-methylated double-stranded substrates are much reduced, suggesting the demethylation may be coupled with transcription and/or replication in vivo (FIG. 8G). Furthermore, these activities are dependent on $Fe^{++}$ ion and 2-oxo-glutarate, as expected for an active dioxygenase (FIG. 8H).

Figures 8J, 8K, 8L:
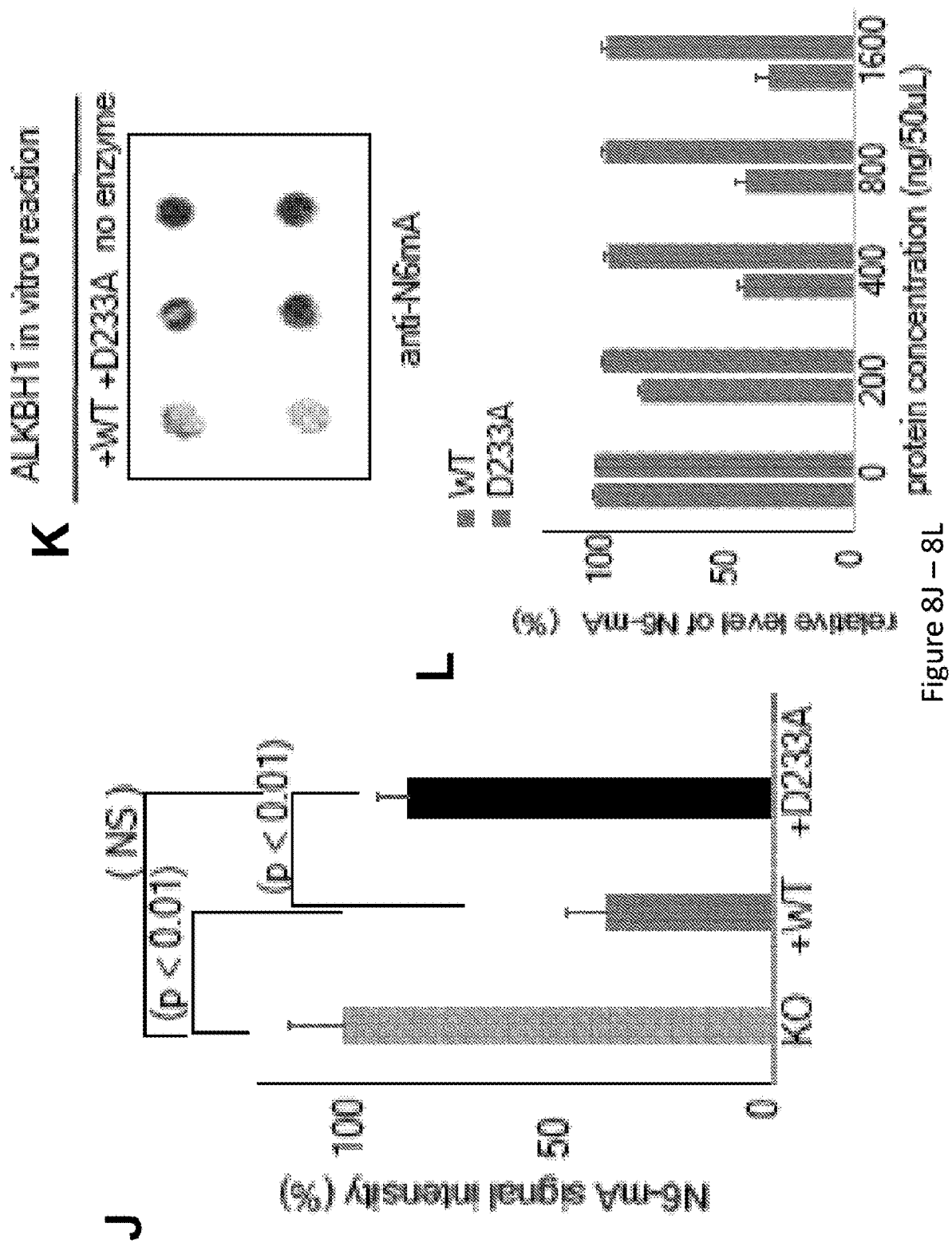

The catalytic activities of ALKBH1 were further substantiated by a point mutant at a critical residue (D233A) that may coordinate the $Fe^{++}$ ion. Corroborated by the much reduced activities of the recombinant mutant proteins (D233A) (FIGS. 8I and 8J), the increase of N6-mA in Alkbh1 KO mouse ESCs could be efficiently rescued by ectopic expression of WT but not mutant Alkbh1 (FIGS. 8K and 8L).

N6-mA Preferentially Suppresses the Expression of Genes and Young Full-Length LINE-1 on the X-Chromosome The discovery of Alkbh1 as a N6-mA demethylase enables us to interrogate the functions of N6-mA in ESCs. Since this modification may be an important component of epigenetic regulation of gene expression, a RNA-Seq approach was used to interrogate the transcriptome of Alkbh1 KO ESCs. This analysis demonstrated that 550 genes are significantly downregulated (FPKM>5, FDR<0.05, fold change >2 or <0.5, from Cuffdiff2) (FIG. 3A; (Wu et al., 2016, "DNA Methylation on N6-adenine in mammalian embryonic stem cells," Nature)), which can be verified by the RT-qPCR approach (FIG. 9A), Although a small number of low-expressing genes (70) were initially identified as upregulated by the RNA-Seq analysis, they are mostly likely false positives which cannot be verified with RT-qPCR approach (0/5, FIGS. 9A and 9B), indicating that increasing N6-mA level in ESCs leads to gene silencing in principle. Gene ontology analysis showed that the top down-regulated genes are enriched for developmental factors or lineage specifying genes (FIG. 9C). On the other hand, the expressions of pluripotency genes, such as Oct4 and Nanog, were unaltered and Alkbh1 KO ESCs maintained the undifferentiated morphology and were able to self-renew.

Figures 3A, 3B, 3C, 3D:
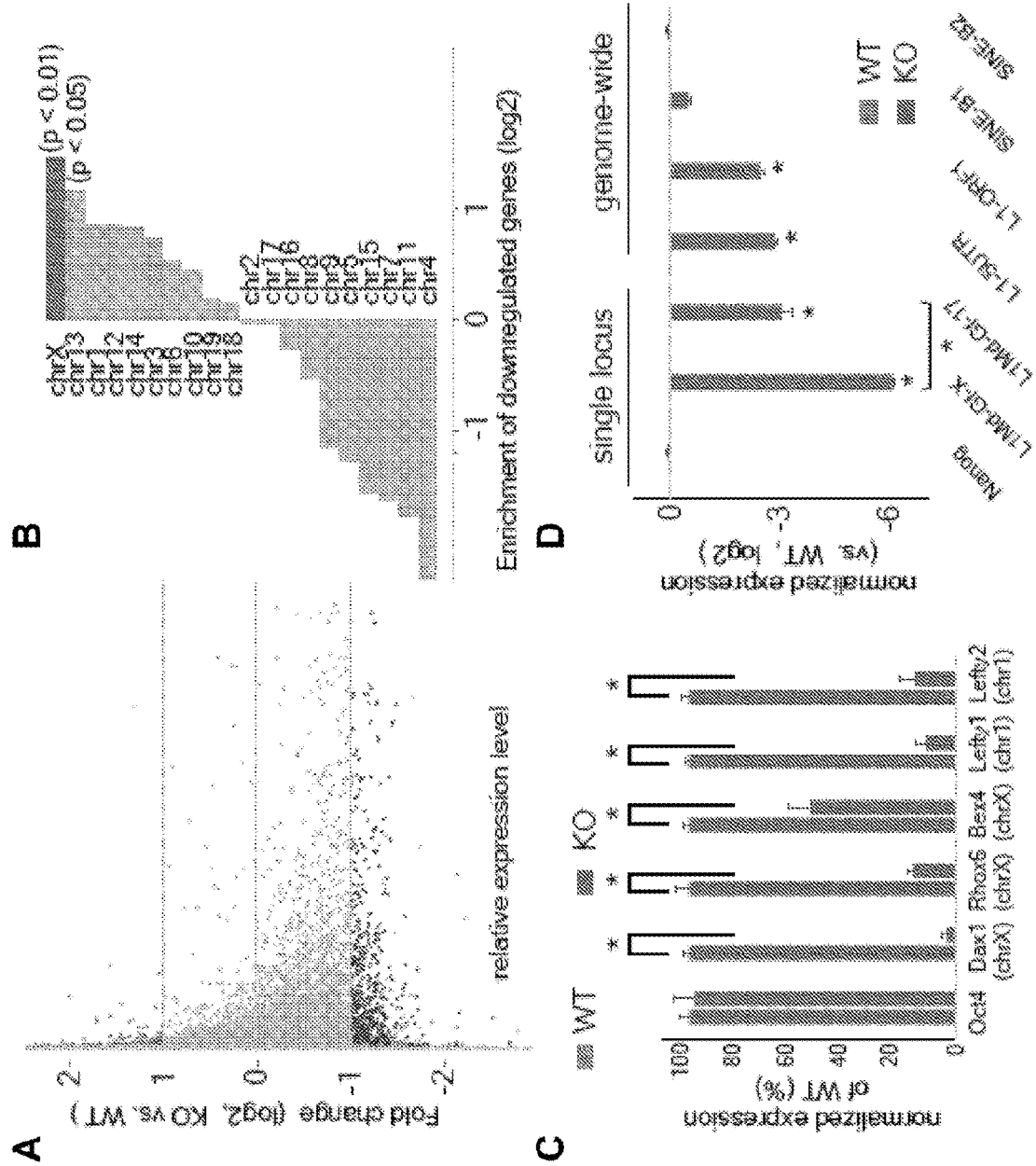
FIG. 3A through FIG. 3D, depicts results of experiments demonstrating Alkbh1 deficiency silences genes on X-chromosome and young full-length L1s.

Unexpectedly, the genomic locations of the downregulated genes have a strong chromosome bias (P<0.01, Bionomial test): they are most significantly enriched on the X-chromosome, whereas modestly enriched on Chr13 (P<0.05, Bionomial test), but not on the other chromosomes (FIG. 3B). qRT-PCR analysis confirmed the downregulation of the X-chromosome genes, together with other genes on autosomes (FIG. 3C). These results indicate that accumulation of N6-mA represses transcription on the X-chromosome.

Figure 9D:
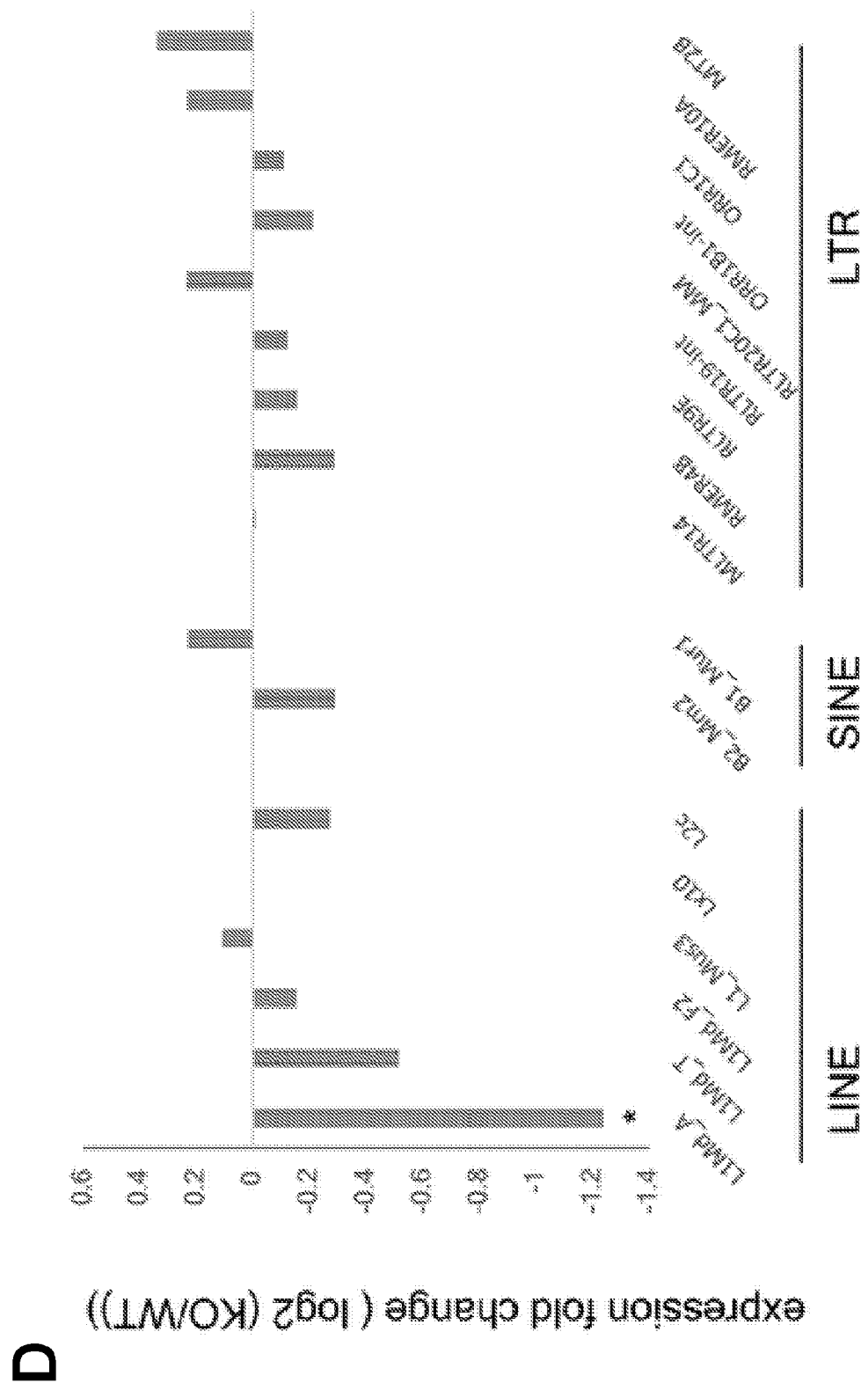

To test this hypothesis, the expression of young full-length LINE-1 transposons (L1s), which are specifically enriched on the X-chromosome, were investigated (FIG. 4; Abrusán et al., 2008, PLoS Genet 4:e1000172; Bailey et al., 2000, PNAS 97:6634-9). Of note, owing to their unique sequences, the expression of such L1s can be interrogated and distinguished from other L1 subfamilies (Chow et al., 2010, Cell 141:956-69). These results demonstrated that a young full-length L1 (belong to the L1Md-Gf subfamily (Goodier et al., 2011, Genome Res 11:1677-85; Castro-Diaz et al., 2014, Genes Dev 28:1397-409)) located on the X-chromosome is much more repressed (more than 60 fold) than its counterpart located on Chr17 (FIG. 3D). These results indicated that the L1 density may affect the silencing effects of N6-mA. Consistently, qRT-PCR approach targeting the 5'-UTR or open reading frame 1 (ORF1), which are usually retained in young full-length L1s, but not old, truncated L1s (Goodier and Kazaqzian, 2008, Cell 135:23-35), also demonstrated a significant decrease of L1 expression, while the SINE family transposons were almost unaffected (FIG. 3D). Additionally, analyses of the transposons transcripts in the RNA-Seq experiments confirmed the downregulation of the young full-length L1 subfamilies (FIG. 9D). These results raised the intriguing possibility that genes and young full-length L1s on X-chromosomes may be co-regulated by N6-mA.

N6-mA Specifically Targets Young Full-Length L1s Enriched on the X-Chromosome

The above results suggest that N6-mA adopts a new function in transcriptional silencing in mammals whereas it is implicated in gene activation in other species (Heyn and Esteller, 2015, Cell 161:710-3; Zhang et al., 2015, Cell 161:893-906; Greer et al., 2015, Cell 161:868-78; Fu et al., 2015, Cell 161:879-92). To further investigate N6-mA function, the differential methylation regions (DMR) of N6-mA in Alkbh1 KO ESCs were identified.

Figure 10A:
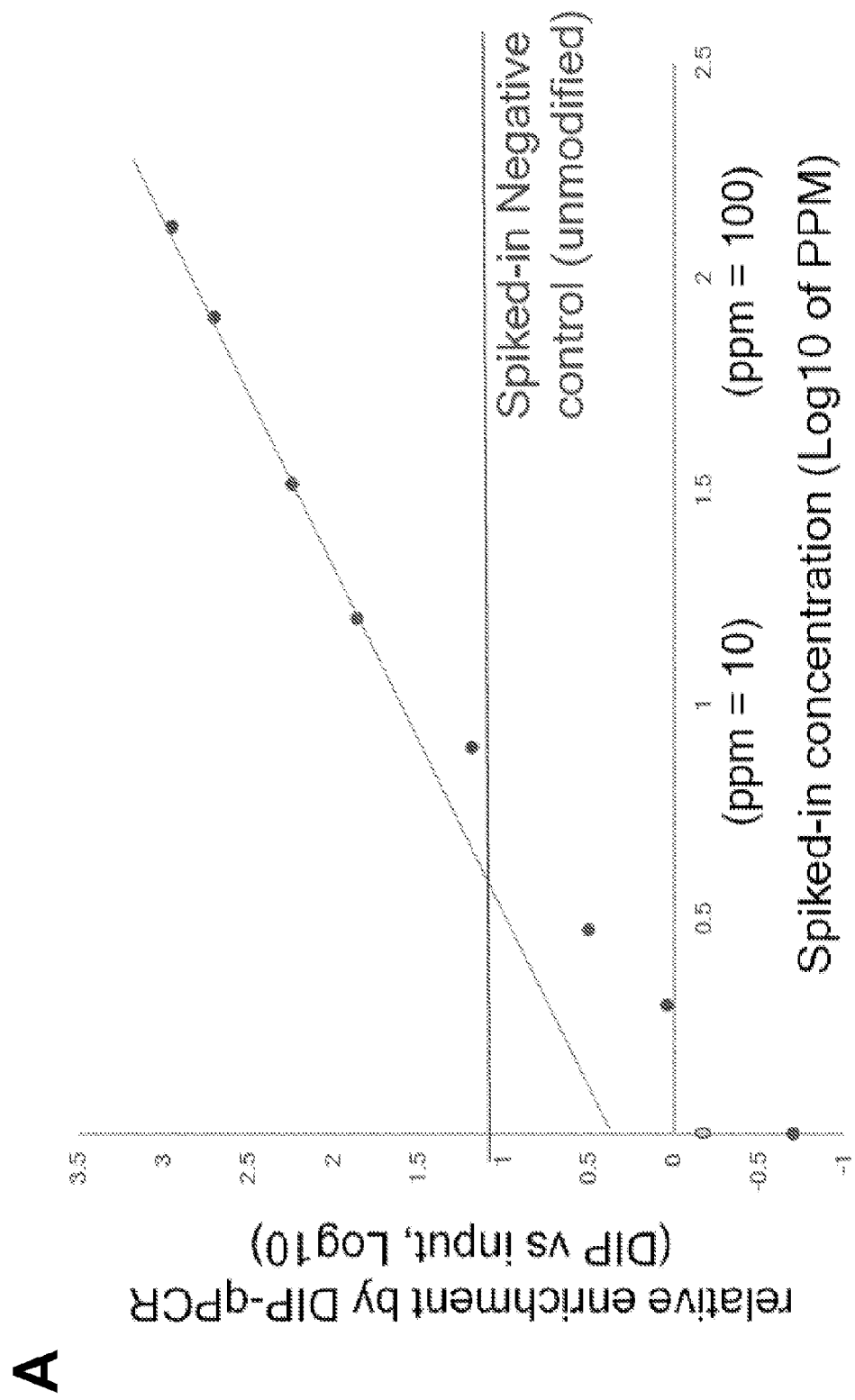

Since there is a global increase of N6-mA in Alkbh1 KO cells as indicated by MS analyses (FIG. 2) while SMRT-ChIP approach can only interrogate H2A.X deposition regions (FIG. 1A), a N6-mA DIP-Seq (N6-mA DNA IP with anti-N6-methyladenine antibodies followed by next generation sequencing) experiment was performed. First, to validate this approach, its detection limit and lineage response range by a "spike-in experiment" was determined. With this approach, it was shown that the detection limit is around 10-15 ppm N6-mA (of Adenine), while this approach can't distinguish N6-mA from unmodified Adenines at 5 ppm anymore. Importantly, N6-mA levels in Alkbh1 KO cells (30-35 ppm) is within the lineage range of this approach (20 ppm to 120 ppm) (FIG. 10A).

Figures 10B, 10C:
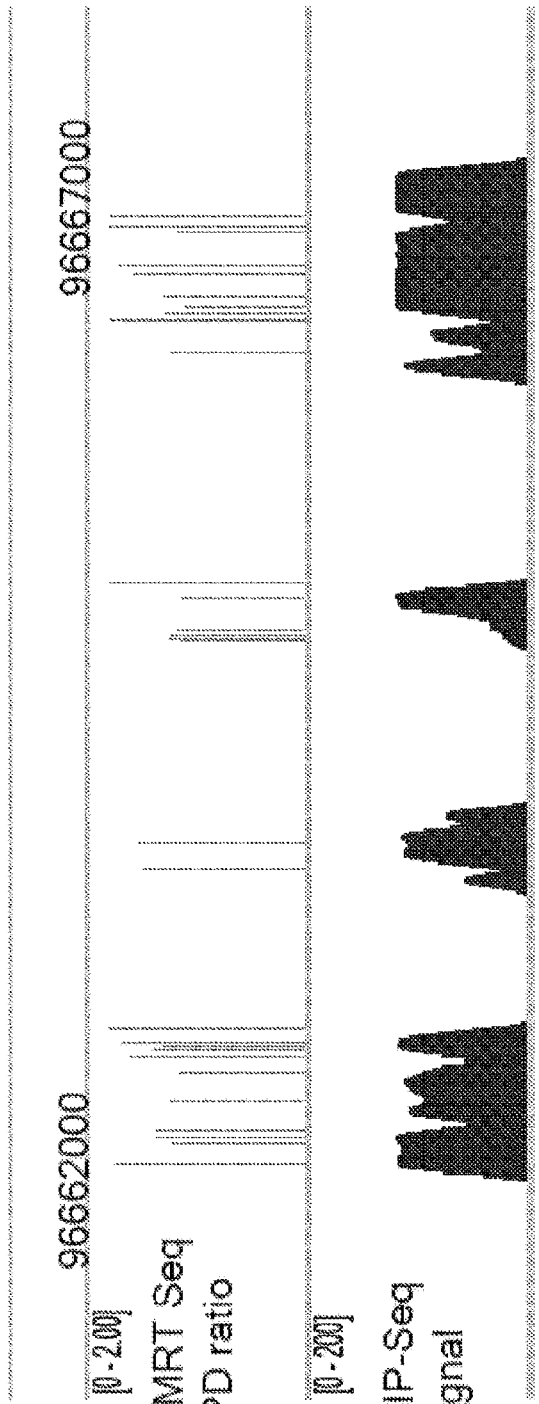
FIG. 10B depicts the track of different sequencing method showing N6-mA sites overlapped between SMRT-ChIP and DIP-Seq in Alkbh1 KO ESCs.
FIG. 10C depicts the number of SMRT-ChIP N6 mA sites in Alkbh1 KO cells at different coverage and QV cut-off. With rising coverage and QV cut-off, overlap between SMRT-ChIP N6 mA sites and DIP-Seq N6 mA sites also increases.

Consistent with the genome-wide upregulation, N6-mA DIP-Seq identified 37,581 N6-mA sites in Alkbh1 KO ESCs, in agreement with the estimate (35,000-40,000 sites) based on MS results (30-35 ppm). On the other hand, the N6-mA peaks in WT ES cells are underrepresented since N6-mA frequency is only 6-7 ppm in these cells. SMRT-ChIP approach was also used to interrogate N6-mA distribution in H2A.X-deposition regions in Alkbh1 KO EScells (FIGS. 10B and 10C). These results demonstrated that putative N6-mA sites called by SMRT-ChIP at various cutoffs (sequences coverage: 10×-30×; QV: 20-30) significantly (P<1.0E-5; observed vs. permutation) overlap with those identified by DIP-Seq. In addition, the percentage of overlap increases with rising sequencing coverage and QV scores. These results further validate the SMRT-ChIP approach.

Figures 4A, 4B, 4C:
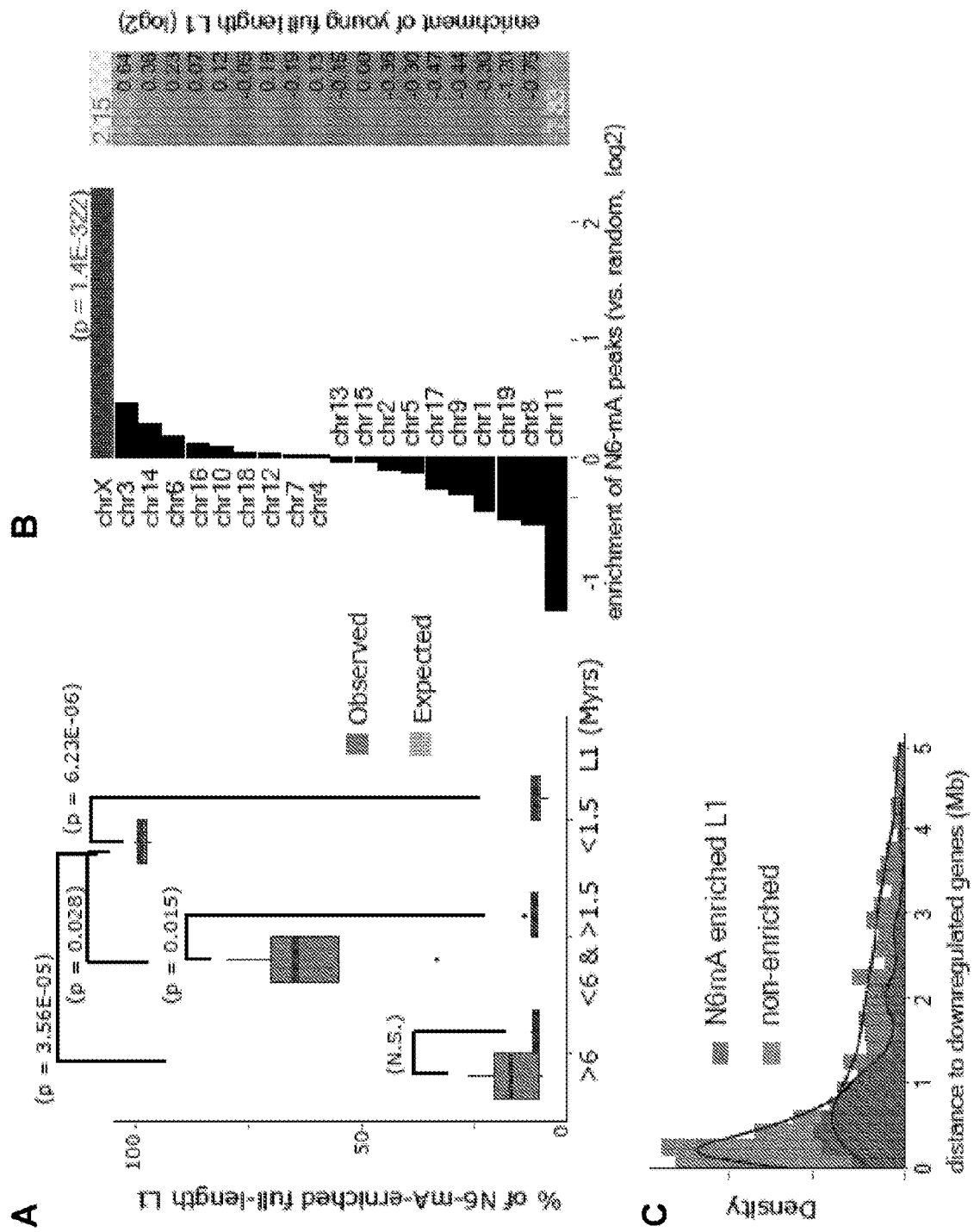
FIG. 4A through FIG. 4D, depicts results of experiments demonstrating N6-mA is enriched at young full-length L1s, which are located in the vicinity of the downregulated genes in Alkbh1 KO ESCs.
Figures 10D, 10E:
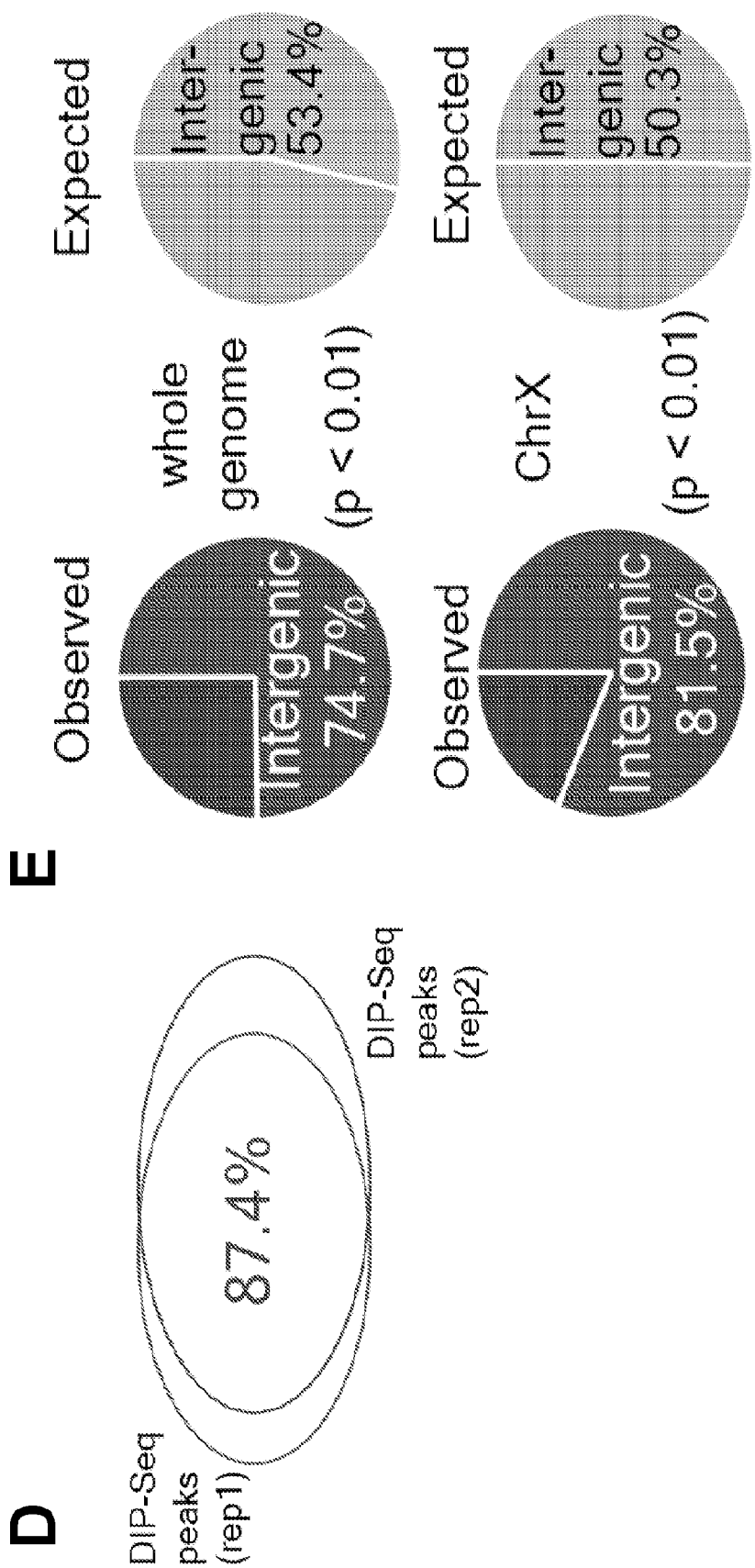
FIG. 10D depicts the biological replicates of Alkbh1 KO ESCs N6 mA-DIP peaks show 87.4% overlap.
FIG. 10E depicts a large majority of N6-mA peaks are in the intergenic regions at the whole genome level or on the X-chromosome.
Figure 10F:
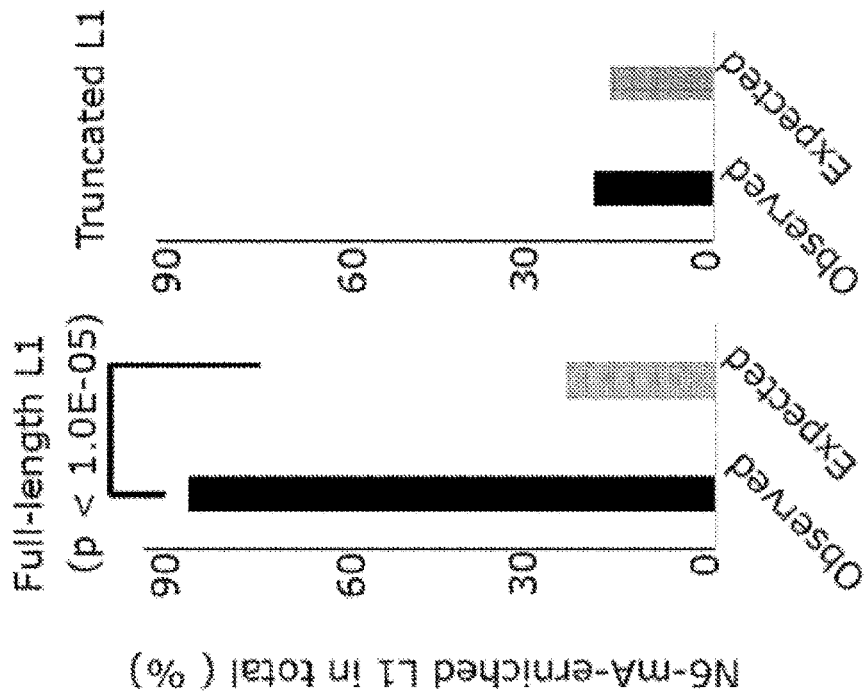
FIG. 10F depicts in Alkbh1 KO ESCs, N6-mA peaks are mainly targeted to LINE-1s on the X-chromosome or genome-wide.
Figure 10G:
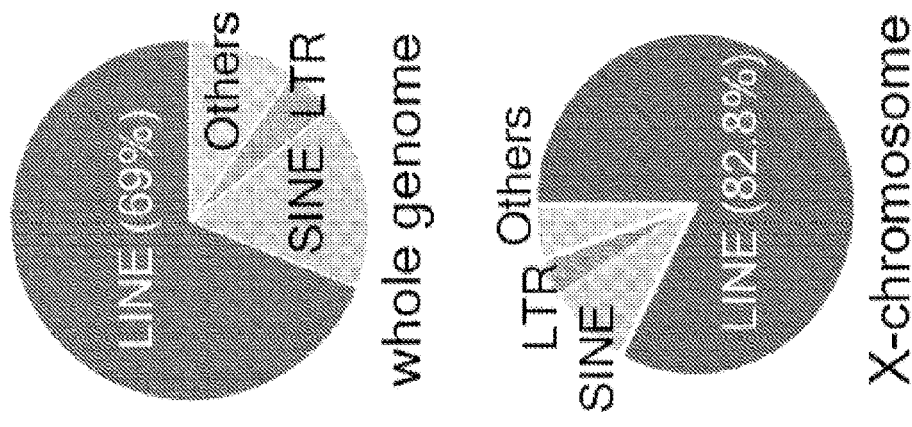
FIG. 10G depicts N6-mA peaks are significantly enriched on full-length, but not on truncated L1s (P<1.0E-05, Chi-square test).
Figure 10H:
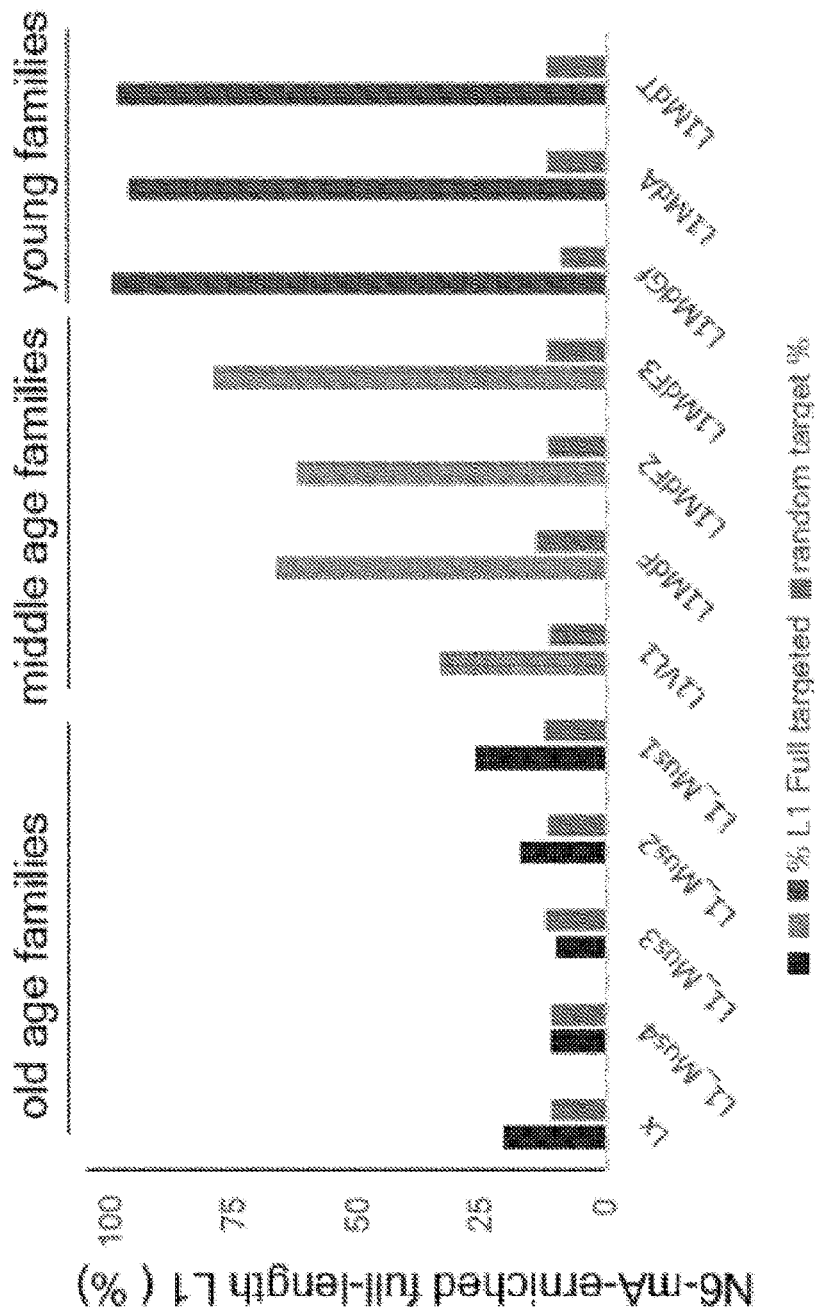
FIG. 10H depicts enrichment of N6-mA in each full length L1 subfamily. Lx, L1_Mus1-4: >6 million years; L1VL1, L1MdF1-4: 1.5-6 million years; L1MdGf, L1MdA, L1mdT: <1.5 million years.
Figures 11A, 11B:
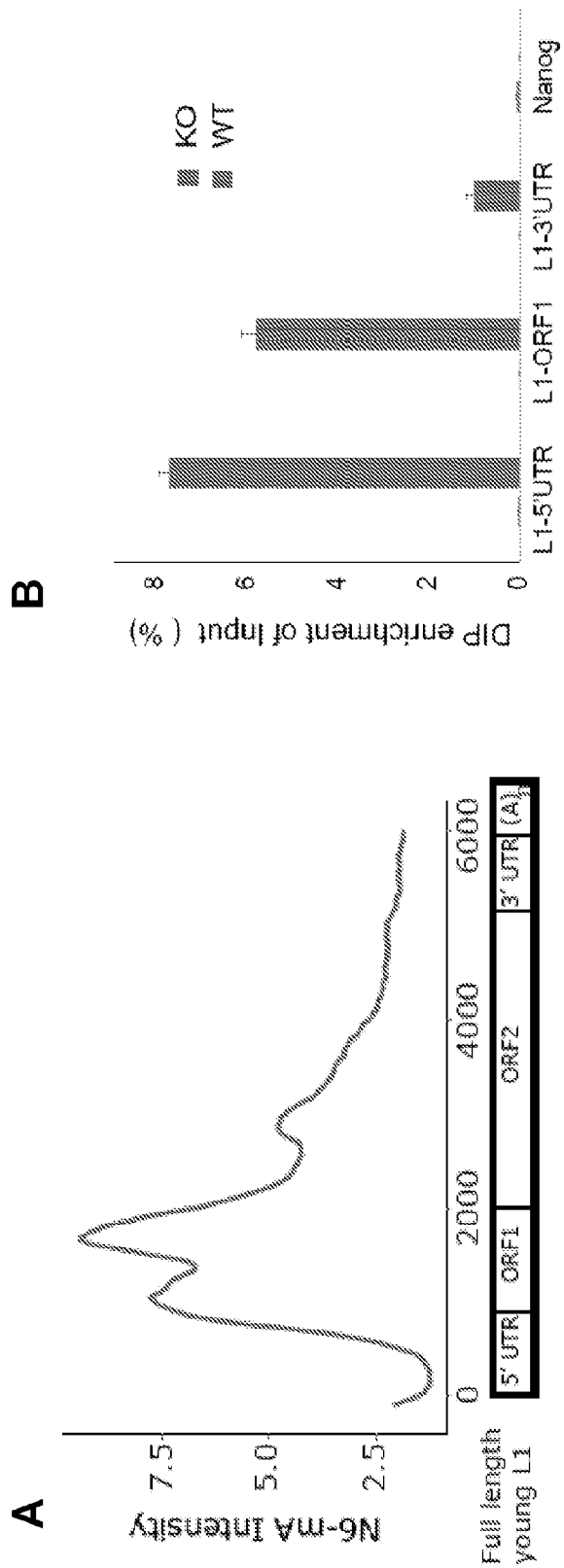
FIG. 11A and FIG. 11B, depicts N6 mA enrichment on 5'-End of young full length L1.

N6-mA peaks called from DIP-Seq are enriched in intergenic regions, but not gene-coding regions (FIG. 10E). Further analysis showed that N6-mA are deposited at LINE elements (FIG. 10F), especially full-length L1s, but not the truncated ones (FIG. 10G). Remarkably, N6-mA deposition at L1s is inversely correlated with their evolutionary age; over 99% of the young full-length L1s are enriched for N6-mA, while no such enrichment is observed on old L1s (FIGS. 4A and 10H). One of the major differences between the young and old L1s is the former retain the 5'UTR and ORF1 regions: old L1s gradually lost their 5'UTR and ORF1 during multiple rounds of remobilization in evolution and therefore, became inactive (Goodier and Kazaqzian, 2008, Cell 135:23-35). Interestingly, N6-mA deposition is biased at the 5'UTR and ORF1 regions than at the 3' UTR (FIG. 11A). This enrichment pattern was further confirmed with qPCR approach (FIG. 11B).

Furthermore, it is well-known that young full-length L1s are strongly enriched on X-chromosomes over autosomes (Abrusán et al., 2008, PLoS Genet 4:e1000172; Bailey et al., 2000, PNAS 97:6634-9) and this analysis corroborated this longstanding observation (P=1.4E-322 FIG. 4B). In agreement, N6-mA peaks in Alkbh1 KO ESCs are also significantly enriched on X-chromosome over autosomes (P=1.4E-322, FIG. 4B). Therefore, these results are consistent with the downregulation of young full-length LINE-1s and protein-coding genes located on X-chromosomes (FIG. 3).

Figure 4D:
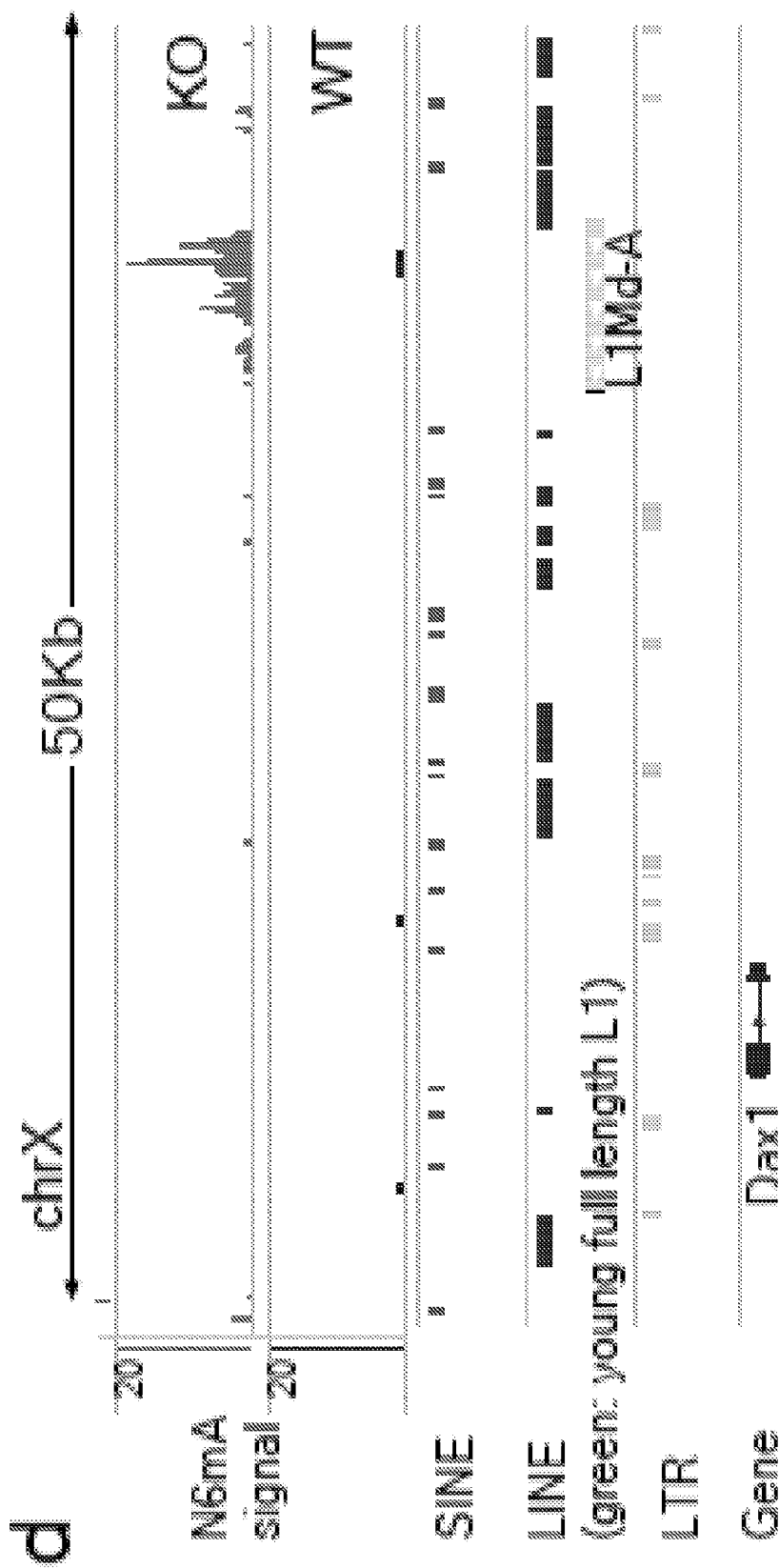
Figure 12A:
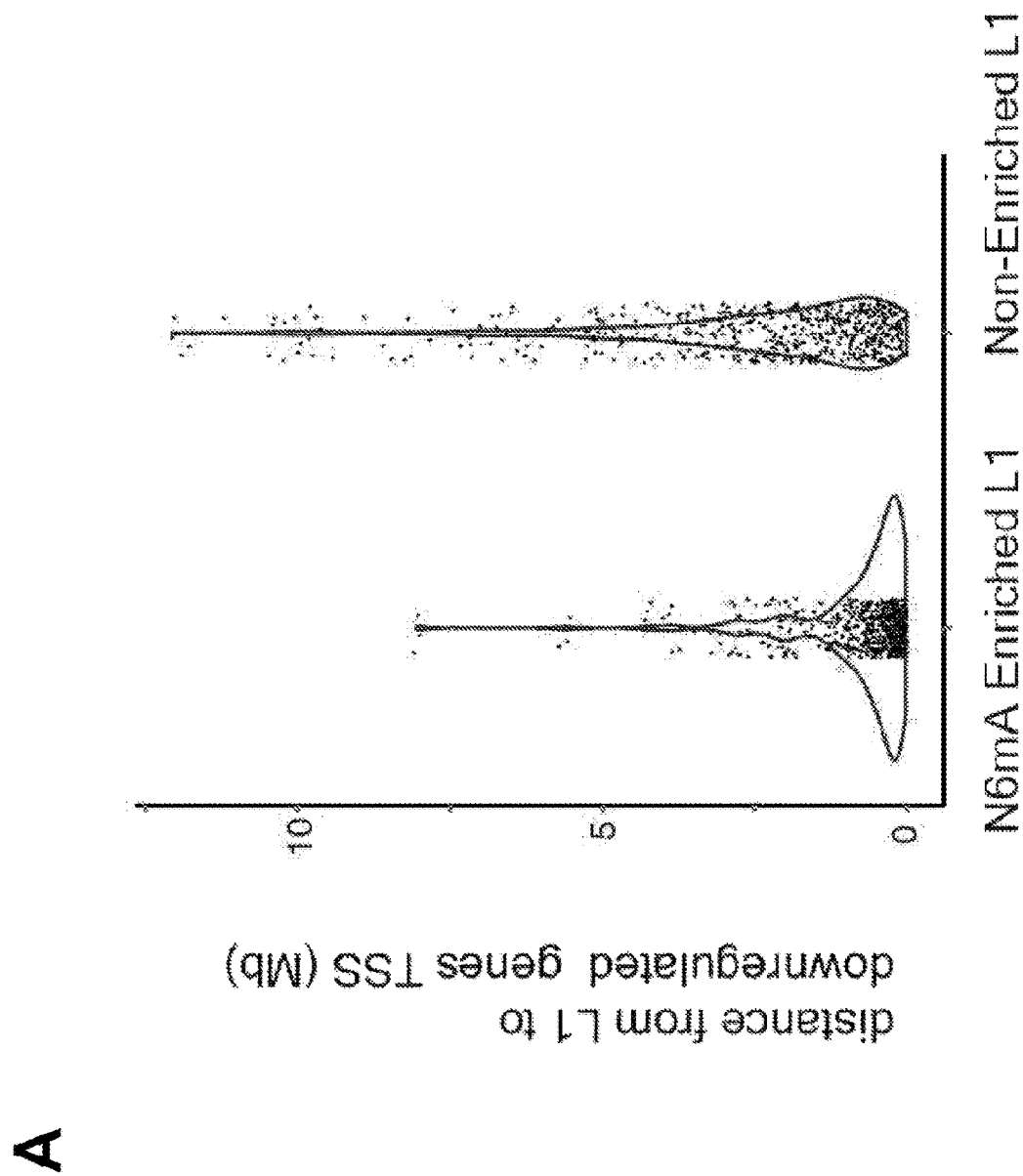
FIG. 12A through FIG. 12C, depicts results of experiments demonstrating the correlation between N6-mA deposition on young full-length L1s and epigenetic silencing.

In classic epigenetic silencing pathways, the distance between the silencing center and genes is a critical determinant. Consistent with notion, further analysis showed that the downregulated genes are located much closer to the N6-mA enriched L1s (median: 424 Kb) than to the non-enriched ones (median: 1.6M) (FIG. 4C). Furthermore, the distances from downregulated genes to the N6-mA enriched L1s fall within a narrow range (25-75%:196 kb-925 kb), while such distances to the non-enriched ones display greater variations (688 Kb-3.2 Mb, FIG. 12A). For instance, the Nr0b1/Dax1 gene that is significantly downregulated in Alkbh1 KO ESCs (FIG. 3) is not enriched for N6-mA; it is, however, located 30 Kb from a N6-mA enriched young full-length L1 (FIG. 4D, labeled in green). Notably, other transposons located in this genomic region are not enriched for N6-mA (FIG. 4D).

Figure 12B:
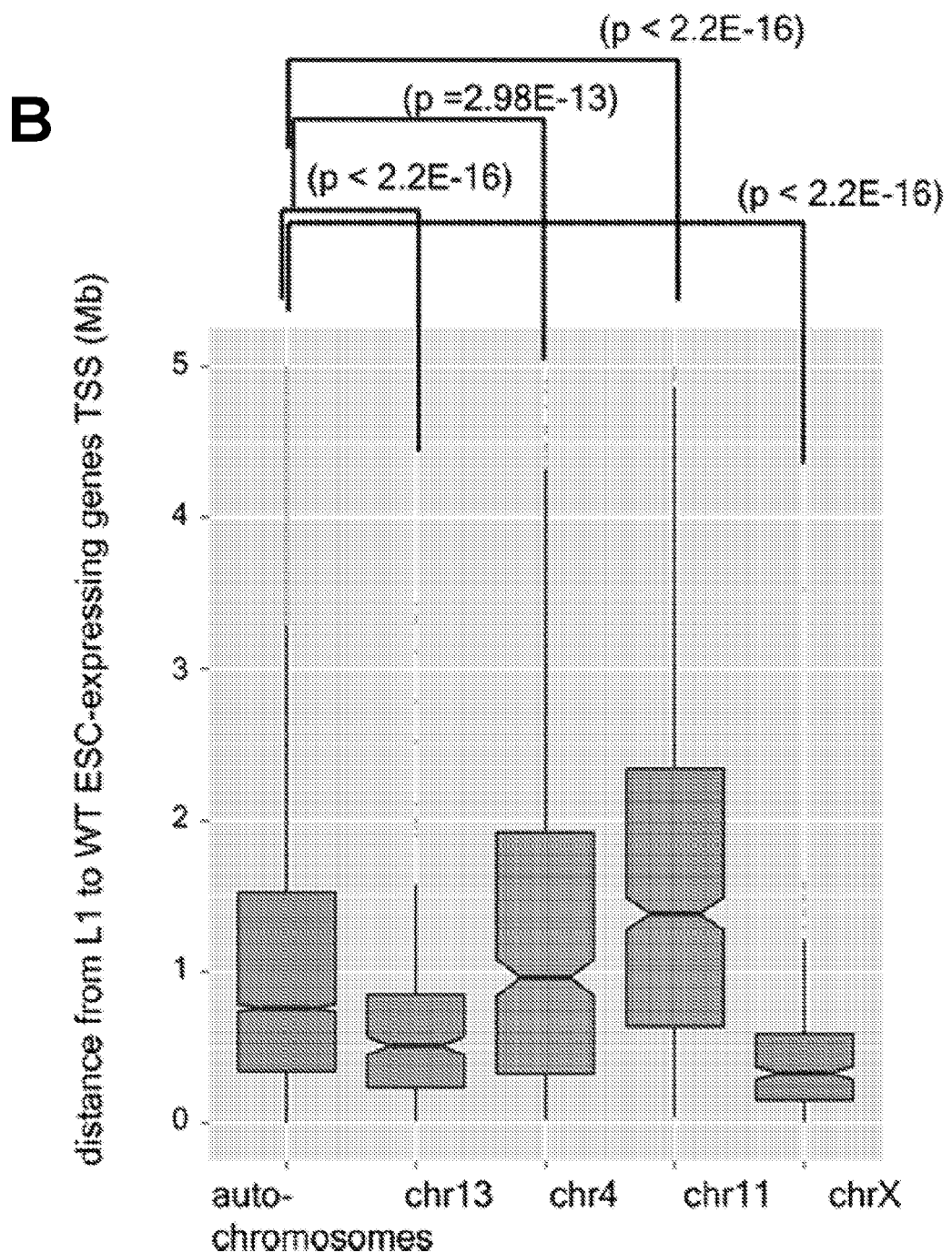
Figure 12C:
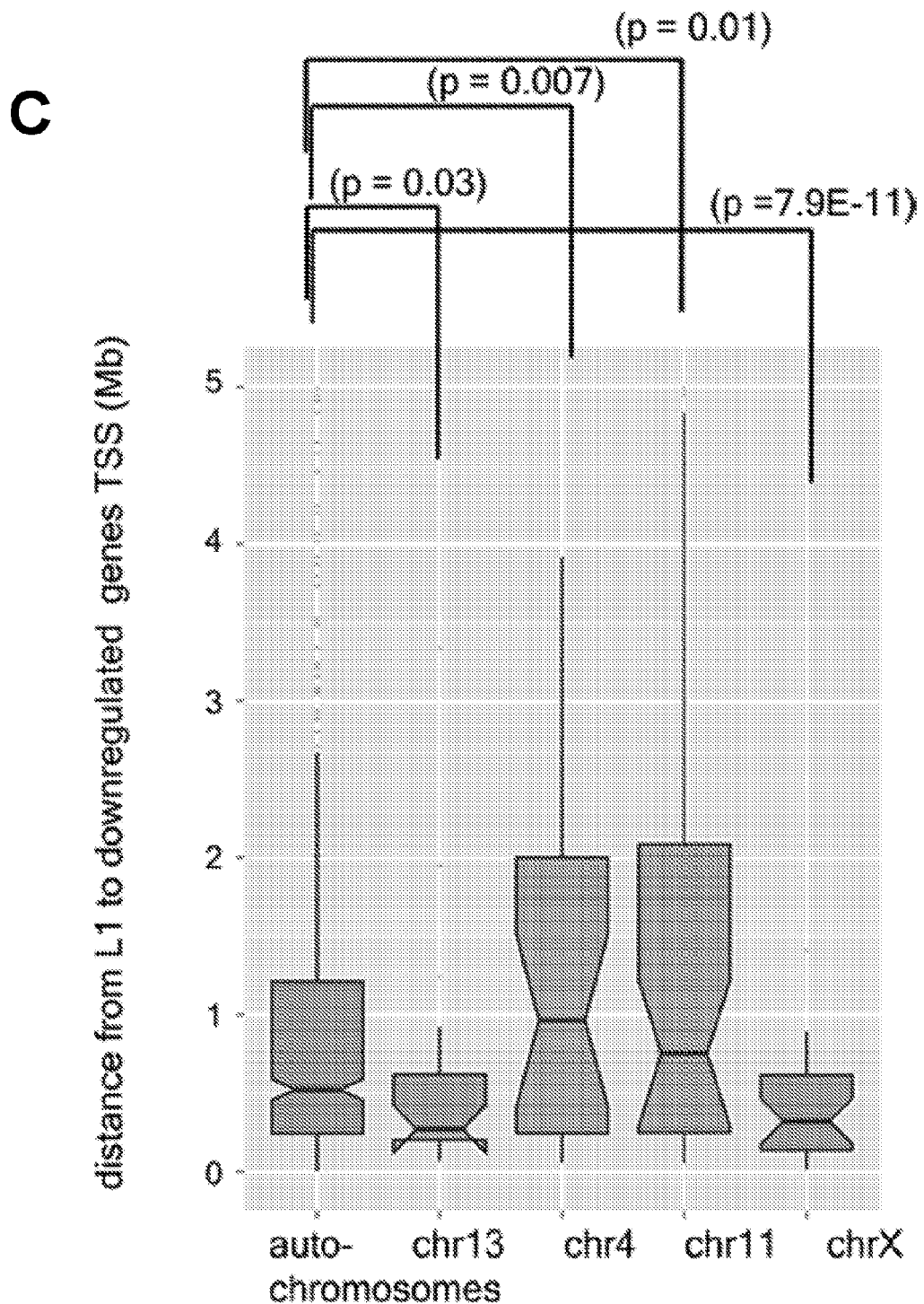

Furthermore, the distances between either the ES-cell expressing genes in WT ESC (FPKM>5.0 in RNA-seq) or downregulated genes in Alkbh1 KO ESCs and young full-length L1s on Chr13 are significantly shorter than the other autosomes (P<2.2E-16, FIGS. 12B and 12C). On the other hand, on a few chromosomes which are devoid of the downregulated genes in Alkbh1 KO ESCs, especially Chr11 and Chr4 (FIG. 3), such distances are significantly longer than the other chromosomes (L1 to ES cell-expressing genes: around 1000 kb, P<2.98E-13; L1 to downregulated genes: around 800 kb, P<=0.01 FIGS. 12B and 12C).

Increasing N6-mA Levels Leads to Epigenetic Silencing on the X-Chromosome, which are Persistent During ES Cell Differentiation The above results indicated that N6-mA may have a direct effect on the transcription of L1s and their neighboring genes. Thus, the impacts of N6-mA deposition on young full-length L1s and their neighboring genes was investigated by interrogating the genome-wide deposition of several key epigenetic marks implicated in transcriptional regulation.

Figures 5A, 5B, 5C:
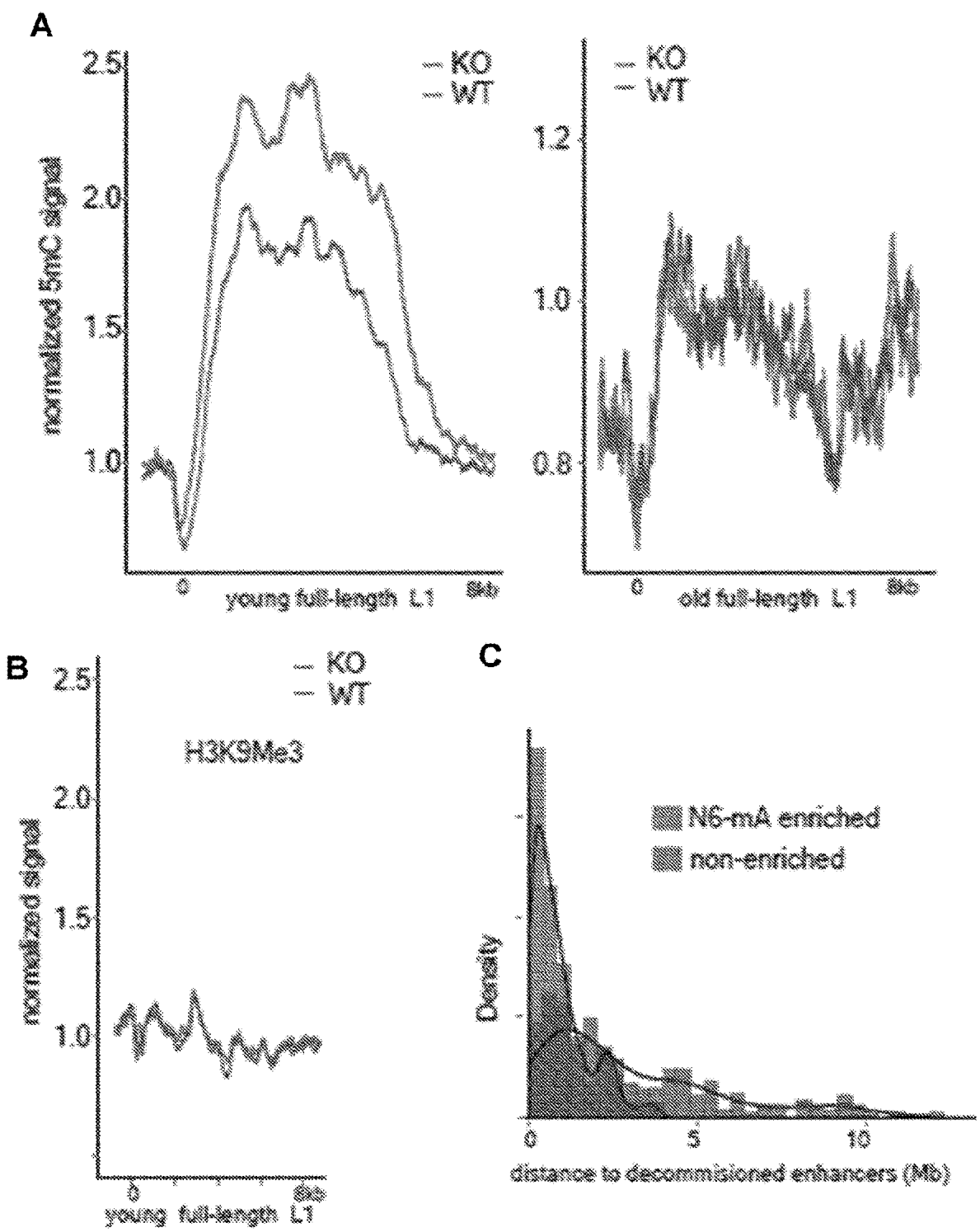
FIG. 5A through FIG. 5E, depicts results of experiments demonstrating N6-mA upregulation induced transcriptional silencing on X-chromosome, which are persistent during differentiation.
Figures 13A, 13B:
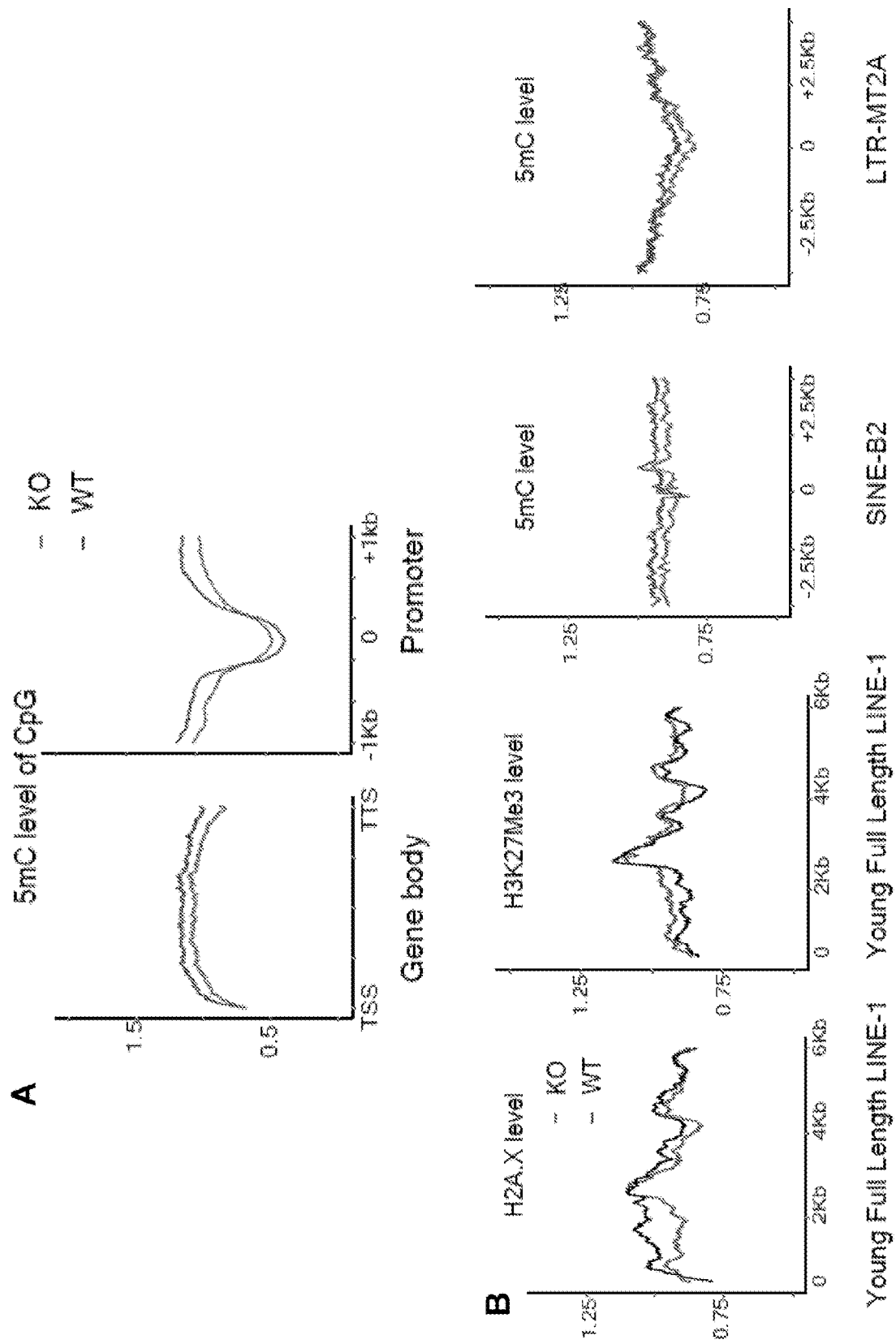
FIG. 13A through FIG. 13E, depicts results of experiments demonstrating N6-mA accumulation correlates with epigenetic silencing.

First, N6-mA's effects on young full-length L1 transposons was studied. This analysis demonstrated that although the genome-wide distribution and intensities of 5 mC methylation sites are similar in Alkbh1 KO to the WT control (FIG. 13A), 5mC level on young full-length L1s is modestly higher in Alkbh1 KO than WT control, while there are no such differences on old L1s (FIG. 5A) or SINEs (FIG. 13B). Other epigenetic silencing marks, such as H3K9me3 (FIG. 5B), H3K27me3 and H2A.X, are deposited on young full-length L1s at similar levels (FIG. 13). Although these results are in agreement with previous works showing that the young L1s are silenced by 5mC in human ESCs (Castro-Diaz et al., 2014, Genes Dev 28:1397-409), additional mechanisms may be also involved since the effects of 5mC seems to be modest.

Figure 13C:
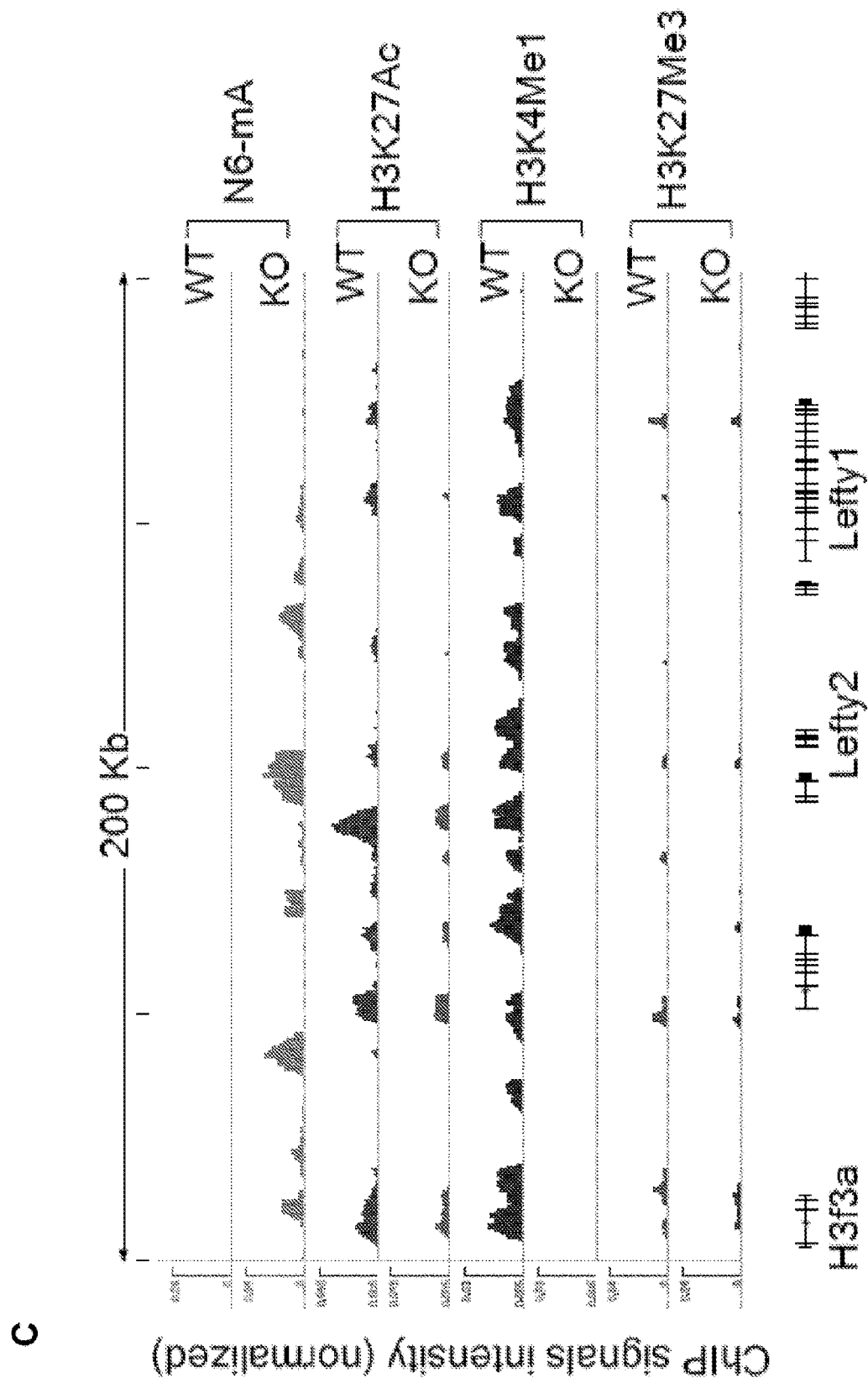
Figures 13D, 13E:
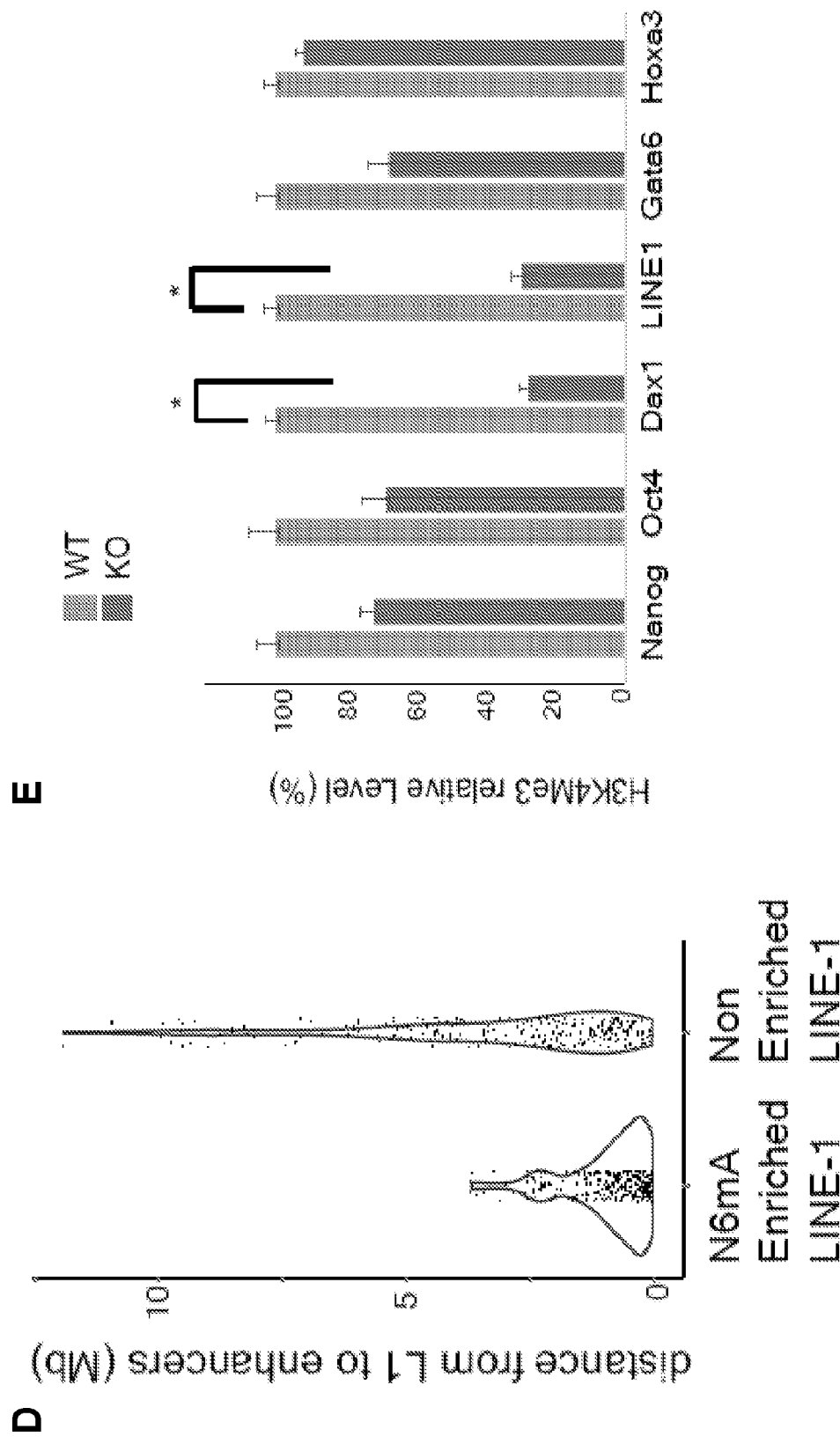
Figure 14A:
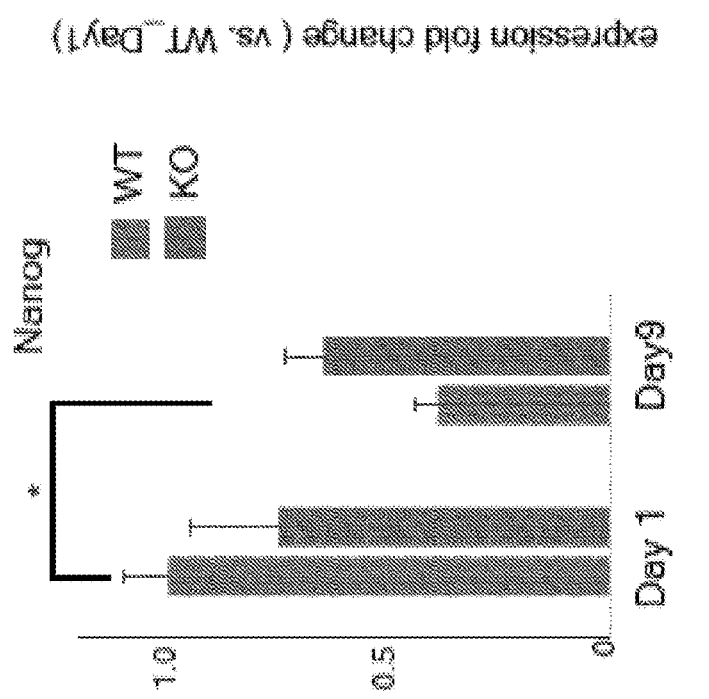
FIG. 14A through FIG. 14E, depicts results of experiments demonstrating N6-mA accumulation results in imbalanced cell fate decisions during ESC differentiation. WT or Alkbh1 KO ESCs were subject to EB differentiation. mRNA samples were collected at day 1 or day 9. Gene expression levels were quantified by RT-qPCR approaches. (* P<0.01, t-test; Error bars, ±the S.E.M. of technical triplicates).
Figure 14B:
Figures 14C, 14D:
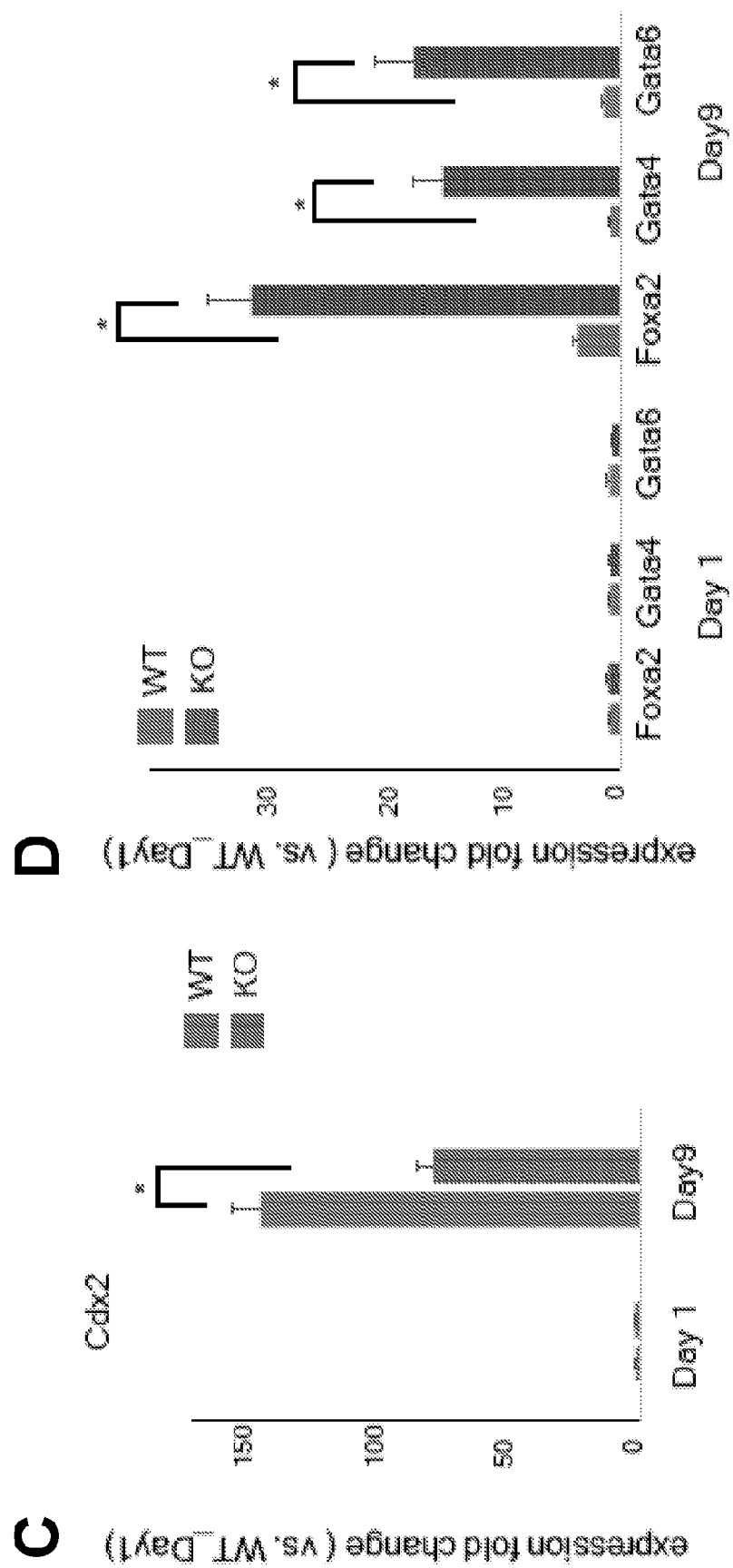
Figures 14E, 14F:
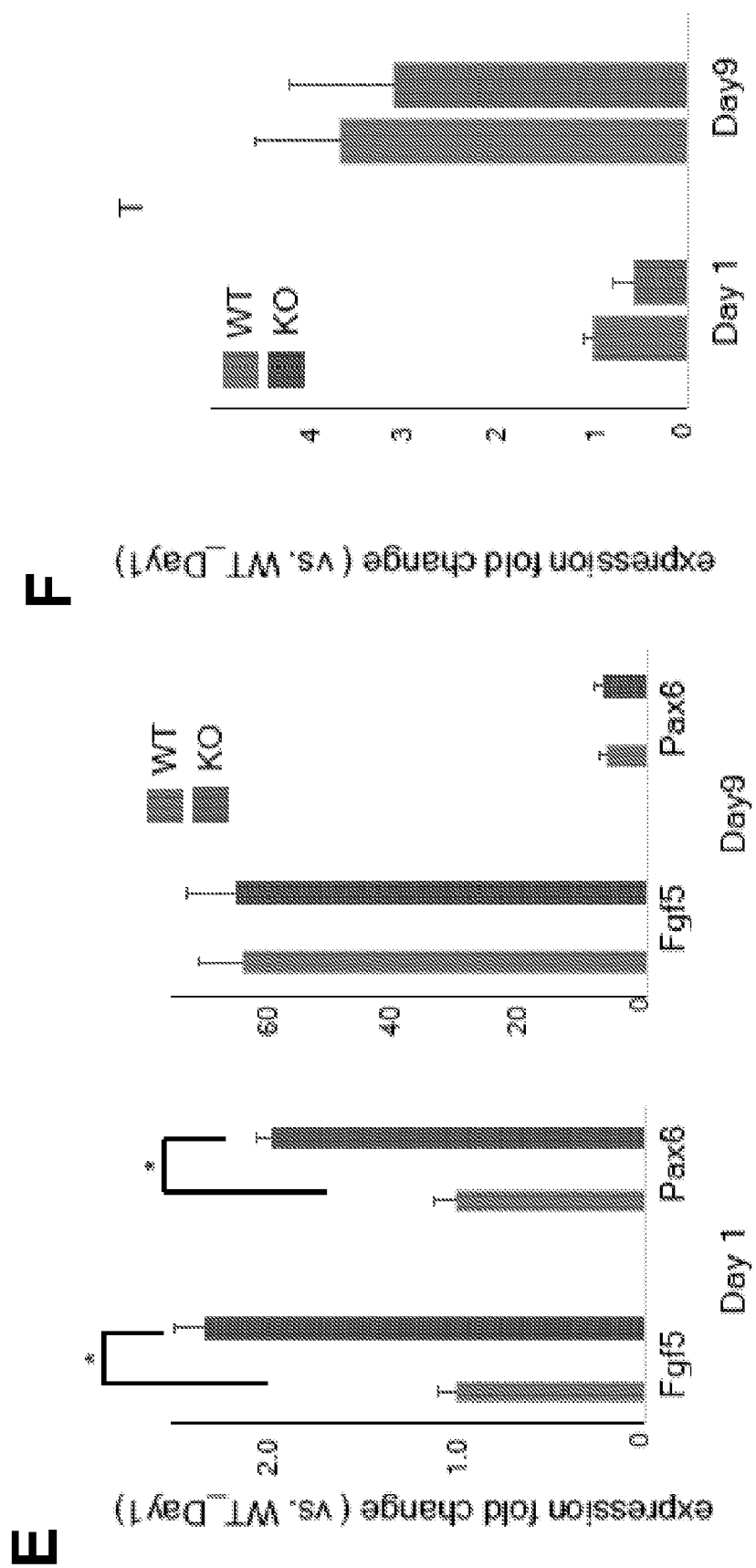
FIG. 14F depicts results demonstrating mesoderm marker, T/Brachyury is similarly expressed in WT- or Alkbh1 KO ESC-derived EBs during differentiation.

Second, the epigenetic status of the enhancers was interrogated and the results demonstrated that 450 enhancers are decommissioned as their H3K27Ac levels are significantly decreased in Alkbh1 KO ESCs (one locus shown in FIG. 13C; (Wu et al., 2016, "DNA Methylation on N6-adenine in mammalian embryonic stem cells," Nature)). These decommissioned enhancers are located much closer to N6-mA-enriched L1s (median: 485 Kb) than non-enriched ones (2.03 Mb, FIG. 5C). Furthermore, such distances fall into a much narrower range (25-75%: 197 Kb-985 Kb) than those to the non-enriched ones (806 Kb-3.8 Mb) (FIG. 13D). Furthermore, the H3K4Me3 levels are reduced at the transcription start sites of the downregulated genes (but not at the unaffected ones) (FIG. 13E). These data demonstrate that N6-mA deposition at L1 is correlated with the downregulation of nearby genes at the transcription level.

Third, the potential effects of N6-mA deposition on X-chromosome genes during differentiation were investigated. Embryoid body (EB) formation and differentiation assays were performed. While the Alkbh1 KO ESCs are able to differentiate in general, the cell fate decisions are imbalanced, as is consistent with previous reports (FIG. 14). Importantly, X-chromosome genes, such as Gm8817 and Rhox6 (Liu et al., 2011, Int J Dev Biol 55:909-16), failed to be activated to the normal level in Alkbh1 KO ESC-derived EBs (FIG. 5D), indicating that N6-mA have long-lasting effects on their activation during differentiation.

N6-mA in Mammalian ESCs and Epigenetic Regulation During Early Embryogenesis

In summary, a novel approach (SMRT-ChIP) was developed to interrogate DNA modifications in specific genomic regions, which led to the discovery of N6-mA in the mammalian genome, together with its demethylase Alkbh1. These findings challenge the prevailing paradigm that 5mC is the only form of DNA methylation in the mammalian genome.

Figures 5D, 5E:
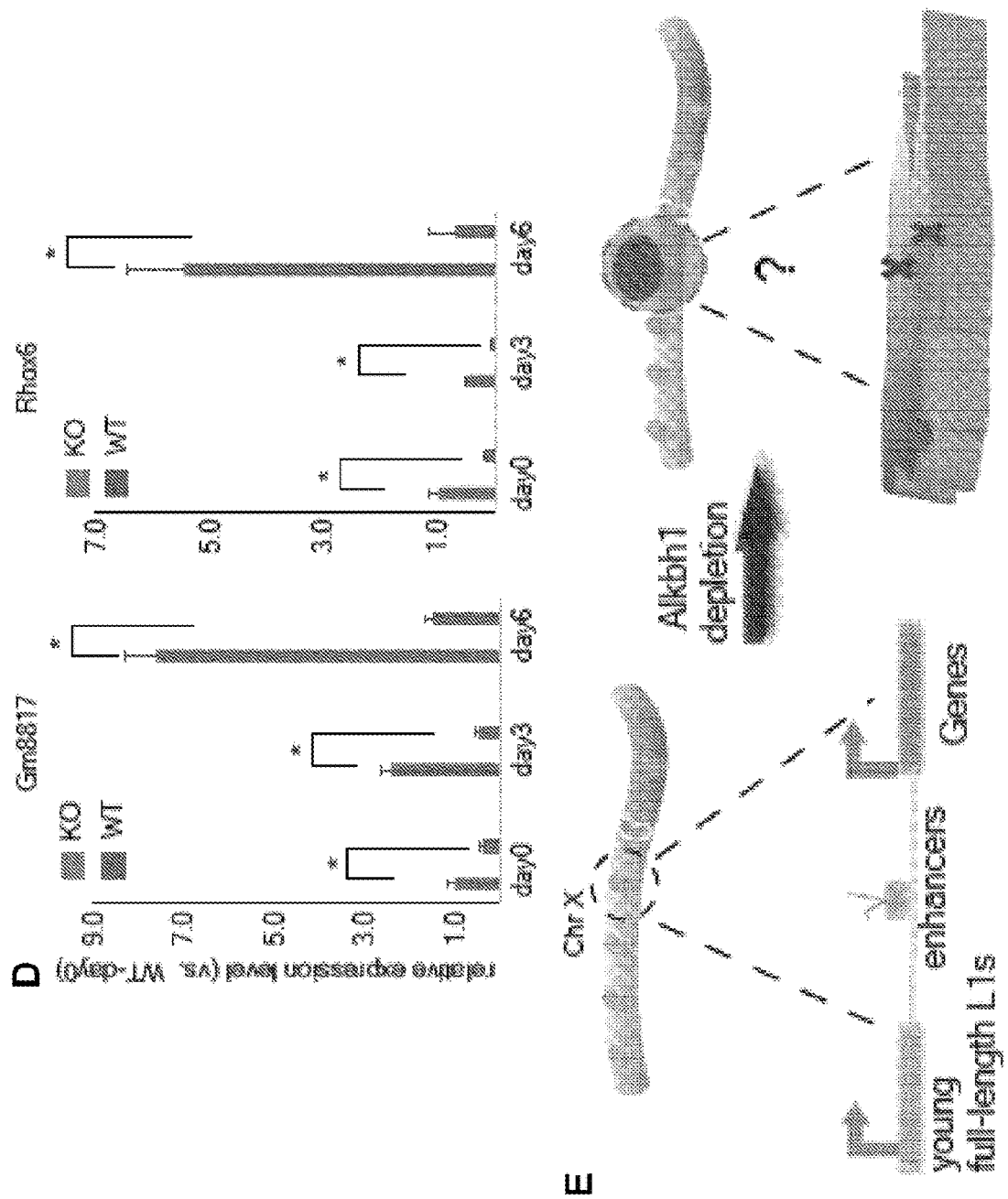

Intriguingly, N6-mA seems to adopt new functions during evolution. In mammalian ESCs, N6-mA accumulation on young full-length L1s correlates with direct silencing of such L1s, as well as decommissioning of nearby enhancers and genes, which are in direct contrast to the role of N6-mA in simple eukaryotes and invertebrates (Zhang et al., 2015, Cell 161:893-906; Greer et al., 2015, Cell 161:868-78; Fu et al., 2015, Cell 161:879-92). In addition, the only Fe++, 2KG dependent dioxygenase orthologue in the *drosophila* genome has been reported to demethylate N6-mA in DNA (Zhang et al., 2015, Cell 161:893-906) and oxidize 5mC in RNA (Delatte et al., 2016, Science 351:282-5), whereas the functions of mammalian orthologues (Tet1-3 and Alkb1-8 genes) are much divergent. N6-mA silencing of L1 transposon in Alkbh1 deficient cells is inversely correlated with the evolutionary age; the full-length young L1s are specifically targeted and silenced by N6-mA. Although the precise reasons of this finding remains elusive, these results showed that N6-mA deposition is strong on the unique 5' UTR and ORF1 regions of such L1s which harbor the promoters. These results also suggest that Alkbh1 must be targeted to these regions in WT ES cells and future investigation will determine molecular underpinning of this specific targeting. Furthermore, as young full-length L1s are strongly enriched on X-chromosome, N6-mA deposition displays a strong bias towards X-chromosome. As such, these findings herein may shed new light to the longstanding "Mary Lyon" hypothesis of L1 function during X-inactivation (Lyon, 1998, Cytogenet Cell Genet 80:133-7). Finally, while young full-length L1s are active during early embryogenesis (Fadloun et al., 2013, Nat Struct Mol Biol 20:332-8), constant activation may cause genomic instability since they are capable of reintegration (Goodier and Kazaqzian, 2008, Cell 135:23-35; Goodier et al., 2011, Genome Res 11:1677-85), which implies the existence of a previously unknown silencing mechanism. Thus, without wishing to be bound to any particular theory, it is possible that N6-mA mediated silencing plays an important role in safeguarding active L1s in the mammalian genomes. The levels of N6-mA are controlled precisely by Alkbh1 in ESCs such that they favor L1 transcription while preventing it from succumbing to overactivation and genomic instability, which is reminiscent of the function of a rheostat (FIG. 5E). In addition, LINE-1s are inactive in a group of South American rodents, in which a new family of endogenous retrotransposons (mysTR) emerge (Erickson et al., 2011, J Virol 85:12315-23). Koziol et al. reported the presence of N6-mA in adult mouse tissues (Koziol et al., 2015, Nat Struct Mol Biol 23:24-30). However, N6-mA levels in these tissues seem to be lower than the detection limit of the DIP-seq approach. Taken together, the discovery of N6-mA in mammalian ESCs sheds new light on epigenetic regulation during early embryogenesis.

Example 2: N6-mA is Overexpressed in Cancer Cells

Figure 15:
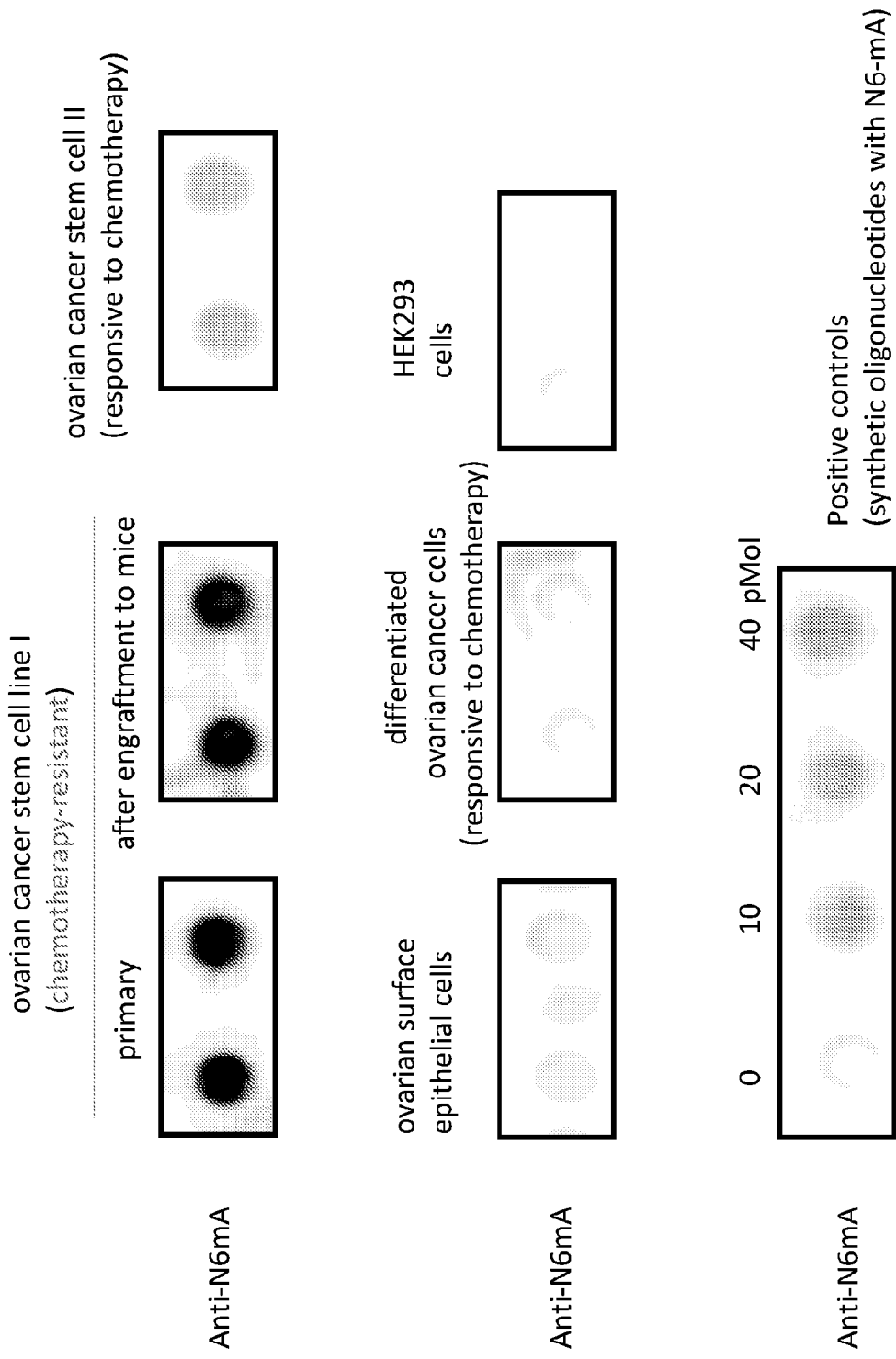
FIG. 15 depicts dotting blotting results using anti-N6-mA antibodies. Only ovary cancer stem cells that are resistant to chemotherapy express appreciable amount of N6-mA, while the differentiated cancer cells or controls do not. Once established, N6-mA becomes a stable mark as it is retained even after engraftment to mice.
Figure 16:
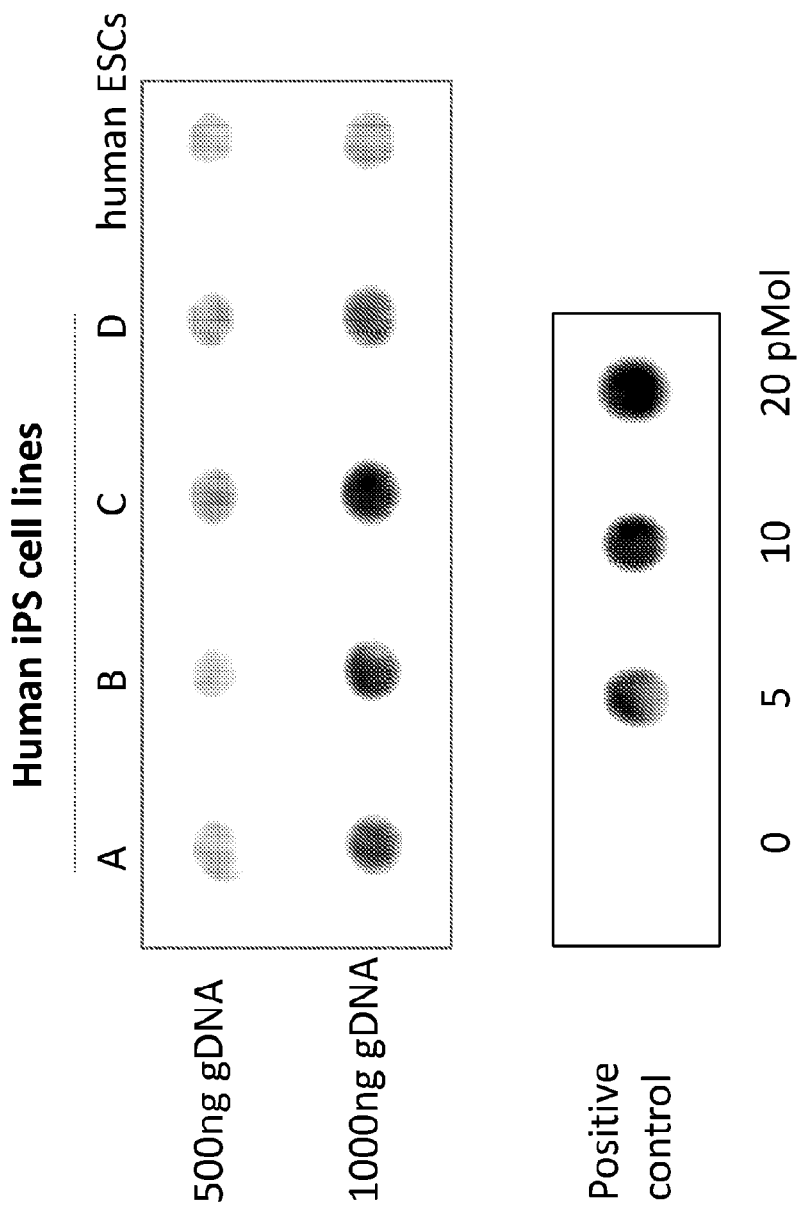
FIG. 16 depicts dotting blotting results using anti-N6-mA antibodies. N6-mA is detectable in both human iPS and ES cells. The level in certain iPS cells are higher than human ES cells.

The data presented herein demonstrates that N6-mA is overexpressed in cancer cell lines. FIG. 15 shows that N6-mA is detectable in an ovarian cancer stem cell line that is chemotherapy resistant. Furthermore, N6-mA expression is maintained in the cancer cells after engraftment into mice. However, ovarian cancer cells that are responsive to chemotherapy and control ovarian cells as well as control HEK293T cells do not express appreciable amounts of N6-mA. FIG. 16 shows that N6-mA is detectable in both human iPS and ES cells. However, the N6-mA levels in certain iPS cells appear to be higher than human ES cells.

N6-mA is also highly upregulated in primary and recurrent human glioblastomas (GBM), while it is undetectable in normal brain tissues. Experiments further demonstrated that N6-mA is specifically upregulated in the cancer stem cells in GBM, which are able to reconstitute tumorigenesis in patient-derived xenograft (PDX) mouse models. Inhibiting N6-mA levels by post-translation modification can effectively curb tumor growth. At the molecular level, N6-mA represses the expression of cell-death-related genes induced by hypoxia, a common condition that stimulates the selection and maintenance of cancer stem cells in various tissues. These results are consistent with those observed in ovarian cancer stem cells, which is consistent with the explanation that N6-mA is a common mechanism cancer stem cells utilize to gain growth advantages.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating cancer in a subject in need thereof, the method comprising:
determining the level of N6-mA in a biological sample of the subject; measuring the level of N6-mA of a comparator control; diagnosing the subject with cancer when the level of N6-mA in the biological sample is different than the level of N6-mA of the comparator control; and administering to the subject a modulator of ALKBHI.

2. The method of claim 1, wherein the level of N6-mA in the biological sample is elevated when compared with the comparator control.

3. The method of claim 1, wherein the level of N6-mA in the biological sample is reduced when compared with the comparator control.

4. The method of claim 1, wherein the comparator control is at least one selected from the group consisting of: a positive comparator control, a negative comparator control and the level of a reference molecule in the biological sample.

5. The method of claim 1, wherein the subject is human.

6. A method for modulating the level of N6-mA in a sample, the method comprising administering a modulator of ALKBHI to the sample.

7. The method of claim 6, wherein the modulator is at least one selected from the group consisting of a chemical compound, a protein, a peptide, a peptidomemetic, an antibody, a ribozyme, a small molecule chemical compound, a nucleic acid, a vector, an antisense nucleic acid molecule.

8. The method of claim 6, wherein the modulator decreases the level or activity of ALKBHI.

9. The method of claim 8, wherein the level of N6-mA is increased.

10. The method of claim 6, wherein the modulator increases the level or activity of ALKBHI.

11. The method of claim 10, wherein the level of N6-mA is decreased.

* * * * *

UNITED STATES PATENT AND TRADEMARK OFFICE
CERTIFICATE OF CORRECTION

PATENT NO. : 11,384,380 B2
APPLICATION NO. : 16/085071
DATED : July 12, 2022
INVENTOR(S) : Andrew Xiao It is certified that error appears in the above-identified patent and that said Letters Patent is hereby corrected as shown below:

On the Title Page

Column 1, Item (60) under the heading Related U.S. Application Data, "Jun. 16, 2016" should read:
-- Mar. 16, 2016 --

Signed and Sealed this
Fourth Day of October, 2022

Katherine Kelly Vidal
*Director of the United States Patent and Trademark Office*